(12) United States Patent
Menzella et al.

(10) Patent No.: US 10,287,521 B2
(45) Date of Patent: May 14, 2019

(54) ENZYMATIC REMOVAL OF STERYL GLYCOSIDES

(71) Applicant: KECLON S.A., Buenos Aires (AR)

(72) Inventors: Hugo Menzella, Rosario (AR); Salvador Peiru, Rosario (AR); Leandro Vetcher, San Francisco, CA (US)

( * ) Notice: Subject to any disclaimer, the term of this patent is extended or adjusted under 35 U.S.C. 154(b) by 0 days.

(21) Appl. No.: 15/595,798

(22) Filed: May 15, 2017

(65) Prior Publication Data

US 2017/0327756 A1    Nov. 16, 2017

Related U.S. Application Data

(62) Division of application No. 14/385,130, filed as application No. PCT/US2013/031769 on Mar. 14, 2013.

(60) Provisional application No. 61/611,949, filed on Mar. 16, 2012, provisional application No. 61/696,588, filed on Sep. 4, 2012.

(51) Int. Cl.

| | | |
|---|---|---|
| *C11B 3/02* | (2006.01) |
| *C12P 7/64* | (2006.01) |
| *C12N 9/42* | (2006.01) |
| *C10L 1/02* | (2006.01) |
| *C12N 9/34* | (2006.01) |
| *C12N 9/20* | (2006.01) |
| *C11C 3/00* | (2006.01) |
| *A23D 9/04* | (2006.01) |
| *C11B 3/00* | (2006.01) |
| *C12P 19/14* | (2006.01) |
| *C12P 19/02* | (2006.01) |
| *C12N 9/26* | (2006.01) |
| *C12N 9/24* | (2006.01) |

(52) U.S. Cl.
CPC .............. *C10L 1/026* (2013.01); *A23D 9/04* (2013.01); *C11B 3/003* (2013.01); *C11C 3/003* (2013.01); *C12N 9/20* (2013.01); *C12N 9/2402* (2013.01); *C12N 9/2408* (2013.01); *C12N 9/2428* (2013.01); *C12N 9/2445* (2013.01); *C12P 7/64* (2013.01); *C12P 7/649* (2013.01); *C12P 19/02* (2013.01); *C12P 19/14* (2013.01); *C12Y 302/01021* (2013.01); *C12Y 302/01104* (2013.01); *C10L 2200/0476* (2013.01); *C10L 2270/026* (2013.01); *Y02E 50/13* (2013.01)

(58) Field of Classification Search
None
See application file for complete search history.

(56) References Cited

U.S. PATENT DOCUMENTS

2011/0173876 A1\*  7/2011  Soe .................. C07J 17/005
                                                                  44/307

OTHER PUBLICATIONS

GenBank Accession No. EHR78077, Feb. 2012 (Year: 2012).\*
L. Nystrom et al. "Enzymatic hydrolysis of steryl ferulates and steryl glycosides", Eur. Food Res. Technol. 227:727-733 (Year: 2008).\*

\* cited by examiner

*Primary Examiner* — Rebecca E Prouty
(74) *Attorney, Agent, or Firm* — Eugenio J. Torres-Oyola; Victor M. Rodriguez-Reyes; Rafael Rodriguez-Muriel

(57) ABSTRACT

The present invention provides compositions and methods related to the production and use of enzymes suitable for reducing the amount of steryl glycosides or saturated monoacyl glycerols in a lipid mixture.

14 Claims, 8 Drawing Sheets

Specification includes a Sequence Listing.

ENZYMATIC REMOVAL OF STERYL GLYCOSIDES

CROSS-REFERENCE

This application is a division of U.S. application Ser. No. 14/385,130, filed Sep. 12, 2012, now abandoned, which is a 371 national stage of PCT/US2013/031769, filed Mar. 14, 2013, which claims the benefit of U.S. Application No. 61/611,949, filed Mar. 16, 2012, and U.S. Application No. 61/696,588, filed Sep. 4, 2012, which are incorporated by reference in their entirety.

BACKGROUND OF THE INVENTION

There is an urgent demand for sustainable and affordable alternatives to petroleum-based fuels. Biofuels are a promising replacement for petroleum-based fuels. Biofuels can be produced from animal or plant matter, such as from corn, sugar cane, sawgrass, soybeans, or algae. As such, they are a renewable and potentially limitless source of fuel. In particular, biodiesels are useful as fuel for vehicles in replacement or as a supplement to petroleum-based diesel fuels. They can be utilized by traditional fuel-burning engines, produce fewer particulates when burnt, have a higher flash point, and are less toxic than petroleum-based fuels. In 2006, biodiesel production in the United States alone was estimated to be more than 1 billion gallons.

Chemically, biodiesels primarily comprise a mixture of monoalkyl esters of long chain fatty acids. Biodiesels are typically produced from lipid transesterification of vegetable oils, including those from soybean, jatropha, palm, rapeseed, sunflower, and others; and/or animal fats with a short-chain monohydric alcohol. The longer the carbon chain of the alcohol used, the better the cold-flow properties. For example, biodiesel comprising fatty acid ethyl esters (FAEEs), derived from ethanol, has better cold-flow properties than biodiesel comprising fatty acid methyl esters (FAMEs), derived from methanol.

However, transesterification produces various unwanted side products, including saturated monoacyl glycerols (SMGs) and steryl glycosides such as steryl glucosides. Acylated steryl glycosides are soluble in oil, but during esterification, they are converted to nonacylated SGs, which are relatively insoluble. If not removed from the biodiesel, steryl glycosides can clog oil filters or cause engine failures. Particles of clumped steryl glycoside molecules can also promote crystallization, aggregation, or precipitation of other compounds in the biodiesel. This further reduces biodiesel flowability and increases the likelihood of clogging. Steryl glycosides typically have a high melting point of around 240° C. and thus cannot simply be heated to allow them to pass through an oil filter. Similarly, SMGs can form crystals in the biodiesel, especially at low temperatures, which creates cold-flow problems and can cause blockages in fuel lines under cold conditions. Additionally, the formation of these precipitates may cause several problems during the biodiesel production process resulting in an increase in production costs.

Insoluble contaminants containing steryl glycosides may appear as haze, precipitates or sediments in biodiesel, which prevents the product from complying with the requirements on contamination and filterability according to biodiesel quality standards.

One method capable of completely removing steryl glycosides and SMGs from biodiesel is distillation. Distillation is energy-intensive, which reduces the cost efficiency and net energy gain of biodiesel production. Filtering, such as through diatomaceous earth, is expensive and not easily scalable to large quantities. Adding adsorbents requires an additional removal step, and is similarly expensive and time-consuming. Other methods includes the centrifugation methods disclosed in WO 2010 004423.

Steryl glycosidases can be used to digest steryl glycosides, producing a glycoside and a sterol. Similarly, lipases can be used to eliminate SMGs. However, steryl glycosidases and lipases currently used in the field are inefficient and do not effectively reduce the amount of steryl glycosides and SMGs in biodiesel.

SUMMARY OF THE INVENTION

The present invention provides isolated thermostable enzymes that are capable of hydrolyzing the glycosidic bond of steryl glycosides or acylated steryl glycosides and methods of making and using such enzymes. This solves the challenges of producing biodiesel fuel which is higher quality, more cost-effective, and competitive in the global market.

The platform disclosed herein uses genetic engineering, synthetic biology and directed evolution to rapidly generate new and improved enzymes that can significantly reduce current production costs and provide premium high-quality biodiesel by eliminating major impurities in an environmental-friendly and commercially competitive way. The invention also provides methods and compositions for generating designer enzymes that eliminate key impurities in plant-based biodiesel, such as steryl glycosides and saturated monoacylglycerols (SMGs) which result in the formation of insoluble materials that compromise quality and performance of the end product.

In one aspect, the present invention provides a method for reducing steryl glycoside in a sample. The method comprises: mixing a thermostable enzyme with a sample comprising steryl glycoside under a condition suitable for the thermostable enzyme for a suitable period of time to degrade the steryl glycoside, thereby reducing steryl glycoside in the sample to obtain a processed sample.

In some embodiments, the sample comprises oil, fat, or biofuel (e.g. biodiesel).

In some embodiments, the steryl glycoside comprises steryl glucoside. In some embodiments, the steryl glycoside has a solubility that is more than 50 ppm, more than 80 ppm, or more than 100 ppm.

In some embodiments, the thermostable enzyme is capable of hydrolyzing the glycosidic bond of steryl glucosides or acylated steryl glucosides.

In some embodiments, the thermostable enzyme comprises a glycosidase enzyme.

In some embodiments, the thermostable enzyme comprises a glucosidase enzyme.

In some embodiments, the thermostable enzyme comprises a variant of an enzyme selected from Table 1.

In some embodiments, the thermostable enzyme comprises a variant having an amino acid sequence that has at least 95% identity to a sequence selected from the sequences of Table 1.

In some embodiments, the thermostable enzyme comprises an amino acid sequence selected from the sequences of Table 1.

In some embodiments, the sample comprises 0.1% to 30% of water.

In some embodiments, the mixing step is carried out at a temperature that is between about 50° C. and about 110° C., such as above about 65° C., above about 70° C., or above about 75° C.

In some embodiments, the mixing step is carried for about 30 minutes to 24 hours.

In some embodiments, the steryl glycoside is reduced by at least 20% to 80%, inclusive.

In some embodiments, the processed sample comprises less than 20 ppm of the steryl glycoside.

In some embodiments, the mixing step comprises mixing the sample with an enzyme selected from beta-glucosidases, sterol-esterases, amyloglucosidases, and pectinases.

In some embodiments, the method further comprises collecting the processed sample.

In another aspect, the present invention provides an oil produced by the methods provided herein.

In another aspect, the present invention provides an isolated thermostable enzyme that is capable of hydrolyzing the glycosidic bond of steryl glycosides or acylated steryl glycosides. In some embodiments, the enzyme has an activity of at least 5 g of steryl glycoside per gram of enzyme per hour at a temperature that is between about 50° C. and about 99° C., such as above about 65° C., 70° C., 75, 80, 85, or 90° C. In some embodiments, the thermostable enzyme comprises a variant of one of the enzymes listed in Table 1. In some embodiments, the thermostable enzyme comprises a variant having an amino acid sequence that is at least 95% identical to the sequence of one of the enzymes listed in Table 1. In some embodiments, the thermostable enzyme comprises an amino acid sequence selected from the sequences of Table 1.

In another aspect, the present invention provides a method for generating a gene encoding a variant steryl glucosidase, comprising: (a) growing in a cultural medium a plurality of host cells transformed with a library of variant steryl glucosidase genes, wherein expression of each variant steryl glucosidase gene is under the control of a promoter that linearly responds to concentrations of an inducer added to the culture medium, wherein the host cells require ergosterol to grow and are unable to synthesize ergosterol, and wherein the cultural medium comprises steryl glucosides and a first concentration of the inducer so as to permit only a host cell expressing a variant steryl glucosidase with sufficient activity to form a colony; and (b) recovering the variant steryl glucosidase gene from the colony. In some embodiments, the method further comprises repeating the steps (a) and (b) wherein the library of variant steryl glucosidase genes is generated from the variant steryl glucosidase gene recovered from the previous iteration, and wherein in the new iteration cycle a lower concentration of the inducer is added to the cultural medium.

In some embodiments, the library is generated using error prone PCR or oligonucleotide directed mutagenesis.

In some embodiments, an expression vector used to transform host cells with variant steryl glucosidase genes comprises a yeast expression vector.

In some embodiments, an expression vector used to transform host cells with variant steryl glucosidase genes is inducible by an inducer selected from: $Cu^{2+}$ and beta-estradiol.

In some embodiments, the host cell comprises a yeast mutant cell.

In some embodiments, the method further comprises designing and synthesizing codon optimized sequences encoding the variant steryl glucosidase.

In another aspect, the present invention provides a method for producing a recombinant steryl glucosidase, comprising: (a) expressing codon optimized sequences provided herein or obtained using a method provided herein in a suitable heterologous host cell to generate recombinant steryl glucosidase; and (b) isolating the recombinant steryl glucosidase. In some embodiments, the growing step occurs at or above 50° C., 55° C., 60° C., 65° C., 70° C., 75° C., 80° C., or 85° C.

In another aspect, the present invention provides a host cell expressing a gene produced by the methods provided herein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
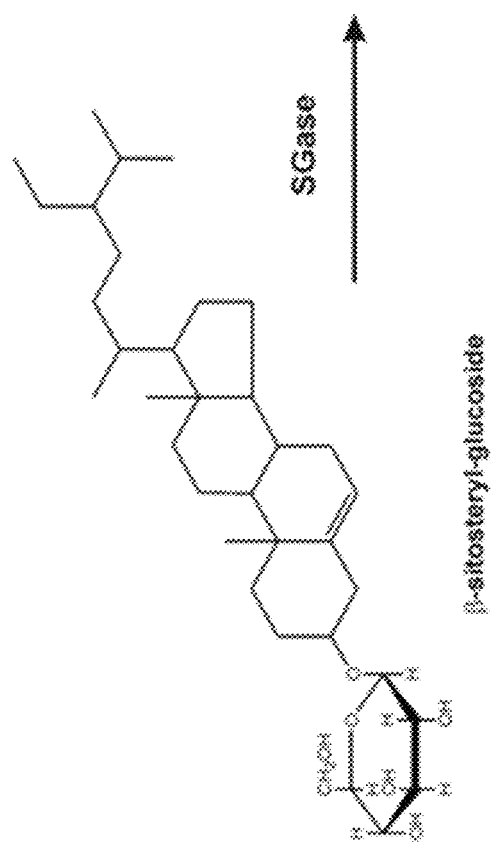
FIG. 1 depicts enzymatic hydrolysis of an example steryl glycoside (SG), β-sitosteryl-glucoside.
Figure 1:
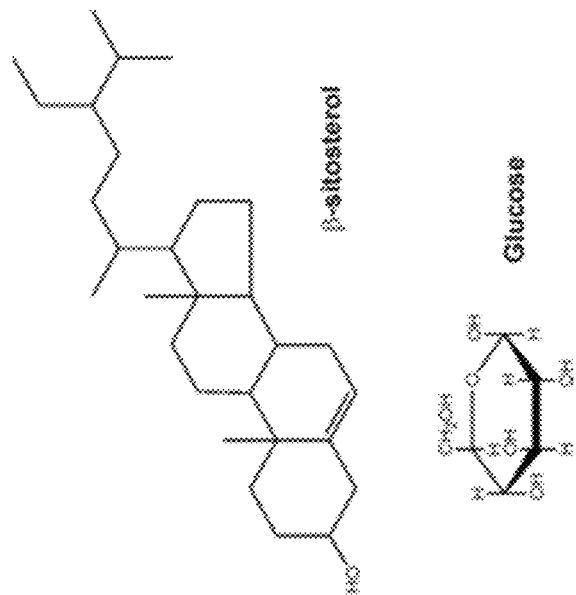

The present invention is directed to compositions and methods for reducing the amount of steryl glycosides in a biodiesel sample. The invention further provides methods to increase efficiency of enzymatic degradation of steryl glycosides. In some embodiments, elevated temperatures may be used to increase efficiency of enzymatic degradation. In some embodiments, a thermostable enzyme may be used, such as a thermostable steryl glycosidase or a thermostable lipase. In some embodiments, pressure, additives, or other techniques may be used to increase efficiency of enzymatic activity.

Biodiesels, such as those generated by lipid transesterification, can contain various contaminating compounds, including but not limited to steryl glycosides and saturated monoacyl glycerols (SMGs). Acylated steryl glycosides are soluble in oil, but during esterification, they are converted to nonacylated steryl glycosides, which are relatively insoluble. Nonacylated steryl glycosides can also be naturally present. Precipitation of steryl glycosides and SMGs can occur at any temperature. Even low levels, such as 10-90 ppm of steryl glycoside in biodiesel, can form aggregates. These aggregates, if present in biodiesels, can clog oil filters and also promote crystallization, aggregation, or precipitation of other compounds.

WO2007/076163 describes filtration methods to remove steryl glucosides, including the use of additives to increase precipitation or aggregation. However, this procedure introduces an extra filtration step which can be costly and/or time consuming. Additionally, removal of steryl glucosides by filtration or centrifugation requires waiting for the steryl glucosides to aggregate and precipitate before they can be removed from the biodiesel or starting oil. These methods also reduce the overall yield of biodiesel.

WO 2010/102952 and WO 2010/004423, herein incorporated by reference, describe methods using enzymatic catalysis to remove steryl glucosides from biodiesel and oil. However, WO 2010/102952 and WO 2010/004423 describe processes where the optimal reaction occurs at 50° C. At 50° C., the solubility of steryl glucosides in biodiesel is around 50 ppm. However, crude biodiesel typically contains 10-300 ppm of steryl glucosides. Thus, a significant fraction of steryl glucoside is insoluble at 50° C. and, therefore, not accessible to the enzymes.

Steryl glycosides and SMG aggregates in biodiesels are resistant to enzymatic degradation because their aggregation prevents the enzymes from efficiently accessing or digesting the compounds. Enzymatic digestion works the most efficiently when the substrates are free in solution. Steryl glycosides solubility in biodiesel increases with temperature, which reduces aggregation and increases accessibility. However, high temperatures can reduce enzymatic activity, such as by heat denaturation of the enzymes.

The present invention overcomes problems related to the presence of steryl glycosides in biodiesel by using newly discovered or artificially generated enzymes capable of hydrolyzing steryl glycosides at high temperature, providing methods for the inexpensive production of such enzymes and using such enzymes to remove steryl glycosides from biodiesel, biodiesel precursors, or biodiesel derivatives.

I. Samples

Samples as described herein can refer to any oil, fat or biofuel. Biofuels can include any energy source derived from organic material, including but not limited to cellulosic ethanol and biodiesels. In some embodiments, a sample is a starting material, precursor or intermediate product used for biofuel or biodiesel production, processing, or refinement. For example, a biofuel precursor can refer to any oil or other sample suitable for generating biofuel. A biodiesel precursor can refer to any oil or other sample suitable for generating biodiesel. In some embodiments, the oils, fats, biofuels, or precursors thereof are derived from an organic source, including but not limited to animal fats, such as tallow, lard, chicken fat, yellow grease, fish oil, and byproducts of animal fat processing; plant oils, including but not limited to oils from rapeseed, soybeans, flax, sunflower, safflower, nasturtium, palm, coconut, hemp, olive, sesame, peanut, babassu nut, castor, corn, canola, jatropha, mustard, jojoba, rice bran, cottonseed, pennycress, lupin, algae, halophytes such as dwarf saltwort; waste vegetable or other oils, such as oils left over from food production, or products generated therefrom. In some embodiments, the sample is an intermediate product, a waste product, or a by-product of oil or fat refining, including but not limited to soap stock, acid oil, fatty acid distillates, gums, by-products of Omega-3 fatty acid derivates from fish oil, fat trap grease, free fatty acids, fractions of oil obtained by physical separations, or any combinations thereof. In some embodiments, samples for biodiesel generation are derived from algae.

In some embodiments, the sample comprises steryl glycosides. "Steryl glycosides" as used herein refers to molecules comprising one or more carbohydrate units linked to a hydroxyl group of a sterol molecule. Examples of sterol molecule include but are not limited to phytosterols such as campesterol, stigmasterol, sitosterol, avenasterol, desmosterol, fucosterol, sargasterol, brassicasterol and dihydrositosterol; zoosterols such as cholesterol; or saturated "stanol" versions of such sterols. A carbohydrate may be a sugar moiety with examples that include but are not limited to glucose, sucrose, xylose, arabinose, fructose, galactose, mannose, glucuronides, sulfated steryl glycosides or diglycosides. A sugar moiety may be linked to a sterol moiety via a glycosidic bond. In some embodiments, a sugar moiety is acylated at the carbon 6 position. Examples of steryl glycosides include but are not limited to acylated steryl glycosides, nonacylated steryl glycosides, steryl glucosides, and β-sitosteryl-glucoside. When a sugar moiety is glucose, the steryl glycoside may be referred to as a steryl glucoside. In the present invention the term steryl glycoside is meant to encompass steryl glucoside.

Figure 3:
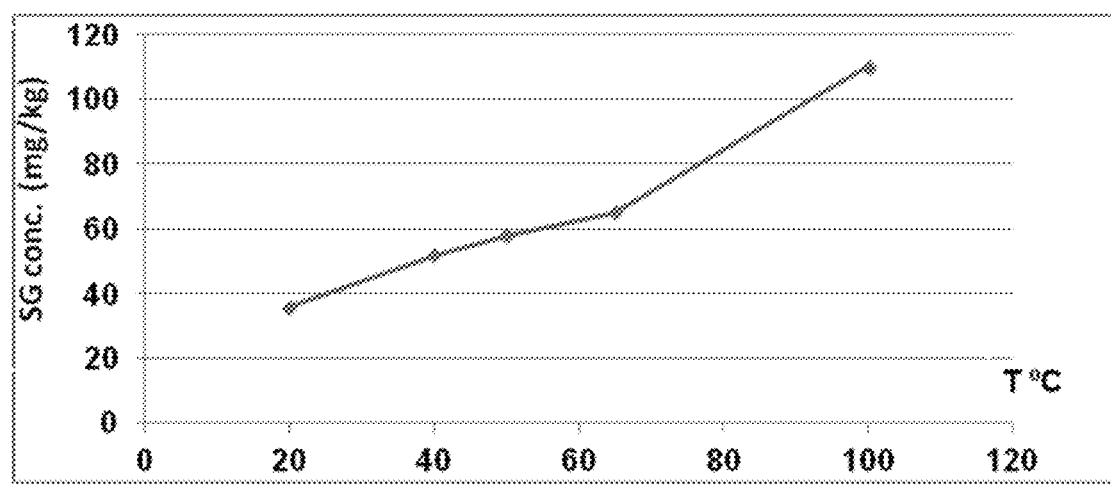
FIG. 3 is a graph depicting the temperature-dependent solubility of steryl glucoside in biodiesel.

As used herein, solubility refers to the amount of a solute that can be dissolved within a solvent. A solute's solubility generally varies based on temperature, pressure and on the composition of the solvent. Solubility of steryl glycosides in biodiesels and oils generally increases with temperature. FIG. 3 depicts the solubility of a steryl glucoside mixture in biodiesel generated from soybean oil at different temperatures. Steryl glucoside solubility was evaluated in distilled soybean biodiesel. 100 parts-per-million ("ppm") of steryl glucoside was added to biodiesel and incubated at 100° C. for 24 hours ("h") to the indicated temperatures and incubated for 4 h prior to steryl glycoside solubility determination. In some embodiments, solubility of steryl glucoside in the sample is at least 30 ppm, at least 40 ppm, at least 50 ppm, at least 60 ppm, at least 70 ppm, at least 80 ppm, at least 90 ppm, at least 100 ppm, or at least 110 ppm. Solubility can be measured by determining the amount of steryl glycoside in the biodiesel or biodiesel precursor, excluding any precipitated steryl glycoside. The amount of steryl glycoside in the oil or fat (e.g. biofuel substrate) and/or the biofuel may be determined by any conventional process.

The amount of steryl glycoside in an oil or fat may vary depending on the sample source. The amount of steryl glycosides in crude soybean oil is higher than in some other oils that are commonly used to make biodiesel such as, for example, rape seed, corn, cotton or sunflower oil. In some embodiments, the concentration of steryl glycoside in a sample is at least 30 ppm, at least 40 ppm, at least 50 ppm, at least 60 ppm, at least 70 ppm, at least 80 ppm, at least 90 ppm, at least 100 ppm, at least 110 ppm, at least 120 ppm, at least 130 ppm, at least 140 ppm, at least 150 ppm, at least 200 ppm, at least 250 ppm, or at least 300 ppm by weight. Concentration as used herein generally refers to the total amount of a substance (e.g., steryl glycoside) in a sample, including both precipitates and dissolved species. Concentrations may be determined, for example, by solid-phase extraction and gas chromatography as described in Phillips et al. (2005), Journal of Food Lipids, 12(2), 124-140, which is incorporated by reference in its entirety.

The quality of the biodiesel strongly depends on the amount of insoluble material that it contains. This may be measured using a standard filter blocking test such as that according to ASTM method D 2068 "Standard Test Method for Filter Blocking Tendency of Distillate Fuel Oils", Total Contamination Test according to EN12662:1998 or ASTM D7321-11, and Cold Soak Filtration Test according to ASTM D7501-12. In general, when steryl glycosides are removed in accordance with the present invention, the biodiesel is of better quality when compared with a comparable control biodiesel in which steryl glycosides have not been removed.

In some embodiments, the sample comprises other insoluble compounds, such as sterol esters, sterol alkyl esters, sulfated sterol glucosides, and waxes.

In some embodiments, the methods as described herein are used to remove steryl glycosides from a sample prior to processing to produce biodiesel. In other embodiments, the methods described are used after biodiesel production. In some embodiments, the methods are used in combination with other methods for removing unwanted components, such as distillation or filtration.

II. Enzymes

The invention as described herein encompasses a variety of enzymes for reducing the amounts of steryl glycosides. As used herein, an enzyme refers to a polypeptide or ribozyme that can catalyze a chemical reaction.

Steryl glycosidases are enzymes capable of hydrolyzing the glycosidic bond in a steryl glycoside and/or an acylated steryl glycoside to produce a free sugar residue and a free sterol, an example of which is shown in FIG. 1. Steryl glycosidases include but are not limited to glucosidase enzymes, such as β-glucosidase or amyloglucosidase enzymes.

To efficiently perform enzymatic reduction of SGs at high temperatures, thermostable steryl glycosidases are needed. Thermostable enzymes are enzymes that retain at least a portion of their activity at high temperatures. For example, thermostable enzymes can retain a percentage of its peak activity above the temperature required for peak activity. Such temperatures may be at or above about 50° C., 60° C., 65° C., 70° C., 75° C., 80° C., 85° C., 90° C., 95° C., 98° C., 100° C., 105° C., 110° C., or 115° C. In some embodiments, the percentage of activity retained at any of the above temperatures is least 30%, 40%, 50%, 60%, 70%, 80%, 90%, 95%, 98%, 99%, or more than 99% of peak activity. In some embodiments, thermostable enzymes are thermophilic enzymes, wherein the peak activity of the enzyme occurs at relatively higher temperature such as at or above 50° C., 60° C., 65° C., 70° C., 75° C., 80° C., 85° C., 90° C., 95° C., 98° C., 100° C., 105° C., 110° C., or 115° C. In some embodiments, thermostable enzymes are thermophilic enzymes, wherein the peak activity of the enzyme occurs at between 80 and 90° C.

Enzymes may be of naturally occurring wild-type sequences, or natural or artificially generated variants. Variants may have an amino acid sequence that is at least 60%, at least 70%, at least 75%, at least 80%, at least 85%, at least 90%, at least 92%, at least 94%, at least 95%, at least 96%, at least 97%, at least 98%, or at least 99% identical to a wild-type enzyme. In some embodiments, the enzyme has at least 60%, at least 70%, at least 75%, at least 80%, at least 85%, at least 90%, at least 92%, at least 94%, at least 95%, at least 96%, at least 97%, at least 98%, at least 99% identity, or 100% identity to a sequence listed in Table 1. Variants can comprise any type of variation, including but not limited to genetic mutations such as point mutations, insertions, deletions, or transversions.

In some embodiments, the enzymes are variants of naturally occurring, wild-type enzymes. In some embodiments, the variant enzymes have increased activity compared to wild-type enzymes. In some embodiments, the variant enzymes have better activity than wild-type enzymes under the conditions used to purify biodiesel, such as ionic content, pressure, or temperature. In some embodiments, the variant enzymes are more stable or have better activity in certain temperature ranges compared to wild-type enzymes, such as at temperatures above about 25° C., above about 37° C., above about 45° C., above about 50° C., above about 65° C., above about 70° C., between about 25° C. and about 50° C., between about 25° C. and about 65° C., between about 37° C. and about 50° C., between about 37° C. and about 65° C., between about 45° C. and about 65° C., between about 25° C. and about 110° C., between about 37° C. and about 110° C., between about 45° C. and about 110° C., between about 50° C. and about 110° C., between about 60° C. and about 110° C., between about 70° C. and about 110° C., between about 80° C. and about 110° C., between about 37° C. and about 95° C., between about 45° C. and about 95° C., between about 50° C. and about 95° C., between about 60° C. and about 95° C., and between about 70° C. and about 95° C. In some embodiments, the variant enzymes are thermostable or thermophilic versions of wild-type enzymes. In some embodiments, thermostable or thermophilic enzymes can be wild-type enzymes, such as those isolated from thermophiles.

Steryl glycosidase activity can be determined by measuring the glucose resulting from the hydrolysis of steryl glycoside, by means of colorimetric methods such as the Glucose Oxidase assay. In some embodiments, steryl glycosidase activity is measured by mixing a steryl glycosidase in appropriate buffer with water and the enzyme to be tested. The reaction mixture is incubated at a selected temperature in a shaking incubator. Sterol products are extracted with chloroform, and the chloroform phase removed and evaporated, such as under nitrogen. The resulting sample is then analyzed, for example by using HPTLC or mass spectroscopy, to determine the presence and, optionally, the amount of sterol produced. Further details on an example method of how to assay steryl glycosidase activity can be found in WO2010/004423. In some embodiments, enzyme activity is measured over a range of temperatures. In some embodiments, peak activity is calculated as enzyme activity at an optimal temperature at which the enzyme has highest activity.

A. Identifying Proteins with Steryl Glycosidase Activity

Preparations containing mixtures of unidentified enzymes with steryl glucosidase activity have been described but no polypeptides carrying such specific activity have been identified. There also various enzymes that are known to have beta-glusidase activity. However, there is no known report that these enzymes possess steryl glycosidase. Inventors of the present invention surprisingly discovered that certain beta-glusidase also have steryl glycosidase, some of which are provided herein in Table I. Presented in Table 1 are polypeptide sequences of non-limiting examples of enzymes capable of hydrolyzing the glycosidic bond of steryl glycosides or acylated steryl glycosides to form a sugar and a corresponding sterol or acylated sterol. Other steryl glycosidase enzymes can be isolated and/or identified from cells or cellular extracts using methods known in the art.

Enzymes suitable for use with this invention can be found and isolated from a variety of species, including animals, plants, protists, microbes, and fungi. In some embodiments, suitable enzymes can be isolated from thermophilic species. Examples of species that may contain lipases or steryl glycosidase suitable for use with the invention include species of the genus *Sulfolobus*, including *S. acidocaldarius*, *S. islandicus* and *S. solfataricus*; *Pyrococcus*, including *P. horikoshii* and *P. furiosus*, *Caldivirga* such as *C. maquilingensis*; *Vulcanisaeta*, including *V. distributa* and *V. moutnovskia*; *Acidilobus* such as *A. saccharovorans*; *Thermoproteus* such as *T. uzoniensis*; *Thermoplasma* such as *T. volcanium*; *Ignisphaera* such as *I. aggregans*; *Thermosphaera* such as *T. aggregans*; *Thermococcus*, including *T. litoralis*, *T. kodakarensis*, *T. barophilus*, *T. alcaliphilus* and *T. sibiricus*; *Aciduliprofundum* such as *A. boonei*; *Aspergillus*, including *A. niger*, *A. aculeatus*, *A. fumigatus*, *A. flavus*, *A. kawachii*, *A. oryzae*, *A. terreus*; *Thermomyces* such as *T. lanuginosa*; *Candida*, including *C. Antarctica* and *C. albicans*; *Saccharomyces*, such as *S. cerevisiae*.

Steryl glycosidases can be identified by methods known in the art, such as by biochemical purification from fractional extracts with glycosidase activity. Such fractional extracts may be taken from cellular samples, such as lysates, or from mixed compositions comprising glycosidase activity. Some such mixed compositions are commercially available, such as Grindamyl™ Ca 150 (available from Danisco A/S). Other suitable enzymes include but are not limited to amyloglucosidases such as AMG8000 (available from Danisco A/S). Glycosidase activity can be measured by any method described herein or known in the art.

TABLE 1

| Sequence ID number | Species | Amino Acid sequence |
|---|---|---|
| SEQ ID No.: 1 | Sulfolobus acidocaldarius | MLSFPKGFKFGWSQSGFQSEMGTPGSEDPNSD WHVWVHDRENIVSQVVSGDLPENGPGYWGN YKRFHDEAEKIGLNAVRINVEWSRIFPRPLPKP EMQTGTDKENSPVISVDLNESKLREMDNYAN HEALSHYRQILEDLRNRGPHIVLNMYHWTLPI WLHDPIRVRRGDFTGPTGWLNSRTVYEFARFS AYVAWKLDDLASEYATMNEPNVVWGAGYAF PRAGEPPNYLSERLSEIAKWNIIQAHARAYDAI KSVSKKSVGIIYANTSYYPLRPQDNEAVEIAER LNRWSFFDSIIKGEITSEGQNVREDLRNRLDWI GVNYYTRTVVTKAESGYLTLPGYGDRCERNS LSLANLPTSDFGWEFFPEGLYDVLLKYWNRY GLPLYVMENGIADDADYQRPYYLVSHIYQVH RALNEGVDVRGYLHWSLADNYEWSSGFSMRF GLLKVDYLTKRLYWRPSALVYREITRSNGIPEE LEHLNRVPPIKPLRH |
| SEQ ID No.: 2 | Sulfolobus solfataricus | MYSFPNSFRFGWSQAGFQSEMGTPGSEDPNTD WYKWVHDPENMAAGLVSGDLPENGPGYWG NYKTFHDNAQKMGLKIARLNVEWSRIFPNPLP RPQNFDESKQDVTEVEINENELKRLDEYANKD ALNHYREIFKDLKSRGLYFILNMYHWPLPLWL HDPIRVRRGDFTGPSGWLSTRTVYEFARFSAYI AWKFDDLVDEYSTMNEPNVVGGLGYVGVKS GFPPGYLSFELSRRAMYNIIQAHARAYDGIKSV SKKPVGIIYANSSFQPLTDKDMEAVEMAENDN RWWFFDAIIRGEITRGNEKIVRDDLKGRLDWI GVNYYTRTVVKRTEKGYVSLGGYGHGCERNS VSLAGLPTSDFGWEFFPEGLYDVLTKYWNRY HLYMYVTENGIADDADYQRPYYLVSHVYQV HRAINSGADVRGYLHWSLADNYEWASGFSM FGLLKVDYNTKRLYWRPSALVYREIATNGAIT DEIEHLNSVPPVKPLRH |
| SEQ ID No.: 3 | Sulfolobus islandicus | MYSFPKNFRFGWSQAGFQSEMGTPGSEDPNT DWYKWVHDPENIAAGLVSGDLPENGPGYWG NYKTFHDNAQKMGLKMARLNVEWSRIFPNPL PKPQNFDESKQDVTEVEINQNELRRLDEHANK DALNHYREIFKDLKSRGIYFILNMYHWPLPSW LHDPIRVRRGDLSGPTGWLSTRTVYEFARFSA YIAWKFDDLVDEYSTMNEPNVVGGLGYVGV KSGFPPGYLSFELSRKAMYNIIQAHVRAYDGIK SVSKKPIGIIYANSSFQPLTEKDMEAVEMAEYD NRWAFFDAIIRGEIMKGSEKVVRDDLRGRLD WIGVNYYTRTVVKKTEKGYVSLGGYGHGCER NSVSLAGLPTSDFGWEFFPEGLYDVLTKYWNR YHLHMYVTENGIADDADYQRPYYLVSHVYQ VHRAINSSADVRGYLHWSLADNYEWASGFSM RFGLLKVDYGTKRLYWRPSALVYREIATNGGI TDEIEHLNSVPPIRPLRH |
| SEQ ID No.: 4 | Caldivirga maquilingensis | MDISFPKSFREGWSQAGFQSEMGTPGSEDPNT DWYVWVHDPENIASGLVSGDLPEHGPGYWGL YRMFHDNAVKMGLDIARINVEWSRIFPKPMPD PPQGNVEVKGNDVLAVHVDENDLKRLDEAA NQEAVRHYREIFSDLKARGIHFILNFYHWPLPL WVHDPIRVRKGDLSGPTGWLDVKTVINFARF AAYTAWKFDDLADEYSTMNEPNVVHSNGYM WVKSGFPPSYLNFELSRRVMVNLIQAHARAY DAVKAISKKPIGIIYANSSFTPLTDKDAKAVEL AEYDSRWIFFDAIIKGELMGVTRDDLKGRLDW IGVNYYSRTVVKLIGEKSYVSIPGYGYGCERNS ISPDGRPCSDFGWEFYPEGLYDVIMKYWSRYH LPIYVTENGIADAADYQRPYYLVSHIYQVYRAI QEGANVKGYLHWSLTDNYEWASGFSMRFGL LQVDYSTKKQYWRPSAYVYREIAKSKAIPEEL MHLNTIPPTRSLRR |
| SEQ ID No.: 5 | Vulcanisaeta distributa | MTLSFPKGFREGWSQAGFQHEMGIPGDEDTNS DWWVWVHDRDNIVSGLVSGDLPENGPGYWS LYRVEHDNAVRMGLDIARVNVEWSRIFPKPM PEPPNGNVEVVGDKVIKVDVDERDLRRLDETA NKAAIEHYRAIFNDLKNRNIFFILNLYHWPLPL WVHDPIRVRKGDLSGPTGWLDIKTVINFARFA AYVAWKLDDLVDMYSTMNEPNVVAWNGYIN VKSGFPPSYLNPDLARKALVNLIQAHARAYDA IKTVSRKPVGIIYANNAYTPLTEKDSKAVELAE QDARWSFFDAVIHGNLYGEVREDLRNRLDWI GANYYSRLVVKLISDNSYAIVPGYGHACERNS VSPDNRPCSDFGWEFYPEGLYDVLTKYWRRY HLPIYVTENGIADSADYLRPYYLVSHIYQVYR ALSDGVDVRGYLHWSLTDNYEWASGFSMRF GLLYVDYTTKRQYWRPSAYIYREIALNKAIPD ELMHLNTIPPVRSLRK |
| SEQ ID No.: 6 | Vulcanisaeta moutnovskia | MTLSFPQDFREGWSQAGFQHEMGIPGDEDPNS DWWVWVHDRDNIASGLVSGDLPENGPGYWS LYRVEHDNAVRMGLDIARINVEWSRVFPKPM PEPPSGNVEVVGDNVIKVDVDERDLRRLDEAA NKAAVEHYRVMFNDLKNRNIFFILNLYHWPLP |

TABLE 1-continued

| Sequence ID number | Species | Amino Acid sequence |
|---|---|---|
| | | LWIHDPIRVRRGDLSGPTGWLDVKTVINFARF AAYVAWRFDDLVDMYSTMNEPNVVAYAGY ANVKSGFPPGYLNPGLARRALINLIQAHARAY DAIKAISRKPVGIIYANNAYTPLTEKDAGAVEL AEQDARWSFFDAIIHGNLYGEVRDDLRGRLD WIGVNYYSRLVVRLTGENSYSVVPGYGHACE RNSVSPDNKPCSDFGWEFYPEGLYDVLMKYW RRYRLPMYVTENGIADAADYLRPYYLVSHVY QVHRALGDGADVRGYLHWSLTDNYEWASGF SMRFGLLYVDYSSKKQYWRPSAYIYREIAMN KAIPDELMHLNAVPPIRPLRR |
| SEQ ID No.: 7 | Vulcan-isaeta dis-tributa | MTLSFPKGFREGWSQAGFQHEMGIPGDEDTNS DWWVWVHDRDNIVSGLVSGDLPENGPGYWS LYRVEHDNAVRMGLDIARVNVEWSRIFPKPM PEPPNGNVEVVGDKVIKVDVDERDLRRLDETA NKAAIEHYRAIFNDLKNRNIFFILNLYHWPLPL WVHDPIRVRKGDLSGPTGWLDIKTVINFARFA AYVAWKLDDLVDMYSTMNEPNVVAWNGYIN VKSGFPPSYLNPDLARKALVNLIQAHARAYDA IKTVSRKPVGIIYANNAYTPLTEKDSKAVELAE QDARWSFFDAVIHGNLYGEVREDLRNRLDWI GANYYSRLVVKLISDNSYAIVPGYGHACERNS VSPDNRPCSDFGWEFYPEGLYDVLTKYWRRY HLPIYVTENGIADSADYLRPYYLVSHIYQVYR ALSDGVDVRGYLHWSLTDNYEWASGFSMRF GLLYVDTTKRQYWRPSAYIYREIALNKAIPD ELMHLNTIPPVRSLRK |
| SEQ ID No.: 8 | Vulcan-isaeta mout-novskia | MTLSFPQDFRFGWSQAGFQHEMGIPGDEDPNS DWWVWVHDRDNIASGLVSGDLPENGPGYWS LYRVEHDNAVRMGLDIARINVEWSRIFPKPM PEPPSGNVEVVGDNVIKVDVDERDLRRLDEAA NKAAVEHYRVMFNDLKNRNIFFILNLYHWPLP LWIHDPIRVRRGDLSGPTGWLDVKTVINFARF AAYVAWRFDDLVDMYSTMNEPNVVAYAGY ANVKSGFPPGYLNPGLARRALINLIQAHARAY DAIKAISRKPVGIIYANNAYTPLTEKDAGAVEL AEQDARWSFFDAIIHGNLYGEVRDDLRGRLD WIGVNYYSRLVVRLTGENSYSVVPGYGHACE RNSVSPDNKPCSDFGWEFYPEGLYDVLMKYW RRYRLPMYVTENGIADAADYLRPYYLVSHVY QVHRALGDGADVRGYLHWSLTDNYEWASGF SMRFGLLYVDYSSKKQYWRPSAYIYREIAMN KAIPDELMHLNAVPPIRPLRR |
| SEQ ID No.: 9 | Acidil-obus saccha-rovorans | MAVTFPKDFLFGWSQAGFQSEMGTPGSEDPNS DWYAWVHDRENIAAGLVSGDFPENGVAYWH NYRKFHDAAQAMGLTAARIGVEWSRIFPRPTF DVKVDAEVKGDDVLSVYVSEGALEQLDKMA NRDAINHYREMFSDLRSRGITFILNLYHWPLPL WLHDPIAIRRGNLSAPSGWLDVRTVIEFAKSA YVAWKLDDLVYMYSTMNEPNVVWGLGYAA VKSGFPPGYLCLECAGRAMKNLVQAHARAYD AVKAITKKPVGVIYANSDFTPLTDADREAAER AKFDNRWAFFDAVVRGQLGGSTRDDLKGRLD WIGVNYYTRQVVRARGSGYEIVPGYGHGCEP NGVSPAGRPCSDFGWEFYPEGLYNVLKEYWD RYHLPLLVTENGIADEGDYQRPYYLVSHVYQ VHRALQDGVNVIGYLHWSLADNYEWASGFSK RFGLLMVDYSTKRLHWRPSAFIYREIAKSRAIT DEIEHLNSVPPLRGLSPGHR |
| SEQ ID No.: 10 | Thermo-proteus uzon-iensis | MRKFPSGFRWGWSGAGFQFEMGLPGSEDPNT DWFWVHDPENIAAGLVSGDFPENGVAYWH LYKQEHDDTVKMGLNTIRENTEWSRIFPKPTF DVRVHYEVREGRVVSVDITEKALEELDKLAN KDAVAHYREIFSDIKSRGLYFILNLYHWPMPL WVHDPIKVRRGDLSGRNVGWAETTVVEFAK YAAYVAWKFGDLADEFSTENEPNVVTYNLGFIA VKAGPPGYLSFQMRRAAVNLITAHARAYD AIRLTSKKPVGVIYAASPVYPLTEADKAAAER AAYDGLWFFLDAVAKGVLDGVAQDDLKGRL DWLGINYYSRSVVVKRGDGYAGVPGYGFACE |
| SEQ ID No.: 11 | Thermo-plasma volcanium | PNSVSRDGRPTSDFGWEIYPEGLYDILTWAWR RYGLPLYVTENGIADQHDRWRPYYLVSHLAQ LHRAIQDGVNVKGYLHWSLTDNYEWASGFSK KFGLIYVDLSTKRHYWRPSAYIYREIASSNGIP DELEHLEKVPVASPEVLRGLRSL MVENNFPEDFKFGWSQSGFQSEMGYDNAMD DKSDWYVVVHDKENIQSGLVSGDMPENGPG YWNNYKSFHEAAQNMGLKMARIGVEWSRLF PEPFPEKIMADAKNNSLEINNNILSELDKYVNK DALNHYIEIFNDIKNRNIDLIINMYHWPLPVWL SDPVSVRKGIKTERSGWLNDRIVQLFALFSSYI VYKMEDLAVAFSTMNEPNVVYGNGFINIKSGF PPSYLSSEFASKVKNNILKAHSLAYDSMKKITD KPVGIIYANTYFTPLDPEKDNDAIAKADSDAK WSFFDPLIKGDKSLGINGNKLDWIGINYYTRT MLRKDGDGYISLKGYGHSGSPNTVTNDKRPTS DIGWEFYPEGLEYVIMNYWNRYKLPMYVTEN GIADNGDYQRPYYLVSHIASVLRAINKGANVK GYLHWSLVDNYEWALGFSPKFGLIGYDENKK LYWRPSALVYKEIATKNCISPELKHLDSIPP INGLRK |
| SEQ ID No.: 12 | Ignis-phaera aggregans | MGLKYPKEFIFGFSESGFQFEMGLPGSEDPNTD WWVWVHDPENIASTLVSGDFPENGPGYWHL YRQDHDIAERLGMDGARIGIEWSRIFSKPTFDV KVDVARDERGNIVYIDVAEKALEELDRIANKD AVNHYREILSDWKNRGKKLIINLYHWTLPLWL HDPIKVRKLGIDRAPAGWVDERTVIEFVKYVA YIAWKLGDLPDLWCTMNEPNVVYSIGYINIKI GYPPGYLSFEAASKAMKHLVEAHARAYEVLK RFTNKPVGIIYVTTYHEPLKESDRDVAEAAMY QAVFDFLDSITIGRSMSIGERKDLEKHLDWLGI NYYSRLVVERYGNAWRVLPGYGFACIPGGTS LAGRPCNDAGWETYPEGLYIMLKRCWERYRL PIIVTENGTADAIDRLRPRYLATHLYQVWKAL SEGVDIRGYLHWALVDNYEWSSGFRMRFGLV HVDFETKKRYLRPSALLFREIASSKEIPDEFMH MTQPQILI |
| SEQ ID No.: 13 | Thermos-phaera aggregans | MKFPKDFMIGYSSSPFQFEAGIPGSEDPNSDW WVWVHDPENTAAGLVSGDLPENGPGYWNLY KNDHDLAEKLGVNTIRVGVEWSRIFPKPTFNV KVPVERDENGSIVHVDVDDKAVERLDELANK EAVNHYVEMYKDWVERGRKLILNLYHWPLPL WLHNPIIVIVRRMGPDRAPSGWLNEESVVEFAK YAAYIAWKMGELPVMWSTMNEPNVVYEQGY MFVKGGFPPGYLSFEAADKARRNMIQAHARA YDNIKRFSKKPVGLIYAFQWFELLEGPAEVFD KFKSSKLYYFTDIVSKGSSIINAEYRRDLANRL DWLGVNYYSRLVYKIVDDKPIILHGYGFLCTP GGISPAENPCSDFGWEVYPEGLYLLLKELYNR YGVDLIVTENGVSDSRDALRPAYLVSHVYSV WKAVNEGIPVKGYLHWSLTDNYEWAQGFRQ KFGLVMVDFKTKKRYLRPSALVFREIATHNGI PDELQHLTLIQ |
| SEQ ID No.: 14 | Cal-divirga maquil-ingensis | MIKFPSDFRFGFSTVGTQHEMGTPGSEFVSDW YVWLHDPENIASGLVSGDLPEHGPGYWDLYK QDHSIARDLGLDAAWITIEWRAVFPKPTFDVK VKVDEDDGGNVVDVEVNESALEELRRLADLN AVNHYRGILSDWKERGGLLVINLYHWAMPT WLHDPIAVRKNGPDRAPSGWLDKRSVIEFTKF AAFIAHELGDLADMWYTMNEPGVVITEGYLY VKSGFPPGYLDLNSLATAGKHLIEAHARAYDA IKAYSRKPVGLVYSFADYQPLRQGDEEAVKEA KGLDYSFFDAPIKGELMGVTRDDLKGRLDWIG VNYYTRAVLRRRQDAGRASVAVVDGFGYSCE PGGVSNDRPCPDFGWEIYPEGVYNVLMDLW RRYRIVIPMYITENGIADEHDKWRSWFIVSHLY QIHRAMEEGVDVRGYFHWNLIDNLEWAAGY RMRFGLVYVDYATKRRYFRPSALVMREVAKQ KAIPDYLEHYIKPPRIE |

TABLE 1-continued

| Sequence ID number | Species | Amino Acid sequence |
|---|---|---|
| SEQ ID No.: 15 | Pyrococcus furiosus | PLKFPEEFLFGTATAAHQIEGDNKWNDWWYY EQIGKLPYKSGKACNHWEFYKEDIQLMASLG YNAYRFSIEWSRLFPEENKFNEEAFNRYQEIID LLLANNITPLVTLHHFTSPLWFMKKGGFLREE NLKFWEKYVEKVAELLEKVKLIATFNEPMVY VMMGYLTAYWPPFIKSPFKAFKVASNLLKAH ALAYEILHGKFQVGIVKNVPIMLPATDKERDK KAAERADNLENWYELDAIWSGVYRGAFKAYR VPQSDADFIGINYYTASEVRHSWNPLKFFEDA KLADVSERKTQMGWSVYPRGIYIALKKASKY GKPLYITENGIATLDDEWRIEFIIQHLQYVH KAIEDGLDVRGYFYWSFMDNYEWREGFEPRF GLVEVDYETFERRPRKSAYIYGGIAKSKEIK DEILEKYGLSSL |
| SEQ ID No.: 16 | Pyrococcus horikoshii | PLKFPEMFLFGTATSSSHQIEGNNRWNDWWYY EQIGKLPYRSGKACNHWELYRDDIQLMTSLGY NAYRFSIEWSRLFPEENKFNEDAFMKYREIIDL LLTRGITPLVTLHHFTSPLWFMKKGGFLREENL KHWEKYIEKVAELLEKVKLVATFNEPMVYM MGYLTAYWPPFIRSPFKAFKVAANLLKAHAIA YELLHGKFKVGIVKNIPIILPASDKERDRKAAE KADNLFNWHFLDAISWGKVYRGVFKTYRIPQS DADEIGVNYYTASEVRHTWNPLKFFFEVKLAD ISERKTQMGWSVYPKGIYMALKKASRYGRPL YITENGIATLDDEWRVEFIIQHLQYVHKAIEDG LDVRGYFYWSFMDNYEWKEGFGPRFGLVEV DYQTFERRPRKSAYVYGEIARSKEIKDELLKR YGLPELQL |
| SEQ ID No.: 17 | Thermococcus litoralis | FPEKFLFGTSTAAHQVEGDNRWNDWWYYEEI GKLPYKSGKACNHWGLYREDIELMAQLGYNA YRFSIEWSRLFPEEGKFNEDAFNRYREII ELLLLEKGITPNVTLHHFTSPLWFMRKGGFL KEENLKYWEKYVDKAAELLKGVKLVATFNE PMVYVMMGYLTAYWPPFVKSPFKAFKVAAN LLKAHAMAYDILHGNFDVGIVKNIPIMLPAS NREKDIKAAQKADNLENWNELDAIWSGKYKG AFGTYKTPESDVDFIGINYYTASEVRHSWNP LKFFFDAKLADLSERKTDMGWSVYPKGIYEA IAKVSRYGKPMYITENGIATLEDEWRIEFII QHLQYVHKALNDGFDLRGYFYWSEMDNYEWA EGFRPREGLVEVDYTTFERRPRKSGYVYGEI AREKKIKDELLAKYGLPEL |
| SEQ ID No.: 18 | Thermococcus sibiricus | NAVIVFPKSFLFGTATSSHQIEGNNKWNDWW YYEQIGKLPYKSGKACNHWELYKEDISLMHSL GYDGYRFSIEWSRIFPKENEIDENALN RYLEIIELLVKSGITPNVTLHHFTSPIWFMQR GGFAKEENLKYWEQYVETVAGILKDVKLVATF NEPMVYVMMGYLTAYWPPFVKSPFKAFKVAAN LLKAHALAYEILSSRLKVGIVKNIPIMLAASY MERDKKAAEKADNLFNWNFLDAIWSGKLKGVL STYTVPESDVDFIGVNYYTASEVKYSWNPIKF FFEAKLADLSERKTQMGWSVYPEGIYKAITAV SRYEKPMYITENGIATLDDEWRKEFVVQHLQY VQKAIDEGYDVRGYFYWSFMDNYEWKEGFEPR FGLIEIDYKTYERKPRESAYVYGEIAQKKEIS EELIKKYGLKGL |
| SEQ ID No.: 19 | Termococcus kodakarensis | MLSMFPEKFLFGTSTAAHQVEGDNKWNDWW YYEEMGKLPYKSGKACNHWELYREDIELMAE LGYNAYRFSIEWSRLFPEEGKFNEDAFNRYREI IELLLEKGITPNVTLHHFTSPLWFMRKGGFLKE ENLKYWEGYVDKAAELLKGVKLVATFNEPLV YVTMGYLTAYWPPFIKSPFKSFRVAANLLKAH AIAYELLHGKFQVGIVKHIRVMLPERKGDEKA AQKADNLFNWYFLDAIWSGKYRGAFKTYSVP ESDADFIGVNYYTASTVRRSLNPLKMFFEAKD AEIGERRTQMGWSVYPEGVYLALRRASEYGR PLYVTENGIATLDDEWRKEFIIQHLRQVLRAIE DGLDVRGYFYWSLMDNYEWREGFEPRFGLIE VDFETFERRPRGSAYLYGEIARTKKLPGEEDP |
| SEQ ID No.: 20 | Acidulprofundum boonei | MLKFPPNFIFGTATAGHQIEGDNVNSDWWHY ENMGKLPYKSGKTCNHWNLYRQDIELMQSLG YNAYRFSIEWARIFPKEGKIDKKALQRYREIIN LLNKKGIIPMVTLHHFTLPLWFLEKGGFAKEE NLKYWEDYVKALKDILNLKLIATFNEPMVYV VAGYLSGEWPPFKKAPRIASRVAANILKAHAI AYEILHKEHEVGIVKNIPIFLSASRRNDDLKAA RRADNMFNFAFLDVIWNGEYKGIIGKYEVPVS DLDFIGVNYYTAYKVRHSYNPLKFFLDAKPAE MGERRTDMGWSVYPEGIYKAVEKISRYKKPIY ITENGIATRDDEWRISFIIQHLQYLYRAI KYGYNVKGYFYWSFMDNFEWDKGFAPRFGLVE INYENFQRKPRRSAYVYGEISKTKKIKDEVLE KYGES |
| SEQ ID No.: 21 | Thermococcus barophilus | MLKFPDHFIFGTATSSYQIEGDNIWSDWWYW AEKGRLPKAGKACNHWELYKEDIELMASLNY PAYRLSVEWARIFPEEGKLNESALERYQDIIDL LNKKGITPMLTVHHFTLPMWFALKGGFEKDE NLKYWEEYVSVIAELKGVELVATFNEPMVYV VAGYLMGMWPPFKKNPPKAGKVAANLINAH AIAYEILHGRFKVGIVKNYQHFIPATNSKRDKE ARDRVDYLFNWAFIDGIFHGSYESFMKKYKV NESDLDFIGINYYNIQKVKKSWNPLNPFIVEDA SVSRKTDMGWSVYPKGIYEGIKAFSRYERPMY ITENGIATLDDGWRIEFIIQHLQYVH KAIREDLDINGYFYWSLMDNYEWAEGFRPRFGL VEIDYETFERKPRKSAYVYGEIAKRKEISNELL EKYGLREL |
| No.: 22 | Thermococcus alcaliphilus | MIVFPEFFLFGTATSSHQIEGDNKWNDWWYY EEIGKLPYKSGKACNHWELYREDIELMAQLGY NAYRFSIEWSRLFPEEGKFNEEAFN RYREIIEILLEKGITPNVTLHHFTSPLWFMRK GGFLKEENLKYWEQYVDKAAELLKGVKLVATF NEPMVYVMMGYLTAYWPPFIKSPFKAFKVAAN LLKAHAMAYDILHGNFDVGIVKNIPIMLPASN REKDVEAAQKADNLFNWNFLDAIWSGKYKGAF GTYKTPESDADFIGINYYTASEVRHSWNPLKF FFDAKLADLSERKTDMGWSVYPKGIYEAIAKV SHYGKPMYITENGIATLDDEWRIEFIIQHLQY VHKALNDGFDLRGYFYWSFMDNFEWAEGFRPR FGLVEVDYTTFKRRPRKSAYIYGEIAREKKIK DELLAKYGLPEL |

Additional thermophylic □-glucosidases as disclosed in U.S. Pat. No. 6,960,454, which is incorporated by reference in its entirety, can be used directly in the present invention or can used as starting point for further optimzation using methods provided herein.

B. Developing a Variant Steryl Glycosidase

In some embodiments, an identified enzyme with steryl glycosidase activity is used as a basis for generating a mutant enzyme with increased activity, such with greater catalytic efficiency, or stability, including but not limited to thermostability. In some embodiments, an identified enzyme or variant enzyme is modified to increase activity or stability, such as by post-translational modification. In some embodiments, the variant has an epigenetic difference from the original strain. In some embodiments, the variant is a mutant, e.g. the variant contains a mutation in the gene encoding the steryl glycosidase. A gene refers to a deoxyribonucleotide (DNA) sequence that encodes a polypeptide, such as a template steryl glycosidase. DNA can be natural, artificial, or a combination of both.

In some embodiments, the mutant enzyme may be generated by targeted mutation. In some embodiments, the mutations may be determined based on structural information about the enzyme or its homologs. For example, the enzyme can be rendered more stable under higher heat conditions by using cysteine mutations to create stabilizing disulfide bridges. In some embodiments, stabilizing mutations can be based on increasing charged or hydrophobic interactions between residues. In some embodiments, catalytic activity can be increased by mutations that affect the active site of the enzyme. Such mutations can, for example, be based on increasing homology to another, more active enzyme. In some embodiments, the mutant enzyme can be truncated, for example to remove an inhibitory domain. In some embodiments, the mutant enzyme can be a fusion protein, such as by fusion to a polypeptide, including but not limited to whole or partial proteins or domains or short peptide sequences.

In some embodiments, the variant enzyme is generated by random mutation, followed by selection for the desired activity. In some embodiments, the variant enzyme is generated by directed evolution. Directed evolution generally consists of producing a population of variants around a template or starting sequence, then choosing variants with a desired property, such as steryl glycosidase activity, lipase activity, and/or thermostability.

In some embodiments, a gene encoding a previously identified enzyme is used as a template for directed evolution. The template gene may be used to generate mutated copies. Methods suitable for generating mutated copies include but are not limited to error-prone replication, targeted mutagenesis, or oligonucleotide directed mutagenesis.

In some embodiments, the genes are inserted into vectors under control of a promoter. In some embodiments, the promoter is used to control expression of a variant gene encoding the steryl glycosidase or lipase. Promoters for use with the invention may be, for example, inducible or constitutively active. By "inducible" is meant that promoter activity can be controlled by an inducing agent, such as a compound, peptide, ion, or other additive. Inducing agents include but are not limited to organic agents; inorganic agents; alcohols; neurotransmitters; antibiotics; peptides; carbohydrates; nucleic acids; hormones; drugs; light; toxins; and temperature. In some embodiments, inducible promoters are activated by an activator. In some embodiments, inducible promoters are repressed by a repressor.

In some embodiments, the inducible promoter is a switch, e.g. either active or silenced depending on whether an inducing agent is present. In some embodiments, the inducible promoter is tunable, e.g. the level of promoter activity varies based on the amount of inducing agent that is present. In some embodiments, the promoter is linearly tunable. A tunable promoter can control enzyme expression based on the concentration of inducing agent added to the screening medium, which is useful for controlling the degree of selection pressure as described herein.

Examples of promoters suitable for use in the invention include but are not limited to copper-inducible promoters and beta-estradiol dependent expression system (UAS-GAL10/GEV).

Transformation

In some embodiments, mutated copies of the template gene may be transformed into host cells. Host cells of the present invention can be of different types and from different organisms, which include, but are not limited to, bacteria, fungi (e.g. yeast), algae, plants, and animals. In some embodiments, the cell is a microorganism, such as yeast or microalgae. In some embodiments, the cells are yeast cells, including but not limited to Saccharomyces cerevisiae, Saccharomyces boulardi, Pichia pastoris, Hansenula polymorpha and Schizosaccharomyces pombe. Host cells comprising any of the variant genes of the invention can form separate strains. Strains are, for example, clonal strains, e.g. isolated from an individual colony, or non-clonal, e.g. derived from a liquid culture sample.

Transformation can be performed by any method known in the art, including but not limited to electroporation, chemical transformation, transfection, use of a Ti plasmid, particle bombardment, transduction, or use of infectious agents. Methods of modifying gene expression or introducing one or more exogenous genes into a cell are known in the art. For example, methods of stably transforming cells and compositions comprising isolated nucleic acids of use are well known in the art and any such methods and compositions may be used in the practice of the present invention. Exemplary transformation methods of use may include microprojectile bombardment, electroporation, protoplast fusion, PEG-mediated transformation, DNA-coated silicon carbide whiskers or use of viral mediated transformation (see, e.g., Sanford et al., 1993, Meth. Enzymol. 217:483-509; Dunahay et al., 1997, Meth. Molec. Biol. 62:503-9; U.S. Pat. Nos. 5,270,175; 5,661,017). The method used can vary with the type or species of host cell. For example, particle bombardment may be more suitable for crossing through cell walls of plant cells.

In some embodiments, one or more exogenous genes are introduced into the host cells using a vector. In general, the vector comprises the nucleotide sequences encoding the exogenous gene and the regulatory elements necessary for the transformation and/or expression of gene in the host cell, such as the promoter sequences provided herein. In some embodiments, vectors are selected to optimize expression in the host cells used. For example, yeast expression vector YES2 can be used to express the genes in yeast host cells. In some embodiments, the vectors of the present invention comprise a backbone sequence. In some embodiments, the vectors of the present invention comprise a multiple cloning site, one or more regulatory elements to control the expression of the insert gene, as well as one or more markers for selection. Markers included are paromomycin resistance (Sizova et al., Gene 181:13-8 (1996)) and hygromycin B resistance (Berthold et al., Protist 153:401-12 (2002).

In some embodiments, one or more exogenous genes are integrated into the genome of the host cells. In some embodiments, a vector containing an exogenous gene is introduced into the host cell, and the exogenous gene subsequently integrated into the host cell's genome. In some embodiments, homologous recombination is used for integration. In other embodiments, site-specific recombination is used, including but not limited to methods such as Cre-Lox recombination. In some embodiments, a retroviral or transposon-based system is used.

In some embodiments, mutated genes are generated in a host cell. Methods for generating such a variant population include but are not limited to inducing mutations in host cells containing the template gene, such as growing the host cells in a mutation-inducing environment. Mutation-inducing environments include but are not limited to UV radiation or treatment with mutagens, such as methylmethane sulphonate (MMS). Many other methods for generating a population of mutant genes are known in the art and are usable with the invention.

Generating mutations in the host cell may be advantageous because it does not require a transformation step before initial screening. However, generating random mutations in the host cell genome may also cause mutations in other genes, which may cause phenotypic effects that affect the screening process. In some embodiments, a gene encoding the target steryl glycosidase or lipase is isolated from a mutated host cell. In some embodiments, the gene is isolated from the mutated host cell before screening. In some embodiments, the gene is then transformed into one or more other host cells for screening in a consistent genetic background. In some embodiments, the gene is isolated from the mutated host cell after screening. In some embodiments, the isolated gene is tested for mutations, such as by single nucleotide polymorphism (SNP) detection, restriction analysis, or sequencing. In some embodiments, the gene is not isolated from a mutated host cell.

Screening

In some embodiments, after generating a population of variants, variants with the desired property are chosen by screening or selection methods, such as by positive selection. The number of investigated mutants is typically very large, up to $10^{11}$.

In some embodiments, the host cell used for screening is a yeast cell. In some embodiments, the host cell is an auxotrophic yeast cell that is unable to synthesize ergosterol, such as DY1457 Δhem1 (Crisp et al, J. BIol. Chem 278: 45499-45506). Ergosterol is a natural sterol that is a component of the yeast envelope. In the absence of an external source of sterols, such auxotrophic yeast cells are unable to form colonies.

In some embodiments, auxotrophic yeast cells are plated on a medium containing steryl glycoside. For example, to test for a steryl glycosidase, ergosterol glucoside can be included in the medium. Some amount of inducer is also included to stimulate expression of the variant steryl glycosidase gene. The lower the amount of inducer, the more selective the method will be. Only host cells expressing a steryl glycosidase with sufficient activity to digest steryl glycoside into a viable amount of sterols will form colonies. In some embodiments, cells from successful colonies are isolated, used for subsequent rounds of directed evolution, and/or used to produce enzyme for treating biodiesel. In some embodiments, steryl glycosidase genes from successful colonies are also isolated for analysis, sequencing, transformation into another type of host cell, or used for subsequent rounds of directed evolution.

In some embodiments, the auxotrophic host cells are grown at a specific temperature to select for enzyme thermostability. In some embodiments, the host cells are grown at or above about 45° C., at or above about 50° C., at or above 55° C., at or above 60° C., at or above 65° C., at or above 70° C., at or above 75° C., at or above 80° C., at or above 85° C., at or above 90° C., or at or above 95° C.

Corresponding lipid auxotroph mutants, supplemental nutrients, and inducer levels as would be known to one of skill in the art may be used to select for variant lipases.

In some embodiments, the mutation and selection steps are repeated multiple times. In some embodiments, the subsequent selection step is performed with decreasing amounts of promoter activator, which allows each round of directed evolution to gradually increase enzyme activity. In some embodiments, the selection step is performed with increasing amounts of a promoter inhibitor. In some embodiments, subsequent selection steps are performed at increasing temperatures to gradually increase selective pressure for high thermostability. In other embodiments, the initial screening is performed with a low level of ergosterol or other corresponding essential nutrient, and subsequent screening rounds are performed with decreasing levels of the essential nutrient. This screening method is more suitable for use when the starting enzyme is relatively inefficient.

In some embodiments, between each round of selection, the variant gene is placed under the control of a weaker promoter. In these embodiments, the promoters can be inducible or constitutive. In one example, the initial selection step is performed while the variant gene is under the control of a strong promoter. In a subsequent selection step, the variant gene or a variant thereof is under the control of a medium promoter. In a still later selection step, the variant gene or a variant thereof is under the control of a weak promoter.

Exemplary strong promoters include promoters from the following genes: Photosystem II stability/assembly factor, Peptidyl-Prolyl cis-trans isomerase, histidinol dehydrogenase, malate dehydrogenase (NAD+) (Mdh2), and LHC (LhcII-1.3).

Exemplary medium promoters are the promoters from the following genes: Formate Nitrite transporter, ATP-dependent CLP protease proteolytic subunit, serine carboxypeptidase I, and 40S ribosomal protein S19.

An exemplary weak promoter is the promoter from the following gene: sterol-C-methyltransferase Erg6 like protein.

Similar methods as would be obvious to one of skill in the art can be used to select for lipases or phospholipases with greater activity or thermostability.

C. Enzyme Production

Enzymes can be produced by small-scale methods, large-scale methods, industrial methods, or any other methods known in the art. In some embodiments, the sequence of the gene encoding the enzyme is a sequence known in the public domain, specifically the sequence that codes for the protein sequences provided herein (e.g. in Table 1). In some embodiments, the sequence is a sequence that is obtained by codon optimization. In some embodiments, the gene sequence is isolated from a screened colony as described herein, or is designed to encode such a protein.

In some embodiments, the enzyme is produced by in vitro translation. In some embodiments, the enzyme is chemically synthesized. In some embodiments, the enzyme is expressed in a host cell. Synthetic or isolated genes expressing an steryl glycosidase of the invention can be transformed into and expressed in suitable host cells, including, but are not limiting to bacteria (e.g. E. coli), yeast, algae, filamentous fungi, plant, and mammalian cells.

In some embodiments, genes encoding the enzymes are optimized for expression in the host cell, for example by designing and synthesizing codon optimized sequences encoding the polypeptides. A summary of codon usage of C. reinhardtii is provided in Mayfield and Kindle, PNAS (1990) 87:2987-2991. Additional codon usage for different organisms are available at the Codon Usage Database (web address: www.kazusa.orjp/codon/).

In some embodiments, the cells produce both the raw materials for generating biofuels and a variant enzyme of the invention. Host cells can be heterologous or homologous to the source of the original gene. In some embodiments, the host cells have normal or near-normal growth rates. In some embodiments, the variant gene is controlled by an inducible promoter, and the genetically engineered cells have a normal or near-normal growth rate while the promoter is not active.

In some embodiments, the variant gene is integrated into the host cell's genome in a location under the control of an endogenous promoter. In some embodiments, the variant gene is on a vector or integrated in the host cell's genome along with an exogenous promoter sequence.

In some embodiments, the expression of the transformed gene in the host cell is stable. By "stable expression" herein is meant that the transformed gene is retained in the host cell for at least 5, 10, 20, 50, 100, 200, 300, 400, or 500 generations, and being transcribed into RNA and/or expresses the protein it encodes. In general, a stable transformed gene is retained in the host cell for at least 1, 2 3, 4, 5, 10, 15, 20 or 25 days, or for at least 1, 2, 3, 4, 5, 6, 7, 8, 9, 10, 11, or 12 months, and being transcribed into RNA and/or expresses the protein it encodes. In some embodiments, stable expression is in the presence of a promoter activator. Cells that do not express the transformed gene but retain the ability to express the gene such as in the presence of sufficient amounts of activator, are included as stably expressing cells. In some embodiments, the cells are stored, for example as a frozen stock for at least 0.1, 1, 2, 3, 4, 5, 6, 7, 8, 9, 10, 11, or 12 months.

Expression includes constitutive or inducible expression. In some embodiments, the gene encoding a recombinant enzyme is under the control of an inducible promoter, including but not limited to promoters that can be activated by IPTG or $Cu^{2+}$. The host cell containing the inducible enzyme may be grown in liquid culture, in the absence of activators, until the host cell population is undergoing exponential growth. In bacterial host cells, the exponential growth phase is typically determined by light absorbance of 0.6-0.8 O.D. at 600 nm. The activator is then added to the liquid culture to induce expression of the enzyme. After several hours, the cells are harvested and typically lysed to release the enzyme. In some embodiments, protease inhibitors, reducing agents, or other additives are added to the lysed cells to preserve enzymatic activity.

In some embodiments, the gene encoding the recombinant enzyme is under the control of a constitutive promoter. In some embodiments, the promoter is a strong promoter. In these embodiments, cells can be directly lysed to release enzyme, without any induction step.

In some embodiments, the present invention describes production facilities to be used in large-scale enzyme production. In some embodiments, the facilities use yeast, bacteria, or algae cells that express the variant enzyme. In embodiments where yeast or bacteria are used to produce the enzymes, methods of growing the yeast and bacteria include fermenters, such as industrial-scale fermenters.

In embodiments where algae is used to produce the enzymes, methods of growing the algae include but are not limited to open raceway ponds, also known as high rate ponds (HRPs), or enclosed growth vessels, also known as photobioreactors (PBRs). Some examples of PBRs include transparent plastic bags or plastic tubes with pumps to promote circulation.

In some embodiments, expressed enzymes are used without substantial isolation, or without substantial purification from the host cells. In some embodiments, expressed enzymes are isolated from host cells. Isolated enzymes refer to enzymes that are substantially free of at least one component of the host cell. In some embodiments, isolated enzymes are further purified, for example to at least 50% purity, at least 60% purity, at least 75% purity, at least 80% purity, at least 90% purity, at least 95% purity, at least 98% purity, or about 100% purity. Purity refers to the total amount of enzyme in the composition by mass or molarity.

In some embodiments, isolated enzymes are further formulated for storage or for use in treating biodiesels or their oil precursors. Formulation steps include but are not limited to adding cofactors, chaperones, or other additives, performing post-translational modification of the enzyme, or adding preservatives such as protease inhibitors or reducing agents.

D. Using Enzymes

The enzymes of the invention are suitable for use in reducing the amount of steryl glycosides in a sample. Methods for using the enzymes are also encompassed by the invention. Methods for using the enzymes generally comprise generating a reaction mixture comprising the enzyme and a sample comprising some amount of steryl glycosides.

Figure 2:
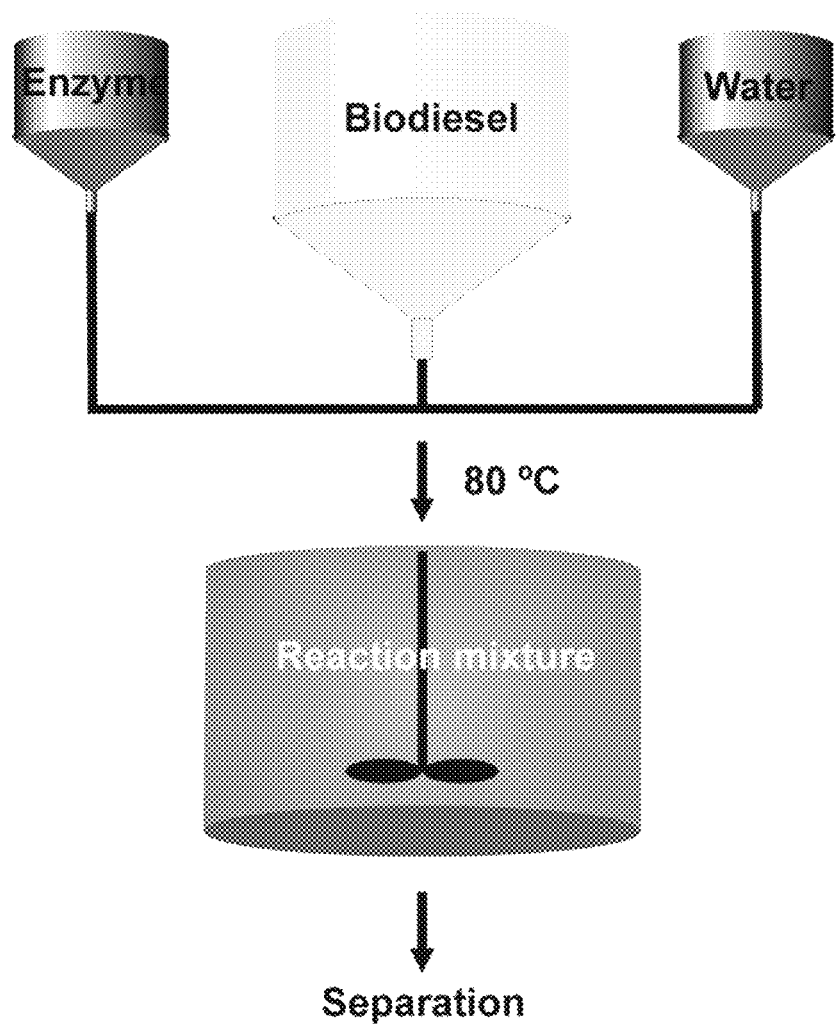
FIG. 2 is a schematic depicting an example process of enzymatic removal of steryl glycosides from biodiesel.

In some embodiments, the method comprises the following steps: (i) adding a steryl glycosidase to biodiesel or oil sample with some amount of water, (ii) agitating the mixture at given temperature and shear rate for a period of time and (iii) separating the biodiesel or oil free of steryl glycosides. A schematic of an example procedure is illustrated in FIG. 2. In some embodiments, the steryl glycosidase is attached to a solid substrate. In some embodiments, the steryl glycosidase is attached to a bead or resin that is mixed with the sample, which allows for easier removal of the enzyme after the reaction is complete. In other embodiments, the resin-bound steryl glycosidase is packed into a column, and the sample flows through the column. In some embodiments, the steryl glycosidase is attached to a surface, such as the sides of a reaction vat or to a filter, and the sample allowed to flow across or through the surface.

In some embodiments, the steryl glycosidase is not isolated from the cell or cell lysate before use. For example, in some embodiments where the host cell produces both a biofuel precursor and the recombinant enzyme, the steryl glycosidase reaction is performed directly in the cell or cell lysate. In some embodiments, such host cells secrete or excrete biofuel precursor that has already been treated by the steryl glycosidase. In other embodiments, the host cells are lysed to free the biofuel precursor.

In some embodiments, host cells expressing the enzyme can secrete or excrete the enzyme. In some embodiments, the enzyme can be present on the external surface of the cell. In some embodiments, the host cell is placed in a reaction container or on a reaction surface, and the sample is introduced to the container or surface. In one example, host cells expressing the enzyme are placed in a cylinder, and the biodiesel or biodiesel precursor is forced to flow through the cylinder.

In some embodiments, water comprises at least 0.1%, 0.2%, 0.3%, 0.4%, 0.5%, 0.6%, 0.7%, 0.8%, 0.9%, 1%, 1.5%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30% by weight of the reaction mixture. In some embodiments, water comprises about 0.1% to about 15%, about 0.5% to about 15%, about 1% to about 15%, about 7% to about 15%, about 10% to about 15%, about 0.1% to about 10%, about 0.5% to about 10%, about 1% to about 10%, about 0.1% to about 5%, about 0.5% to about 5%, about 1% to about 5%, or about 0.1% to about 3% by weight of the reaction mixture. Without being bound by any theory, water is used in enzymatic hydrolysis of molecules.

In some embodiments, methanol comprises at least 0.1%, 0.2%, 0.3%, 0.4%, 0.5%, 0.6%, 0.7%, 0.8%, 0.9%, 1%, 1.5%, 2%, 3%, 4%, 5%, 6%, 7%, 8%, 9%, or 10% by weight of the reaction mixture. In some embodiments, methanol is present as a carryover of the transesterification process in biodiesel.

In some embodiments, the method comprises further adding other enzymes. In some embodiments, a lipase or phospholipase is added to reduce the amounts of SMGs. In some embodiments, the lipase or phospholipase reaction occurs simultaneously with the glycosidase reaction. In some embodiments, the method uses a lipase or phospholipase without using a steryl glycosidase. In some embodiments, the method uses more than one steryl glycosidase, lipase, and/or phospholipase. In some embodiments, an acyltransferase is use with or in place of a steryl glycosidase. An acyltransferase acylates a nonacylated steryl glycoside to form an acylated steryl glycoside, which is more soluble than nonacylated steryl glycosides. In some embodiments, another enzyme or additive is added to facilitate the reaction(s) or otherwise treat the biodiesel or biodiesel precursor. In some embodiments, enzymes or catalysts responsible for the transesterification reaction are added. In some embodiments, additives such as emulsificants or cofactors are added. In some embodiments, such enzymes or additives are thermostable.

Enzymatic reactions of the invention are conducted under conditions suitable for enzyme activity, optionally with mixing. In some embodiments, the reactions are conducted at a temperature between about 50° C. and about 110° C. In some embodiments, the reaction are conducted at temperatures above about 50° C., above about 55° C., above about 60° C., above about 65° C., above about 70° C., above about 75° C., above about 80° C., above about 85° C., above about 90° C., above about 95° C., or above about 100° C. In some embodiments, the reaction is performed at about 80° C. or higher. Other appropriate temperatures may be selected based on the specific enzyme used, such as based on the peak activity of a thermostable or thermophilic enzyme. In some embodiments, the reaction occurs over at more than one temperature over the course of the reaction, such as over a range of temperatures.

Agitation of the reaction can be performed at any acceptable shear rate. In some embodiments, the shear rate is vigorous enough to allow full circulation of the liquid in the mixing vat. In some embodiments, the shear rate is between 10 and 5000 $s^{-1}$.

The reaction can be performed for any duration suitable for reducing the amount of steryl glycosides in the sample. The reaction time may depend on a variety of factors, including but not limited to the composition or volume of the sample to be treated, the viscosity of the sample, the rate of mixing, the amount of steryl glycosides to be digested, the temperature, and the amount or activity of the enzyme used. As some non-limiting examples, the reaction can be performed for at least 10, 15, 20, 25, or 30 minutes, at least 1 hour, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 16 hours, at least 20 hours, at least 24 hours, or for more than 24 hours. Similarly, the sample volume, the rate of mixing, the amount of enzyme, and the temperature used in the reaction may depend on any of the factors listed herein, including the length of the reaction. In some embodiments, the pH of the reactions is between about 3.0 and 8.0, such as between about 4.0 and about 7.6, between 5.0 and 7.0, or about pH 7.5.

In some embodiments, treatment with a steryl glycosidase, including but not limited to a thermostable steryl glycosidase, occurs before, during, and/or after the transesterification reaction. In some embodiments, a steryl glycosidase is added to a suitable biodiesel precursor at the same time as a catalyst used for transesterification.

In some embodiments, there is less steryl glycoside after steryl glycosidase treatment compared with untreated biodiesel or biodiesel precursor. Steryl glycosidase treatment can reduce the amount of a steryl glycoside in the biodiesel or biodiesel precursor by at least 5%, 10%, 15%, 20%, 25%, 30%, 35%, 40%, 45%, 50%, 55%, 60%, 65%, 70%, 75%, 80%, 85%, 90%, 95%, or by about 100%. When referring to "reducing" or a "reduction" of the amount of steryl glycoside in an oil or fat (e.g. a biofuel substrate) or a biofuel—the term "reducing" or "reduction" means in comparison to a comparable oil or fat (e.g. biofuel substrate) or biofuel which is the same as the claimed biofuel substrate or biofuel except that no enzyme(s) in accordance with the present invention have been added.

In some embodiments, after treatment, the concentration of steryl glycosides is less than 100 ppm, less than 90 ppm, less than 80 ppm, less than 70 ppm, less than 60 ppm, less than 50 ppm, less than 40 ppm, less than 30 ppm, less than 29 ppm, less than 28 ppm, less than 27 ppm, less than 26 ppm, less than 25 ppm, less than 24 ppm, less than 23 ppm, less than 22 ppm, less than 21 ppm, less than 20 ppm, less than 15 ppm, less than 10 ppm, or less than 5 ppm by weight.

In some embodiments, after treatment with steryl glycosidase, the resulting biodiesel or biodiesel precursor is collected for sale, storage, transport, or further processing or refining.

III. Biodiesel Production

Biodiesel production methods of the invention comprise producing biofuels from fatty acids or oils, and for enzymatic reduction of the amount of steryl glycosides in the biofuel.

The majority of biodiesel is produced by interesterification of triglycerides (e.g. oil and/or fats) with an alcohol, often in the presence of a catalyst, to form esters and glycerol. The catalyst is usually sodium or potassium hydroxide. As methanol and ethanol are the most commonly used alcohols in commercial biodiesel production, most commercially produced biodiesel comprises methyl or ethyl esters of fatty acids (called FAME and FAEE, respectively). However, longer chain alcohols may also be used. In some embodiments, the sample to be treated comprises a biofuel or biodiesel, such as FAME or FAEE. In some embodiments, the sample to be treated comprises a biofuel or biodiesel precursor.

In some embodiments, sample containing steryl glycosides, and at least one steryl glycosidase are combined in a reaction or mixing vat and mixed to form a reaction mixture, where enzymatic removal of steryl glycosides takes place. In some embodiments, other additives to enhance enzyme activity, enzyme thermostability, or steryl glycosides solubility are included in the reaction mixture. In some embodiments, a chaperone protein is added to enhance the enzyme's thermostability.

In some embodiments, such as that depicted in FIG. 2, water is also added to the reaction mixture. In some embodiments, water is included with the input material used to produce the biofuel. In some embodiments, water or other additives are removed from the biodiesel after the enzymatic reaction is complete. As some non-limiting examples, the reaction can be performed for at least 30 minutes, at least 1 hour, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 16 hours, at least 20 hours, at least 24 hours, or for more than 24 hours.

In some embodiments, the reaction is maintained at a set temperature. The set temperature can be determined based on the temperature-dependent activity of the steryl glycosidase. Non-limiting examples of suitable temperatures include temperatures at about or above 32° C., 37° C., 40°

C., 45° C., 50° C., 65° C., 70° C., 75° C., 80° C., 85° C., 90° C., 95° C., 98° C., 100° C., 105° C., 110° C., or 115° C.

In some embodiments, the concentration of steryl glycosidase is about 0.1-15 g/ton (gram of enzyme per ton of biodiesel.

In some embodiments, the reaction is carried out in the presence of proper additive, such as polyglycerol polyricinoleate (ADMUL™), and emulsificants, such as lecithin.

In some embodiments, waste heat, such as that produced from electrical generators, is used to maintain or help maintain the temperature of the reaction. In some embodiments, solar or geothermal heat is used to maintain or help maintain the temperature of the reaction.

In some embodiments, the chemical products resulting from the steryl glycosidase reaction are removed from the treated sample. In other embodiments, products resulting from the enzymatic reactions are not removed. In some embodiments, other methods for removing steryl glycosides or other precipitates, such as filtration, centrifugation or distillation, are also used. Some non-limiting examples of supplemental methods for removing steryl glycosides are described in PCT Publication Nos. WO2007/076163, WO2007/0175091, and WO2008/051984 herein incorporated by reference in its entirety. Such supplemental methods can be performed prior to, after, or during enzymatic methods of the invention. In some embodiments, filtration is performed on the biodiesel, such as using a filter with a molecular weight cut-off of less than 1,000,000 g/mol. In some embodiments, filter aids are used, such as adsorbents, boric acid, soap, sugars (including sucrose and glucose), salts such as sodium chloride, citric acid, magnesium silicate, clay, diatomaceous earth, lecithin, proteins, carbon, cellulose, silica hydrogel, or combinations thereof, to help remove steryl glycosides from the biodiesel. Filter aids tend to increase precipitation or aggregation of the steryl glycosides, which reduces the time needed to filter the entire mixture. In some embodiments, centrifugation is used to separate precipitates from the biodiesel. In some embodiments, filter aids are used to reduce the centrifugation time.

Biodiesel production systems of the invention can incorporate systems or system components of other biodiesel or biofuel production systems known in the art. In some embodiments, the biodiesel production system comprises a mixing vat for containing and/or mixing the reaction. In some embodiments, the biodiesel production system comprises a solid substrate to which the enzyme is attached. In some embodiments, the enzyme is bound to a filter and the enzymatic reaction occurs as sample flows through the filter. In some embodiments, the enzyme is attached to a bead or resin, such as in a column, and the enzymatic reaction occurs as sample flows through the resin. In some embodiments, the reaction occurs inside a host cell that produces both the sample and the enzyme. Examples of systems and methods for processing lipids into biofuel, can be found in the following patent publications, the entire contents of each of which are incorporated by reference herein: U.S. Patent Publication Nos. 2007/0010682, 2007/0131579, 2007/0135316, 2007/0135663, 2007/0135666, 2007/0135669, and 2007/0299291.

Biodiesels produced by the methods described herein can be used as an alternative fuel to petroleum diesel, or can be used as an additive in petroleum diesel. Often, a biodiesel/petroleum diesel blend comprises 20% biodiesel.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Example 1

Measuring Steryl Glycosidase Activity

Steryl glycosidase activity is measured as follows:
a) Prepare a stock solution of steryl glycoside by dissolving 10 milligrams (mg) of steryl glycoside in 1 milliliter (ml) of a 3:1 mixture of tetrahydrofuran:water.
b) Add the steryl glycoside to a final concentration of 100 microgram per milliliter (μg/ml) in 1 ml of a reaction mixture containing 50 millimolar (mM) Phosphate buffer pH 6.5 and 5 μg of steryl glycosidase in an Eppendorf tube.
c) Place the reaction mixture on a shaker incubator and incubate at 80° C. for 4 h.
d) Extract the reaction mixture with 1 ml of ethyl acetate and evaporate to dryness under vacuum.
e) Re-dissolve the sample in 10 microliter (μl) of ethyl acetate
f) Analyze by thin layer chromatography (TLC) the presence of free sterols, generated as a result of steryl glycoside hydrolysis after the enzymatic treatment, using Hexane: Methanol 85:15 as running buffer and develop with ρ-anisaldehyde
d) Alternatively, analyze 50 μl sample of the reaction mixture for the presence of glucose using an assay based on the Hexokinase/Glucose 6-P-dehydrogenase method: the glucose generated by steryl glycoside hydrolisis is converted by Hexokinase (or Glucokinase) into glucose 6-phosphate. Glucose 6-phosphate is further oxidized by Glucose 6-P dehydrogenase, simultaneously reducing NADP+ to NADPH. The NADPH generated is detected by fluorescence ($\lambda$ex: 338 nm, $\lambda$em: 461 nm) and allows detection of glucose levels below 1 ppm. The assay can be adapted to microplates scale and detected in a Synergy microplate reader.

Example 2

Identifying a Steryl Glycosidase
The following is an example of how to identify a steryl glycosidase:
a) Clone a putative steryl glycosidase gene into a pET28a *E. coli* expression vector.
b) Transform the resulting plasmids by chemical transformation into a BL21(DE3) *E. coli* strain.
c) Grow a colony of the recombinant clone on 100 ml of LB at 37° C. until cell density reaches an $OD_{600}$=0.6.
d) Add 0.5 mM IPTG to the culture, and incubate at 24° C. for 10 h.
e) Disrupt the *E. coli* cells broth with three cycles of compression/decompression at 1000 bar in an APV homogenizers.
f) Heat the resulting liquid to 80° C., incubate for 10 minutes and centrifuge until clarification to separate solid materials in a sharpless centrifuge at 5000 g.

g) Collect the supernatant and analyze for steryl glycosidase activity as described in Example 1.

Figure 4:
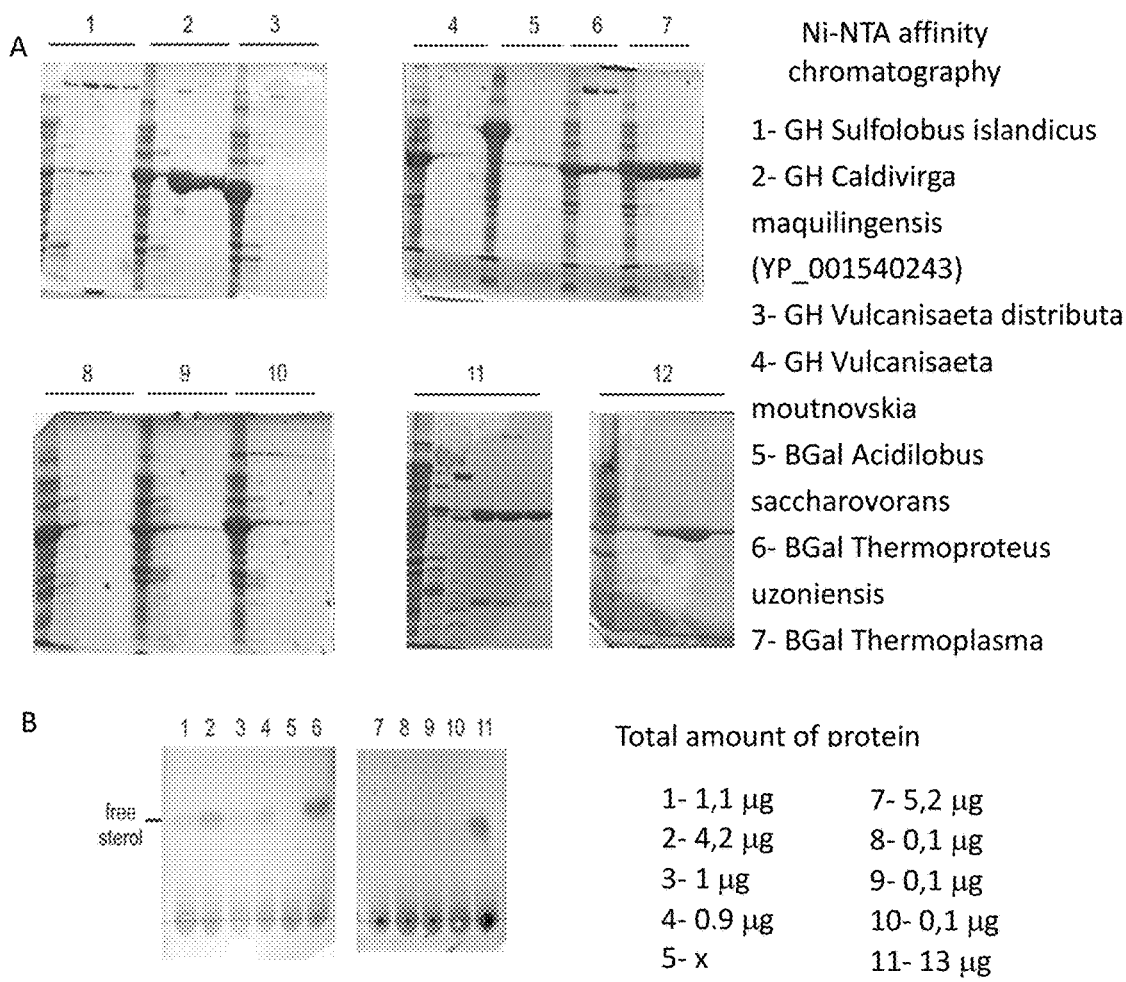
FIG. 4A is a collection of photographs depicting the expression of various example steryl glycosidase (SGase) genes in an *E. coli* host and the purification of expressed proteins via Ni-NTA (nickel-nitrilotriacetic acid) affinity chromatography.
FIG. 4B is a collection of photographs depicting the activity of an example SGase evaluated in aqueous media (5 hs incubation at 80° C., pH5.5 with 100 ppm SG).

Some of the example proteins listed in Table 1 were determined to be steryl glycosidases, as depicted in FIG. 4.

Example 3

Generating a More Active Steryl Glycosidase

The following is an example of how to generate a more active steryl glycosidase using directed evolution:
a) Create a library of mutated steryl glycosidase genes using error prone PCR.
b) Insert the library of mutated genes into a pCUP1 yeast expression vector, which is under the control of a promoter that is linearly inducible by $Cu^{2+}$.
c) Transform the resulting plasmids by chemical transformation into an auxotrophic yeast mutant cell unable to synthesize ergosterol, the natural sterol present in yeast envelope.
d) Plate the transformed cells onto a medium supplemented with steryl glycosides to a concentration of 20 mg/L and an initial concentration of the inducer of 100 micromolar (μM) $CuSO_4$.
e) Recover the steryl glycosidase gene from a resulting colony.
f) Use the steryl glycosidase for a new round of random mutagenesis and repeat the process described above in an iterative fashion. In each new selection, add a 10 μM lower concentration of the inducer to the medium.

Example 4

Large-scale Steryl Glycosidase Production

The following is an example of how to produce a thermostable steryl glycosidase in a large-scale:
a) A synthetic DNA encoding a codon optimized version of a gene encoding any protein listed in Table 1 is cloned into the NdeI-EcoRI sites of the pET24b plasmid (Novagen, USA).
b) The resulting plasmid is transformed by electroporation into the BL21(DE3) *E. coli* strain.
c) A colony of the recombinant one is grown on 100 ml of LB at 37° C. until cell density reaches an $OD_{600}=2$.
d) The culture obtained above is transferred to a seed fermentor containing 10 liters (L) of HM medium (described below) and grown for 10 h at 35° C.
e) The culture is transferred to a 1000 L fermentor containing 600 L of HM medium and grown at 35° C. until glucose exhaustion. An exponential feeding of a nutrient solution containing 600 g/L glucose and 15 g/L $MgSO_4$ is then initiated at a rate sufficient to maintain the specific grow rate at a value of $0.35\ h^{-1}\pm0.05$. When $OD_{600}$ reaches a value of 80, 1 mM IPTG is added and the nutrient solution is fed at a constant rate of 25±1 L/h for 10 h. Dissolved Oxygen concentration is kept at all time above 30% of saturation by enrichment of the air stream with pure oxygen when necessary. pH is maintained at 7 by the addition of $NH_4OH$.
f) At the end of the fermentation process, the broth is treated with three cycles of compression/decompression at 1000 bar in an APV homogenizers to disrupt the *E. coli* cells.
g) The resulting liquid is heated to 80° C., incubated for 10 minutes and centrifuged until clarification to separate solid materials in a sharpless centrifuge at 5000 g.
h) (NH4)2SO4 is added to 80% saturation to the clarified liquid, the mixture is incubated at 8° C. for 3 h and the centrifuged in a sharpless centrifuge at 5000 g to obtain a brown paste.
i) The obtained paste is air dried and the resulting powder contains a steryl glycosidase with a purity above 70% as determined by polyacrylamide gel electrophoresis (PAGE) analysis.

HM medium: Glucose 10 g/L, $Na_2HPO_4.7H2O$ 0.6 g/L, $KH_2PO_4$ 6 g/L, $K_2HPO_4$ 4 g/L, $(NH_4)_2\ HPO_4$ 3 g/L, $SO_4Mg.7H_2O$ 2 g/L, and 1 mL/L of trace element solution containing (in g/L): $SO_4Fe$ 10, $ZnSO4.7H_2O$ 2.5, $CuSO4.5H_2O$ 1, $MnSO4.5H_2O$ 1, $Na_2B_4O_7.10H_2O$ 0.2, $CaCl_2.2H_2O$ 5, $NaMoO_4.2H_2O$ 1, $CoCl_2.6H_2O$ 1; dissolved in 5 M HCl.

Example 5

Using Steryl Glycosidase to Remove Steryl Glycosides from a Biodiesel Mixture

The following is an example of how to use a steryl glycosidase to remove steryl glycosides from a biodiesel mixture:
a) A 42.5 ml distilled biodiesel sample containing 100 ppm of steryl glycosides is mixed with 7.5 ml of a water solution containing 50 mM Phosphate buffer pH 6.5 and 300 μg of steryl glycosidase. Alternatively, 5% of the emulsifier polyglycerol polyricinoleate (ADMUL™) is added to the reaction mixture.
b) Transfer the mixture into a 50 ml vessel and incubate in a heating block with a magnetic stirrer for 4 h at 80° C., accompanied by stirring.
c) While the reaction takes place, take 1 ml samples every hour, separate the aqueous phase and analyze for the presence of glucose as described in the Example 1.
d) After the reaction ends, separate the aqueous and organic phases and analyze for the presence of glucose in the aqueous phase as described in the Example 1, and for the SG consumption by GC-FID detection in the organic phase as described elsewhere (J. Food Lipids 12 (2005) 124-140).

Figure 5:
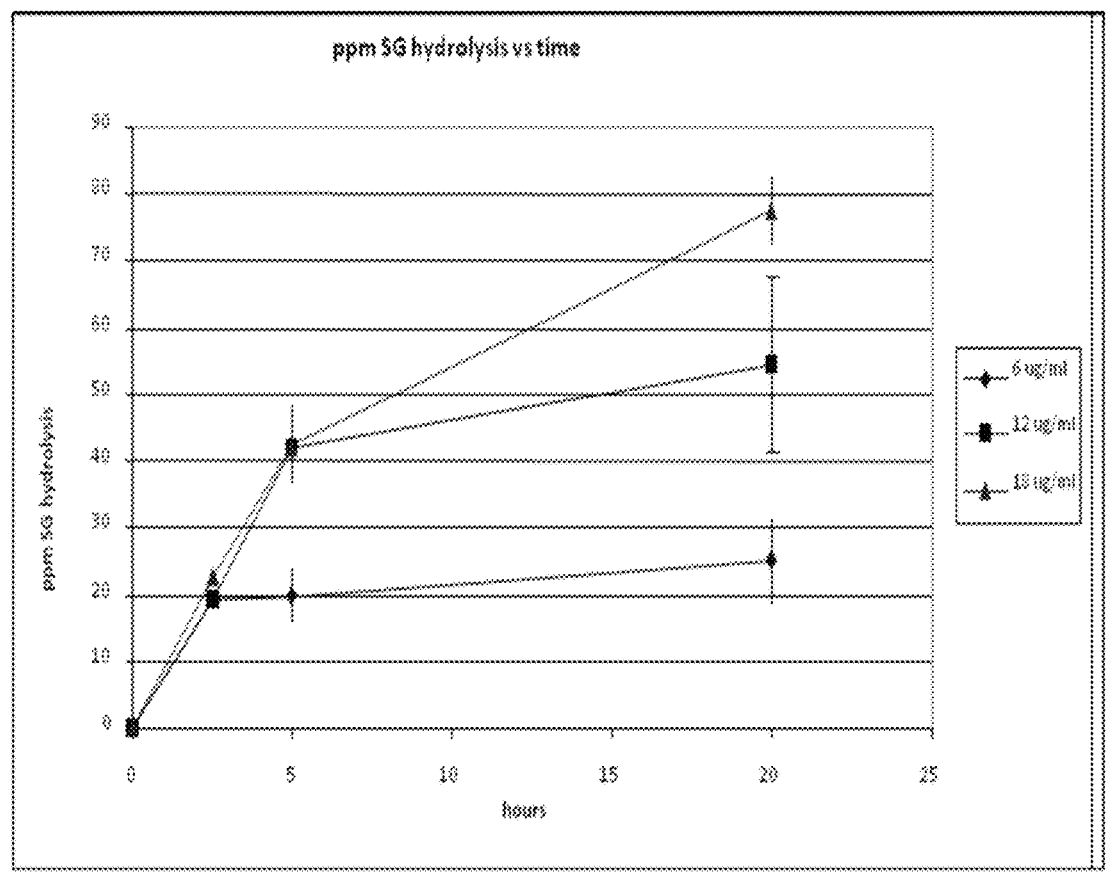
FIG. 5 is a graph depciting SG hydrolysis in Biodiesel/water emulsions (5% ADMUL) using an example SGase, LacS.
Figure 6:
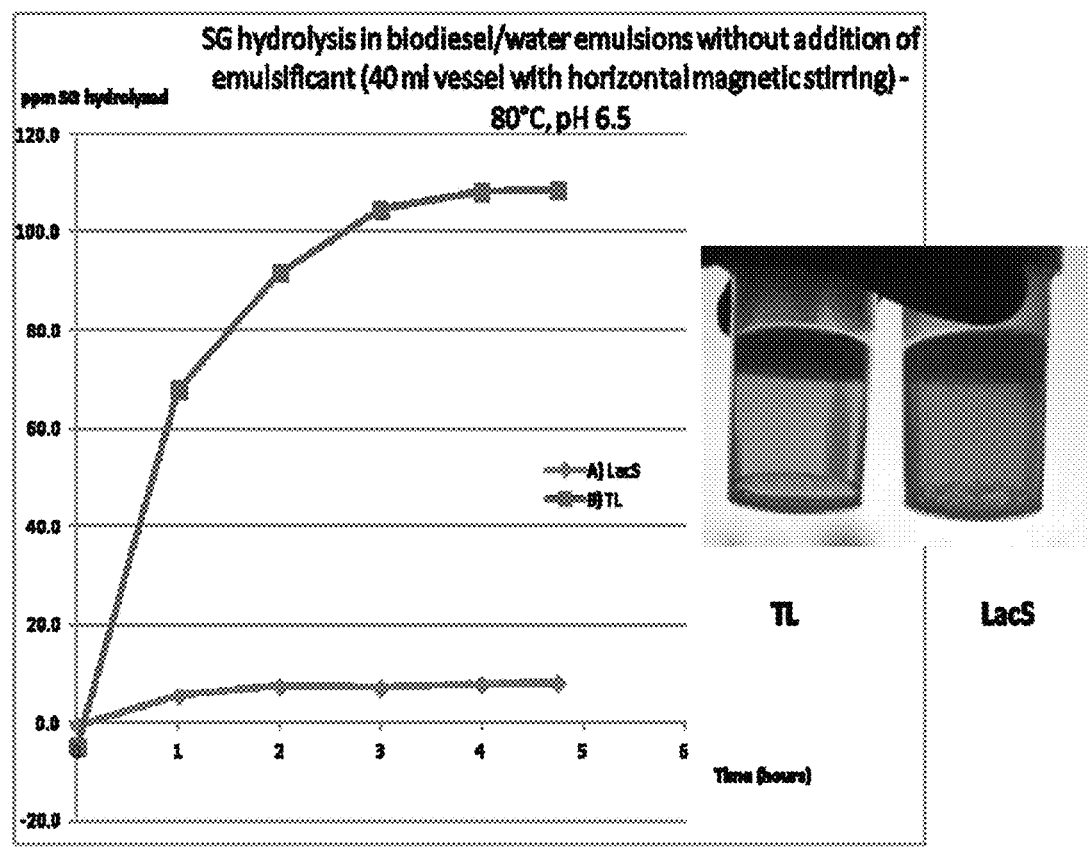
FIG. 6 is a graph and set of photographs depicting the hydrolysis of an SG using example SGases *Sulfolobus solfataricus* LacS and *Thermococcus litoralis* TL in 40 ml flasks without emulsifier (3 ug Ez/ml biodiesel, 120 ppm SG).
Figure 7:
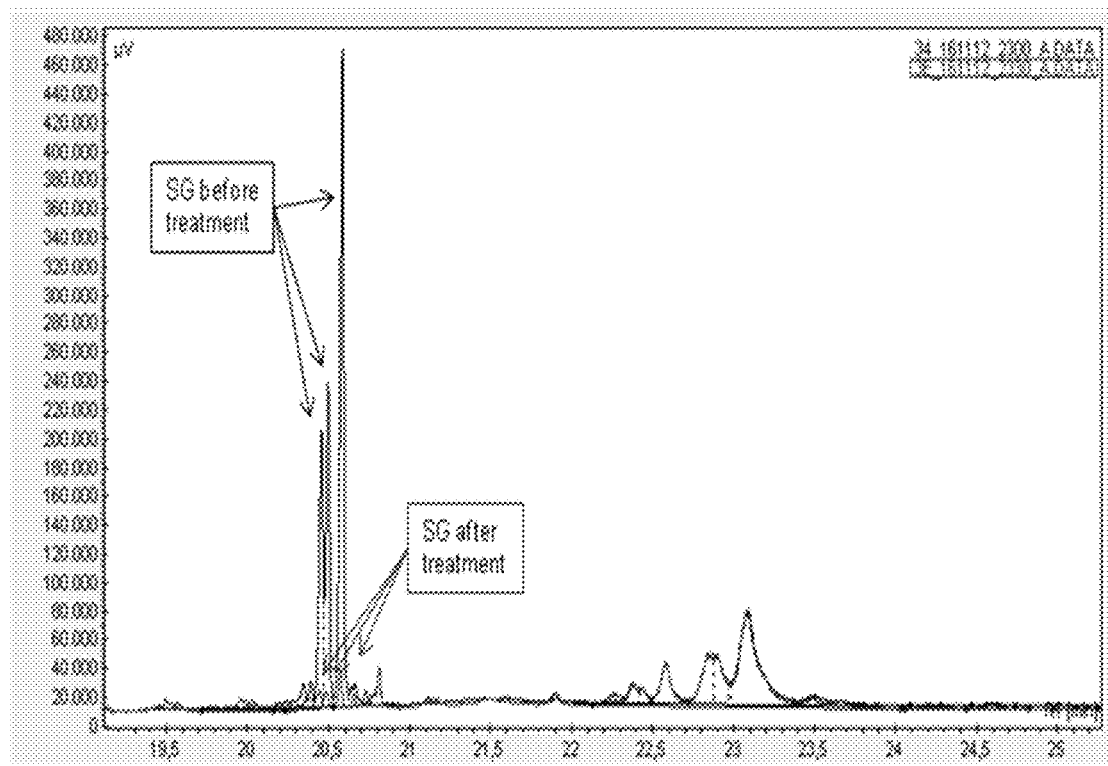
FIG. 7 is a plot depicting gas chromatography-flame ionization detection (GC-FID) analysis of biodiesel samples before and after enzymatic treatment with an example SGase (TL).

Experiments were performed using two different steryl glycosidase selected among those described in Table 1: LacS from *S. solfataricus* (SEQ ID NO.: 2) and TL from *T. litoralis* (SEQ ID NO.: 17). LacS could only exhibit steryl glycoside hydrolisis when reactions were performed in the presence of ADMUL™ (FIG. 5 and FIG. 6). Experiments performed with TL enzyme showed a higher and faster hydrolysis in Bio/water+ADMUL emulsions than LacS (data not shown). Moreover, TL could hydrolize steryl glycosides without the addition of any emulsifier, reaching almost 100% hydrolysis in 3 h (FIG. 6 and FIG. 7).

Example 6

Evaluation of Steryl Glycoside Hydrolysis in Crude Biodiesel

The following is an example of how to use a steryl glycosidase to remove steryl glycosides from crude biodiesel:
a) A 850 ml crude biodiesel sample containing about 70 ppm of steryl glycosides is mixed with 150 ml of a water solution containing 50 mM Phosphate buffer pH 6.5 and 8 mg of steryl glycosidase.
b) Transfer the mixture into a 2 L erlenmeyer and incubate for 4 h at 80° C., accompanied by stirring.

c) While the reaction takes place, take 1 ml samples every hour, separate the aqueous phase and analyze for the presence of glucose as described in the Example 1.
d) After the reaction ends, separate the organic phase and analyze for the presence of steryl glycoside by GC-FID and evaluate the quality of the resulting biodiesel by the methods currently used in the biodiesel industry (i.e. Total Contamination Test according to EN1.2662:1998 and Cold Soak Filtration Test according to ASTM D7501-12).

Figure 8:
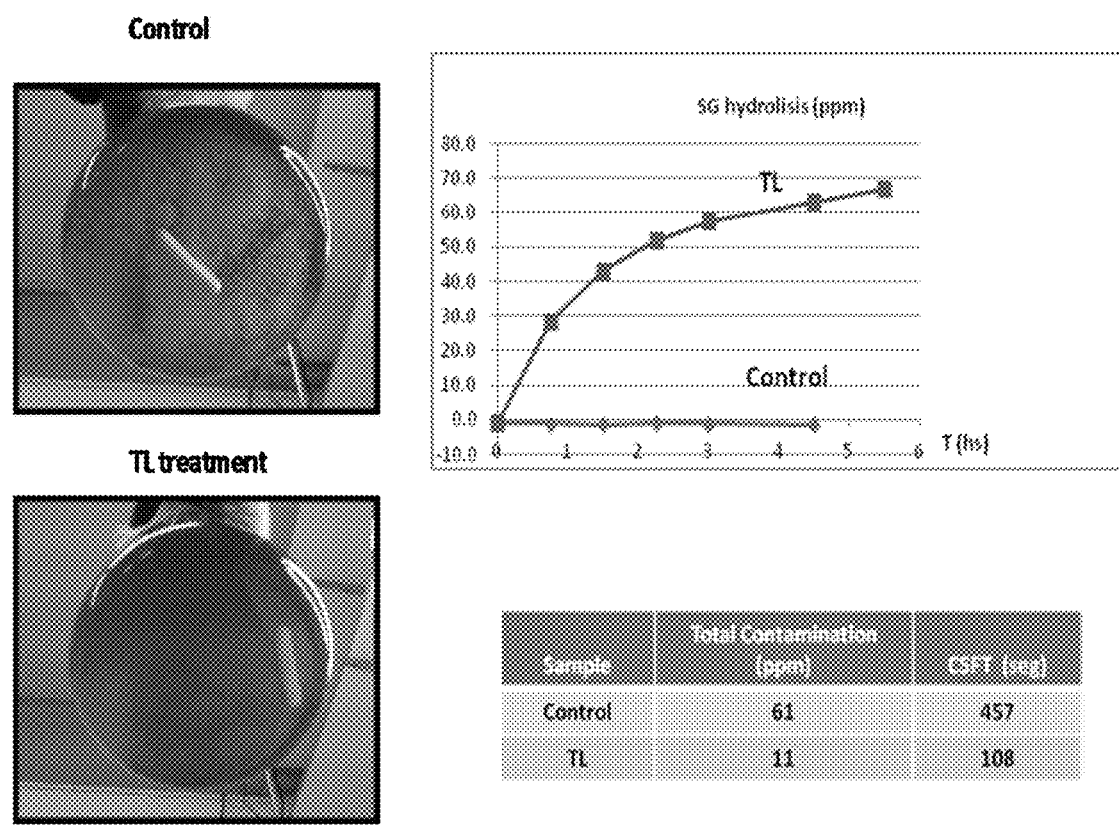
FIG. 8 is a plot and collection of photographs depicting SG hydrolysis using an example SGase (TL).

Experiments were performed using TL from *T. litoralis* (SEQ ID No.: 17). TL could completely hydrolize steryl glycosides in 3 h (FIG. 8).

---

The invention claimed is:

1. A method for reducing steryl glycoside in a sample, comprising: in a reaction mixture, mixing:
(a) a thermostable enzyme comprising SEQ ID NO: 17 or a variant having an amino acid sequence that has at least 95% identity to SEQ ID NO: 17 with (b) a sample comprising steryl glycoside, under a condition suitable for said thermostable enzyme for a suitable period of time to degrade said steryl glycoside, thereby reducing steryl glycoside in said sample to obtain a processed sample, wherein said steryl glycoside comprises steryl glucoside.

2. The method of claim 1, wherein said sample comprises oil, fat, or biofuel.

3. The method of claim 2, wherein said biofuel comprises biodiesel.

4. The method of claim 1, wherein said thermostable enzyme is capable of hydrolyzing the glycosidic bond of a steryl glucoside or acylated steryl glucoside.

5. The method of claim 1, wherein said sample comprises 0.1% to 30% of water.

6. The method of claim 1, wherein said mixing is carried out at a temperature that is between about 50° C. and about 110° C.

7. The method of claim 6, wherein said mixing is carried out at a temperature that is above about 65° C.

8. The method of claim 6, wherein said mixing is carried out at a temperature that is above about 70° C.

9. The method of claim 6, wherein said mixing is carried out at a temperature that is above about 85° C.

10. The method of claim 1, wherein said mixing is carried out for about 30 minutes to 24 hours.

11. The method of claim 1, wherein the amount of said steryl glycoside is reduced by at least 20%.

12. The method of claim 1, wherein the amount of said steryl glycoside is reduced by at least 80%.

13. The method of claim 1, wherein said processed sample comprises less than about 20 ppm of said steryl glycoside.

14. The method of claim 1, further comprising collecting said processed sample.

* * * * *

SEQUENCE LISTING

```
<160> NUMBER OF SEQ ID NOS: 22

<210> SEQ ID NO 1
<211> LENGTH: 491
<212> TYPE: PRT
<213> ORGANISM: Sulfolobus acidocaldarius

<400> SEQUENCE: 1

Met Leu Ser Phe Pro Lys Gly Phe Lys Phe Gly Trp Ser Gln Ser Gly
1               5                   10                  15

Phe Gln Ser Glu Met Gly Thr Pro Gly Ser Glu Asp Pro Asn Ser Asp
            20                  25                  30

Trp His Val Trp Val His Asp Arg Glu Asn Ile Val Ser Gln Val Val
        35                  40                  45

Ser Gly Asp Leu Pro Glu Asn Gly Pro Gly Tyr Trp Gly Asn Tyr Lys
    50                  55                  60

Arg Phe His Asp Glu Ala Glu Lys Ile Gly Leu Asn Ala Val Arg Ile
65                  70                  75                  80

Asn Val Glu Trp Ser Arg Ile Phe Pro Arg Pro Leu Pro Lys Pro Glu
                85                  90                  95

Met Gln Thr Gly Thr Asp Lys Glu Asn Ser Pro Val Ile Ser Val Asp
            100                 105                 110

Leu Asn Glu Ser Lys Leu Arg Glu Met Asp Asn Tyr Ala Asn His Glu
        115                 120                 125

Ala Leu Ser His Tyr Arg Gln Ile Leu Glu Asp Leu Arg Asn Arg Gly
    130                 135                 140

Phe His Ile Val Leu Asn Met Tyr His Trp Thr Leu Pro Ile Trp Leu
145                 150                 155                 160

His Asp Pro Ile Arg Val Arg Arg Gly Asp Phe Thr Gly Pro Thr Gly
                165                 170                 175

Trp Leu Asn Ser Arg Thr Val Tyr Glu Phe Ala Arg Phe Ser Ala Tyr
            180                 185                 190

Val Ala Trp Lys Leu Asp Asp Leu Ala Ser Glu Tyr Ala Thr Met Asn
        195                 200                 205

Glu Pro Asn Val Val Trp Gly Ala Gly Tyr Ala Phe Pro Arg Ala Gly
    210                 215                 220

Phe Pro Pro Asn Tyr Leu Ser Phe Arg Leu Ser Glu Ile Ala Lys Trp
225                 230                 235                 240

Asn Ile Ile Gln Ala His Ala Arg Ala Tyr Asp Ala Ile Lys Ser Val
                245                 250                 255

Ser Lys Lys Ser Val Gly Ile Ile Tyr Ala Asn Thr Ser Tyr Tyr Pro
            260                 265                 270

Leu Arg Pro Gln Asp Asn Glu Ala Val Glu Ile Ala Glu Arg Leu Asn
        275                 280                 285

Arg Trp Ser Phe Phe Asp Ser Ile Ile Lys Gly Glu Ile Thr Ser Glu
    290                 295                 300

Gly Gln Asn Val Arg Glu Asp Leu Arg Asn Arg Leu Asp Trp Ile Gly
305                 310                 315                 320

Val Asn Tyr Tyr Thr Arg Thr Val Val Thr Lys Ala Glu Ser Gly Tyr
```

```
                        325                 330                 335
Leu Thr Leu Pro Gly Tyr Gly Asp Arg Cys Glu Arg Asn Ser Leu Ser
                340                 345                 350

Leu Ala Asn Leu Pro Thr Ser Asp Phe Gly Trp Glu Phe Phe Pro Glu
            355                 360                 365

Gly Leu Tyr Asp Val Leu Leu Lys Tyr Trp Asn Arg Tyr Gly Leu Pro
        370                 375                 380

Leu Tyr Val Met Glu Asn Gly Ile Ala Asp Ala Asp Tyr Gln Arg
385                 390                 395                 400

Pro Tyr Tyr Leu Val Ser His Ile Tyr Gln Val His Arg Ala Leu Asn
                405                 410                 415

Glu Gly Val Asp Val Arg Gly Tyr Leu His Trp Ser Leu Ala Asp Asn
            420                 425                 430

Tyr Glu Trp Ser Ser Gly Phe Ser Met Arg Phe Gly Leu Leu Lys Val
        435                 440                 445

Asp Tyr Leu Thr Lys Arg Leu Tyr Trp Arg Pro Ser Ala Leu Val Tyr
    450                 455                 460

Arg Glu Ile Thr Arg Ser Asn Gly Ile Pro Glu Glu Leu Glu His Leu
465                 470                 475                 480

Asn Arg Val Pro Pro Ile Lys Pro Leu Arg His
                485                 490

<210> SEQ ID NO 2
<211> LENGTH: 489
<212> TYPE: PRT
<213> ORGANISM: Sulfolobus solfataricus

<400> SEQUENCE: 2

Met Tyr Ser Phe Pro Asn Ser Phe Arg Phe Gly Trp Ser Gln Ala Gly
1               5                   10                  15

Phe Gln Ser Glu Met Gly Thr Pro Gly Ser Glu Asp Pro Asn Thr Asp
            20                  25                  30

Trp Tyr Lys Trp Val His Asp Pro Glu Asn Met Ala Ala Gly Leu Val
        35                  40                  45

Ser Gly Asp Leu Pro Glu Asn Gly Pro Gly Tyr Trp Gly Asn Tyr Lys
    50                  55                  60

Thr Phe His Asp Asn Ala Gln Lys Met Gly Leu Lys Ile Ala Arg Leu
65                  70                  75                  80

Asn Val Glu Trp Ser Arg Ile Phe Pro Asn Pro Leu Pro Arg Pro Gln
                85                  90                  95

Asn Phe Asp Glu Ser Lys Gln Asp Val Thr Glu Val Glu Ile Asn Glu
            100                 105                 110

Asn Glu Leu Lys Arg Leu Asp Glu Tyr Ala Asn Lys Asp Ala Leu Asn
        115                 120                 125

His Tyr Arg Glu Ile Phe Lys Asp Leu Lys Ser Arg Gly Leu Tyr Phe
    130                 135                 140

Ile Leu Asn Met Tyr His Trp Pro Leu Pro Leu Trp Leu His Asp Pro
145                 150                 155                 160

Ile Arg Val Arg Arg Gly Asp Phe Thr Gly Pro Ser Gly Trp Leu Ser
                165                 170                 175

Thr Arg Thr Val Tyr Glu Phe Ala Arg Phe Ser Ala Tyr Ile Ala Trp
            180                 185                 190

Lys Phe Asp Asp Leu Val Asp Glu Tyr Ser Thr Met Asn Glu Pro Asn
        195                 200                 205
```

-continued

```
Val Val Gly Gly Leu Gly Tyr Val Gly Val Lys Ser Gly Phe Pro Pro
    210                 215                 220

Gly Tyr Leu Ser Phe Glu Leu Ser Arg Arg Ala Met Tyr Asn Ile Ile
225                 230                 235                 240

Gln Ala His Ala Arg Ala Tyr Asp Gly Ile Lys Ser Val Ser Lys Lys
                245                 250                 255

Pro Val Gly Ile Ile Tyr Ala Asn Ser Ser Phe Gln Pro Leu Thr Asp
                260                 265                 270

Lys Asp Met Glu Ala Val Glu Met Ala Glu Asn Asp Asn Arg Trp Trp
                275                 280                 285

Phe Phe Asp Ala Ile Ile Arg Gly Glu Ile Thr Arg Gly Asn Glu Lys
290                 295                 300

Ile Val Arg Asp Asp Leu Lys Gly Arg Leu Asp Trp Ile Gly Val Asn
305                 310                 315                 320

Tyr Tyr Thr Arg Thr Val Val Lys Arg Thr Glu Lys Gly Tyr Val Ser
                325                 330                 335

Leu Gly Gly Tyr Gly His Gly Cys Glu Arg Asn Ser Val Ser Leu Ala
                340                 345                 350

Gly Leu Pro Thr Ser Asp Phe Gly Trp Glu Phe Phe Pro Glu Gly Leu
                355                 360                 365

Tyr Asp Val Leu Thr Lys Tyr Trp Asn Arg Tyr His Leu Tyr Met Tyr
370                 375                 380

Val Thr Glu Asn Gly Ile Ala Asp Asp Ala Asp Tyr Gln Arg Pro Tyr
385                 390                 395                 400

Tyr Leu Val Ser His Val Tyr Gln Val His Arg Ala Ile Asn Ser Gly
                405                 410                 415

Ala Asp Val Arg Gly Tyr Leu His Trp Ser Leu Ala Asp Asn Tyr Glu
                420                 425                 430

Trp Ala Ser Gly Phe Ser Met Arg Phe Gly Leu Leu Lys Val Asp Tyr
                435                 440                 445

Asn Thr Lys Arg Leu Tyr Trp Arg Pro Ser Ala Leu Val Tyr Arg Glu
                450                 455                 460

Ile Ala Thr Asn Gly Ala Ile Thr Asp Glu Ile Glu His Leu Asn Ser
465                 470                 475                 480

Val Pro Pro Val Lys Pro Leu Arg His
                485
```

<210> SEQ ID NO 3
<211> LENGTH: 489
<212> TYPE: PRT
<213> ORGANISM: Sulfolobus islandicus

<400> SEQUENCE: 3

```
Met Tyr Ser Phe Pro Lys Asn Phe Arg Phe Gly Trp Ser Gln Ala Gly
1               5                   10                  15

Phe Gln Ser Glu Met Gly Thr Pro Gly Ser Glu Asp Pro Asn Thr Asp
                20                  25                  30

Trp Tyr Lys Trp Val His Asp Pro Glu Asn Ile Ala Ala Gly Leu Val
            35                  40                  45

Ser Gly Asp Leu Pro Glu Asn Gly Pro Gly Tyr Trp Gly Asn Tyr Lys
        50                  55                  60

Thr Phe His Asp Asn Ala Gln Lys Met Gly Leu Lys Met Ala Arg Leu
65                  70                  75                  80

Asn Val Glu Trp Ser Arg Ile Phe Pro Asn Pro Leu Pro Lys Pro Gln
                85                  90                  95
```

```
Asn Phe Asp Glu Ser Lys Gln Asp Val Thr Glu Val Glu Ile Asn Gln
            100                 105                 110

Asn Glu Leu Arg Arg Leu Asp Glu His Ala Asn Lys Asp Ala Leu Asn
            115                 120                 125

His Tyr Arg Glu Ile Phe Lys Asp Leu Lys Ser Arg Gly Ile Tyr Phe
            130                 135                 140

Ile Leu Asn Met Tyr His Trp Pro Leu Pro Ser Trp Leu His Asp Pro
145                 150                 155                 160

Ile Arg Val Arg Arg Gly Asp Leu Ser Gly Pro Thr Gly Trp Leu Ser
                165                 170                 175

Thr Arg Thr Val Tyr Glu Phe Ala Arg Phe Ser Ala Tyr Ile Ala Trp
            180                 185                 190

Lys Phe Asp Asp Leu Val Asp Glu Tyr Ser Thr Met Asn Glu Pro Asn
            195                 200                 205

Val Val Gly Gly Leu Gly Tyr Val Gly Val Lys Ser Gly Phe Pro Pro
            210                 215                 220

Gly Tyr Leu Ser Phe Glu Leu Ser Arg Lys Ala Met Tyr Asn Ile Ile
225                 230                 235                 240

Gln Ala His Val Arg Ala Tyr Asp Gly Ile Lys Ser Val Ser Lys Lys
                245                 250                 255

Pro Ile Gly Ile Ile Tyr Ala Asn Ser Ser Phe Gln Pro Leu Thr Glu
            260                 265                 270

Lys Asp Met Glu Ala Val Glu Met Ala Glu Tyr Asp Asn Arg Trp Ala
            275                 280                 285

Phe Phe Asp Ala Ile Ile Arg Gly Glu Ile Met Lys Gly Ser Glu Lys
            290                 295                 300

Val Val Arg Asp Asp Leu Arg Gly Arg Leu Asp Trp Ile Gly Val Asn
305                 310                 315                 320

Tyr Tyr Thr Arg Thr Val Val Lys Lys Thr Glu Lys Gly Tyr Val Ser
                325                 330                 335

Leu Gly Gly Tyr Gly His Gly Cys Glu Arg Asn Ser Val Ser Leu Ala
            340                 345                 350

Gly Leu Pro Thr Ser Asp Phe Gly Trp Glu Phe Phe Pro Glu Gly Leu
            355                 360                 365

Tyr Asp Val Leu Thr Lys Tyr Trp Asn Arg Tyr His Leu His Met Tyr
            370                 375                 380

Val Thr Glu Asn Gly Ile Ala Asp Asp Ala Asp Tyr Gln Arg Pro Tyr
385                 390                 395                 400

Tyr Leu Val Ser His Val Tyr Gln Val His Arg Ala Ile Asn Ser Ser
                405                 410                 415

Ala Asp Val Arg Gly Tyr Leu His Trp Ser Leu Ala Asp Asn Tyr Glu
            420                 425                 430

Trp Ala Ser Gly Phe Ser Met Arg Phe Gly Leu Leu Lys Val Asp Tyr
            435                 440                 445

Gly Thr Lys Arg Leu Tyr Trp Arg Pro Ser Ala Leu Val Tyr Arg Glu
            450                 455                 460

Ile Ala Thr Asn Gly Gly Ile Thr Asp Glu Ile Glu His Leu Asn Ser
465                 470                 475                 480

Val Pro Pro Ile Arg Pro Leu Arg His
                485

<210> SEQ ID NO 4
<211> LENGTH: 489
```

<212> TYPE: PRT
<213> ORGANISM: Sulfolobus islandicus

<400> SEQUENCE: 4

```
Met Asp Ile Ser Phe Pro Lys Ser Phe Arg Phe Gly Trp Ser Gln Ala
1               5                   10                  15

Gly Phe Gln Ser Glu Met Gly Thr Pro Gly Ser Glu Asp Pro Asn Thr
            20                  25                  30

Asp Trp Tyr Val Trp Val His Asp Pro Glu Asn Ile Ala Ser Gly Leu
        35                  40                  45

Val Ser Gly Asp Leu Pro Glu His Gly Pro Gly Tyr Trp Gly Leu Tyr
    50                  55                  60

Arg Met Phe His Asp Asn Ala Val Lys Met Gly Leu Asp Ile Ala Arg
65                  70                  75                  80

Ile Asn Val Glu Trp Ser Arg Ile Phe Pro Lys Pro Met Pro Asp Pro
                85                  90                  95

Pro Gln Gly Asn Val Glu Val Lys Gly Asn Asp Val Leu Ala Val His
            100                 105                 110

Val Asp Glu Asn Asp Leu Lys Arg Leu Asp Glu Ala Ala Asn Gln Glu
        115                 120                 125

Ala Val Arg His Tyr Arg Glu Ile Phe Ser Asp Leu Lys Ala Arg Gly
    130                 135                 140

Ile His Phe Ile Leu Asn Phe Tyr His Trp Pro Leu Pro Leu Trp Val
145                 150                 155                 160

His Asp Pro Ile Arg Val Arg Lys Gly Asp Leu Ser Gly Pro Thr Gly
                165                 170                 175

Trp Leu Asp Val Lys Thr Val Ile Asn Phe Ala Arg Phe Ala Ala Tyr
            180                 185                 190

Thr Ala Trp Lys Phe Asp Asp Leu Ala Asp Glu Tyr Ser Thr Met Asn
        195                 200                 205

Glu Pro Asn Val Val His Ser Asn Gly Tyr Met Trp Val Lys Ser Gly
    210                 215                 220

Phe Pro Pro Ser Tyr Leu Asn Phe Glu Leu Ser Arg Arg Val Met Val
225                 230                 235                 240

Asn Leu Ile Gln Ala His Ala Arg Ala Tyr Asp Ala Val Lys Ala Ile
                245                 250                 255

Ser Lys Lys Pro Ile Gly Ile Ile Tyr Ala Asn Ser Ser Phe Thr Pro
            260                 265                 270

Leu Thr Asp Lys Asp Ala Lys Ala Val Glu Leu Ala Glu Tyr Asp Ser
        275                 280                 285

Arg Trp Ile Phe Phe Asp Ala Ile Ile Lys Gly Glu Leu Met Gly Val
    290                 295                 300

Thr Arg Asp Asp Leu Lys Gly Arg Leu Asp Trp Ile Gly Val Asn Tyr
305                 310                 315                 320

Tyr Ser Arg Thr Val Val Lys Leu Ile Gly Glu Lys Ser Tyr Val Ser
                325                 330                 335

Ile Pro Gly Tyr Gly Tyr Gly Cys Glu Arg Asn Ser Ile Ser Pro Asp
            340                 345                 350

Gly Arg Pro Cys Ser Asp Phe Gly Trp Glu Phe Tyr Pro Glu Gly Leu
        355                 360                 365

Tyr Asp Val Ile Met Lys Tyr Trp Ser Arg Tyr His Leu Pro Ile Tyr
    370                 375                 380

Val Thr Glu Asn Gly Ile Ala Asp Ala Ala Asp Tyr Gln Arg Pro Tyr
385                 390                 395                 400
```

```
Tyr Leu Val Ser His Ile Tyr Gln Val Tyr Arg Ala Ile Gln Glu Gly
                405                 410                 415

Ala Asn Val Lys Gly Tyr Leu His Trp Ser Leu Thr Asp Asn Tyr Glu
            420                 425                 430

Trp Ala Ser Gly Phe Ser Met Arg Phe Gly Leu Leu Gln Val Asp Tyr
        435                 440                 445

Ser Thr Lys Lys Gln Tyr Trp Arg Pro Ser Ala Tyr Val Tyr Arg Glu
    450                 455                 460

Ile Ala Lys Ser Lys Ala Ile Pro Glu Glu Leu Met His Leu Asn Thr
465                 470                 475                 480

Ile Pro Pro Thr Arg Ser Leu Arg Arg
                485

<210> SEQ ID NO 5
<211> LENGTH: 489
<212> TYPE: PRT
<213> ORGANISM: Vulcanisaeta distributa

<400> SEQUENCE: 5

Met Thr Leu Ser Phe Pro Lys Gly Phe Arg Phe Gly Trp Ser Gln Ala
1               5                   10                  15

Gly Phe Gln His Glu Met Gly Ile Pro Gly Asp Glu Asp Thr Asn Ser
            20                  25                  30

Asp Trp Trp Val Trp Val His Asp Arg Asp Asn Ile Val Ser Gly Leu
        35                  40                  45

Val Ser Gly Asp Leu Pro Glu Asn Gly Pro Gly Tyr Trp Ser Leu Tyr
    50                  55                  60

Arg Val Phe His Asp Asn Ala Val Arg Met Gly Leu Asp Ile Ala Arg
65                  70                  75                  80

Val Asn Val Glu Trp Ser Arg Ile Phe Pro Lys Pro Met Pro Glu Pro
                85                  90                  95

Pro Asn Gly Asn Val Glu Val Val Gly Asp Lys Val Ile Lys Val Asp
            100                 105                 110

Val Asp Glu Arg Asp Leu Arg Arg Leu Asp Glu Thr Ala Asn Lys Ala
        115                 120                 125

Ala Ile Glu His Tyr Arg Ala Ile Phe Asn Asp Leu Lys Asn Arg Asn
    130                 135                 140

Ile Phe Phe Ile Leu Asn Leu Tyr His Trp Pro Leu Pro Leu Trp Val
145                 150                 155                 160

His Asp Pro Ile Arg Val Arg Lys Gly Asp Leu Ser Gly Pro Thr Gly
                165                 170                 175

Trp Leu Asp Ile Lys Thr Val Ile Asn Phe Ala Arg Phe Ala Ala Tyr
            180                 185                 190

Val Ala Trp Lys Leu Asp Asp Leu Val Asp Met Tyr Ser Thr Met Asn
        195                 200                 205

Glu Pro Asn Val Val Ala Trp Asn Gly Tyr Ile Asn Val Lys Ser Gly
    210                 215                 220

Phe Pro Pro Ser Tyr Leu Asn Pro Asp Leu Ala Arg Lys Ala Leu Val
225                 230                 235                 240

Asn Leu Ile Gln Ala His Ala Arg Ala Tyr Asp Ala Ile Lys Thr Val
                245                 250                 255

Ser Arg Lys Pro Val Gly Ile Ile Tyr Ala Asn Asn Ala Tyr Thr Pro
            260                 265                 270

Leu Thr Glu Lys Asp Ser Lys Ala Val Glu Leu Ala Glu Gln Asp Ala
```

```
                275                 280                 285
Arg Trp Ser Phe Phe Asp Ala Val Ile His Gly Asn Leu Tyr Gly Glu
    290                 295                 300

Val Arg Glu Asp Leu Arg Asn Arg Leu Asp Trp Ile Gly Ala Asn Tyr
305                 310                 315                 320

Tyr Ser Arg Leu Val Val Lys Leu Ile Ser Asp Asn Ser Tyr Ala Ile
                325                 330                 335

Val Pro Gly Tyr Gly His Ala Cys Glu Arg Asn Ser Val Ser Pro Asp
            340                 345                 350

Asn Arg Pro Cys Ser Asp Phe Gly Trp Glu Phe Tyr Pro Glu Gly Leu
        355                 360                 365

Tyr Asp Val Leu Thr Lys Tyr Trp Arg Arg Tyr His Leu Pro Ile Tyr
    370                 375                 380

Val Thr Glu Asn Gly Ile Ala Asp Ser Ala Asp Tyr Leu Arg Pro Tyr
385                 390                 395                 400

Tyr Leu Val Ser His Ile Tyr Gln Val Tyr Arg Ala Leu Ser Asp Gly
                405                 410                 415

Val Asp Val Arg Gly Tyr Leu His Trp Ser Leu Thr Asp Asn Tyr Glu
            420                 425                 430

Trp Ala Ser Gly Phe Ser Met Arg Phe Gly Leu Leu Tyr Val Asp Tyr
        435                 440                 445

Thr Thr Lys Arg Gln Tyr Trp Arg Pro Ser Ala Tyr Ile Tyr Arg Glu
    450                 455                 460

Ile Ala Leu Asn Lys Ala Ile Pro Asp Glu Leu Met His Leu Asn Thr
465                 470                 475                 480

Ile Pro Pro Val Arg Ser Leu Arg Lys
                485

<210> SEQ ID NO 6
<211> LENGTH: 489
<212> TYPE: PRT
<213> ORGANISM: Vulcanisaeta moutnovskia

<400> SEQUENCE: 6

Met Thr Leu Ser Phe Pro Gln Asp Phe Arg Phe Gly Trp Ser Gln Ala
1               5                   10                  15

Gly Phe Gln His Glu Met Gly Ile Pro Gly Asp Glu Asp Pro Asn Ser
            20                  25                  30

Asp Trp Trp Val Trp Val His Asp Arg Asp Asn Ile Ala Ser Gly Leu
        35                  40                  45

Val Ser Gly Asp Leu Pro Glu Asn Gly Pro Gly Tyr Trp Ser Leu Tyr
    50                  55                  60

Arg Val Phe His Asp Asn Ala Val Arg Met Gly Leu Asp Ile Ala Arg
65                  70                  75                  80

Ile Asn Val Glu Trp Ser Arg Val Phe Pro Lys Pro Met Pro Glu Pro
                85                  90                  95

Pro Ser Gly Asn Val Glu Val Val Gly Asp Asn Val Ile Lys Val Asp
            100                 105                 110

Val Asp Glu Arg Asp Leu Arg Arg Leu Asp Glu Ala Ala Asn Lys Ala
        115                 120                 125

Ala Val Glu His Tyr Arg Val Met Phe Asn Asp Leu Lys Asn Arg Asn
    130                 135                 140

Ile Phe Phe Ile Leu Asn Leu Tyr His Trp Pro Leu Pro Leu Trp Ile
145                 150                 155                 160
```

```
His Asp Pro Ile Arg Val Arg Arg Gly Asp Leu Ser Gly Pro Thr Gly
                165                 170                 175

Trp Leu Asp Val Lys Thr Val Ile Asn Phe Ala Arg Phe Ala Ala Tyr
            180                 185                 190

Val Ala Trp Arg Phe Asp Asp Leu Val Asp Met Tyr Ser Thr Met Asn
        195                 200                 205

Glu Pro Asn Val Val Ala Tyr Ala Gly Tyr Ala Asn Val Lys Ser Gly
    210                 215                 220

Phe Pro Pro Gly Tyr Leu Asn Pro Gly Leu Ala Arg Arg Ala Leu Ile
225                 230                 235                 240

Asn Leu Ile Gln Ala His Ala Arg Ala Tyr Asp Ala Ile Lys Ala Ile
                245                 250                 255

Ser Arg Lys Pro Val Gly Ile Ile Tyr Ala Asn Asn Ala Tyr Thr Pro
            260                 265                 270

Leu Thr Glu Lys Asp Ala Gly Ala Val Glu Leu Ala Glu Gln Asp Ala
        275                 280                 285

Arg Trp Ser Phe Phe Asp Ala Ile Ile His Gly Asn Leu Tyr Gly Glu
    290                 295                 300

Val Arg Asp Asp Leu Arg Gly Arg Leu Asp Trp Ile Gly Val Asn Tyr
305                 310                 315                 320

Tyr Ser Arg Leu Val Val Arg Leu Thr Gly Glu Asn Ser Tyr Ser Val
                325                 330                 335

Val Pro Gly Tyr Gly His Ala Cys Glu Arg Asn Ser Val Ser Pro Asp
            340                 345                 350

Asn Lys Pro Cys Ser Asp Phe Gly Trp Glu Phe Tyr Pro Glu Gly Leu
        355                 360                 365

Tyr Asp Val Leu Met Lys Tyr Trp Arg Arg Tyr Arg Leu Pro Met Tyr
    370                 375                 380

Val Thr Glu Asn Gly Ile Ala Asp Ala Ala Asp Tyr Leu Arg Pro Tyr
385                 390                 395                 400

Tyr Leu Val Ser His Val Tyr Gln Val His Arg Ala Leu Gly Asp Gly
                405                 410                 415

Ala Asp Val Arg Gly Tyr Leu His Trp Ser Leu Thr Asp Asn Tyr Glu
            420                 425                 430

Trp Ala Ser Gly Phe Ser Met Arg Phe Gly Leu Leu Tyr Val Asp Tyr
        435                 440                 445

Ser Ser Lys Lys Gln Tyr Trp Arg Pro Ser Ala Tyr Ile Tyr Arg Glu
    450                 455                 460

Ile Ala Met Asn Lys Ala Ile Pro Asp Glu Leu Met His Leu Asn Ala
465                 470                 475                 480

Val Pro Pro Ile Arg Pro Leu Arg Arg
                485

<210> SEQ ID NO 7
<211> LENGTH: 489
<212> TYPE: PRT
<213> ORGANISM: Vulcanisaeta distributa

<400> SEQUENCE: 7

Met Thr Leu Ser Phe Pro Lys Gly Phe Arg Phe Gly Trp Ser Gln Ala
1               5                   10                  15

Gly Phe Gln His Glu Met Gly Ile Pro Gly Asp Glu Asp Thr Asn Ser
                20                  25                  30

Asp Trp Trp Val Trp Val His Asp Arg Asp Asn Ile Val Ser Gly Leu
            35                  40                  45
```

```
Val Ser Gly Asp Leu Pro Glu Asn Gly Pro Gly Tyr Trp Ser Leu Tyr
    50                  55                  60

Arg Val Phe His Asp Asn Ala Val Arg Met Gly Leu Asp Ile Ala Arg
 65                  70                  75                  80

Val Asn Val Glu Trp Ser Arg Ile Phe Pro Lys Pro Met Pro Glu Pro
                 85                  90                  95

Pro Asn Gly Asn Val Glu Val Gly Asp Lys Val Ile Lys Val Asp
            100                 105                 110

Val Asp Glu Arg Asp Leu Arg Arg Leu Asp Glu Thr Ala Asn Lys Ala
            115                 120                 125

Ala Ile Glu His Tyr Arg Ala Ile Phe Asn Asp Leu Lys Asn Arg Asn
            130                 135                 140

Ile Phe Phe Ile Leu Asn Leu Tyr His Trp Pro Leu Pro Leu Trp Val
145                 150                 155                 160

His Asp Pro Ile Arg Val Arg Lys Gly Asp Leu Ser Gly Pro Thr Gly
                165                 170                 175

Trp Leu Asp Ile Lys Thr Val Ile Asn Phe Ala Arg Phe Ala Ala Tyr
                180                 185                 190

Val Ala Trp Lys Leu Asp Asp Leu Val Asp Met Tyr Ser Thr Met Asn
            195                 200                 205

Glu Pro Asn Val Val Ala Trp Asn Gly Tyr Ile Asn Val Lys Ser Gly
210                 215                 220

Phe Pro Pro Ser Tyr Leu Asn Pro Asp Leu Ala Arg Lys Ala Leu Val
225                 230                 235                 240

Asn Leu Ile Gln Ala His Ala Arg Ala Tyr Asp Ala Ile Lys Thr Val
                245                 250                 255

Ser Arg Lys Pro Val Gly Ile Ile Tyr Ala Asn Asn Ala Tyr Thr Pro
            260                 265                 270

Leu Thr Glu Lys Asp Ser Lys Ala Val Glu Leu Ala Glu Gln Asp Ala
            275                 280                 285

Arg Trp Ser Phe Phe Asp Ala Val Ile His Gly Asn Leu Tyr Gly Glu
            290                 295                 300

Val Arg Glu Asp Leu Arg Asn Arg Leu Asp Trp Ile Gly Ala Asn Tyr
305                 310                 315                 320

Tyr Ser Arg Leu Val Val Lys Leu Ile Ser Asp Asn Ser Tyr Ala Ile
                325                 330                 335

Val Pro Gly Tyr Gly His Ala Cys Glu Arg Asn Ser Val Ser Pro Asp
            340                 345                 350

Asn Arg Pro Cys Ser Asp Phe Gly Trp Glu Phe Tyr Pro Glu Gly Leu
            355                 360                 365

Tyr Asp Val Leu Thr Lys Tyr Trp Arg Arg Tyr His Leu Pro Ile Tyr
            370                 375                 380

Val Thr Glu Asn Gly Ile Ala Asp Ser Ala Asp Tyr Leu Arg Pro Tyr
385                 390                 395                 400

Tyr Leu Val Ser His Ile Tyr Gln Val Tyr Arg Ala Leu Ser Asp Gly
                405                 410                 415

Val Asp Val Arg Gly Tyr Leu His Trp Ser Leu Thr Asp Asn Tyr Glu
            420                 425                 430

Trp Ala Ser Gly Phe Ser Met Arg Phe Gly Leu Leu Tyr Val Asp Tyr
            435                 440                 445

Thr Thr Lys Arg Gln Tyr Trp Arg Pro Ser Ala Tyr Ile Tyr Arg Glu
            450                 455                 460
```

```
Ile Ala Leu Asn Lys Ala Ile Pro Asp Glu Leu Met His Leu Asn Thr
465                 470                 475                 480

Ile Pro Pro Val Arg Ser Leu Arg Lys
                485
```

<210> SEQ ID NO 8
<211> LENGTH: 489
<212> TYPE: PRT
<213> ORGANISM: Vulcanisaeta moutnovskia

<400> SEQUENCE: 8

```
Met Thr Leu Ser Phe Pro Gln Asp Phe Arg Phe Gly Trp Ser Gln Ala
1               5                   10                  15

Gly Phe Gln His Glu Met Gly Ile Pro Gly Asp Glu Asp Pro Asn Ser
                20                  25                  30

Asp Trp Trp Val Trp Val His Asp Arg Asp Asn Ile Ala Ser Gly Leu
            35                  40                  45

Val Ser Gly Asp Leu Pro Glu Asn Gly Pro Gly Tyr Trp Ser Leu Tyr
        50                  55                  60

Arg Val Phe His Asp Asn Ala Val Arg Met Gly Leu Asp Ile Ala Arg
65                  70                  75                  80

Ile Asn Val Glu Trp Ser Arg Val Phe Pro Lys Pro Met Pro Glu Pro
                85                  90                  95

Pro Ser Gly Asn Val Glu Val Val Gly Asp Asn Val Ile Lys Val Asp
                100                 105                 110

Val Asp Glu Arg Asp Leu Arg Arg Leu Asp Glu Ala Ala Asn Lys Ala
            115                 120                 125

Ala Val Glu His Tyr Arg Val Met Phe Asn Asp Leu Lys Asn Arg Asn
        130                 135                 140

Ile Phe Phe Ile Leu Asn Leu Tyr His Trp Pro Leu Pro Leu Trp Ile
145                 150                 155                 160

His Asp Pro Ile Arg Val Arg Arg Gly Asp Leu Ser Gly Pro Thr Gly
                165                 170                 175

Trp Leu Asp Val Lys Thr Val Ile Asn Phe Ala Arg Phe Ala Ala Tyr
            180                 185                 190

Val Ala Trp Arg Phe Asp Asp Leu Val Asp Met Tyr Ser Thr Met Asn
        195                 200                 205

Glu Pro Asn Val Val Ala Tyr Ala Gly Tyr Ala Asn Val Lys Ser Gly
210                 215                 220

Phe Pro Pro Gly Tyr Leu Asn Pro Gly Leu Ala Arg Arg Ala Leu Ile
225                 230                 235                 240

Asn Leu Ile Gln Ala His Ala Arg Ala Tyr Asp Ala Ile Lys Ala Ile
                245                 250                 255

Ser Arg Lys Pro Val Gly Ile Ile Tyr Ala Asn Ala Tyr Thr Pro
            260                 265                 270

Leu Thr Glu Lys Asp Ala Gly Ala Val Glu Leu Ala Glu Gln Asp Ala
        275                 280                 285

Arg Trp Ser Phe Phe Asp Ala Ile Ile His Gly Asn Leu Tyr Gly Glu
    290                 295                 300

Val Arg Asp Asp Leu Arg Gly Arg Leu Asp Trp Ile Gly Val Asn Tyr
305                 310                 315                 320

Tyr Ser Arg Leu Val Val Arg Leu Thr Gly Glu Asn Ser Tyr Ser Val
                325                 330                 335

Val Pro Gly Tyr Gly His Ala Cys Glu Arg Asn Ser Val Ser Pro Asp
            340                 345                 350
```

```
Asn Lys Pro Cys Ser Asp Phe Gly Trp Glu Phe Tyr Pro Glu Gly Leu
        355                 360                 365

Tyr Asp Val Leu Met Lys Tyr Trp Arg Arg Tyr Arg Leu Pro Met Tyr
    370                 375                 380

Val Thr Glu Asn Gly Ile Ala Asp Ala Ala Asp Tyr Leu Arg Pro Tyr
385                 390                 395                 400

Tyr Leu Val Ser His Val Tyr Gln Val His Arg Ala Leu Gly Asp Gly
                405                 410                 415

Ala Asp Val Arg Gly Tyr Leu His Trp Ser Leu Thr Asp Asn Tyr Glu
            420                 425                 430

Trp Ala Ser Gly Phe Ser Met Arg Phe Gly Leu Leu Tyr Val Asp Tyr
        435                 440                 445

Ser Ser Lys Lys Gln Tyr Trp Arg Pro Ser Ala Tyr Ile Tyr Arg Glu
    450                 455                 460

Ile Ala Met Asn Lys Ala Ile Pro Asp Glu Leu Met His Leu Asn Ala
465                 470                 475                 480

Val Pro Pro Ile Arg Pro Leu Arg Arg
                485

<210> SEQ ID NO 9
<211> LENGTH: 490
<212> TYPE: PRT
<213> ORGANISM: Acidilobus saccharovorans

<400> SEQUENCE: 9

Met Ala Val Thr Phe Pro Lys Asp Phe Leu Phe Gly Trp Ser Gln Ala
1               5                   10                  15

Gly Phe Gln Ser Glu Met Gly Thr Pro Gly Ser Glu Asp Pro Asn Ser
            20                  25                  30

Asp Trp Tyr Ala Trp Val His Asp Arg Glu Asn Ile Ala Ala Gly Leu
        35                  40                  45

Val Ser Gly Asp Phe Pro Glu Asn Gly Pro Gly Tyr Trp Gly Asn Tyr
    50                  55                  60

Arg Lys Phe His Asp Ala Ala Gln Ala Met Gly Leu Thr Ala Ala Arg
65                  70                  75                  80

Ile Gly Val Glu Trp Ser Arg Ile Phe Pro Arg Pro Thr Phe Asp Val
                85                  90                  95

Lys Val Asp Ala Glu Val Lys Gly Asp Asp Val Leu Ser Val Tyr Val
            100                 105                 110

Ser Glu Gly Ala Leu Glu Gln Leu Asp Lys Met Ala Asn Arg Asp Ala
        115                 120                 125

Ile Asn His Tyr Arg Glu Met Phe Ser Asp Leu Arg Ser Arg Gly Ile
    130                 135                 140

Thr Phe Ile Leu Asn Leu Tyr His Trp Pro Leu Pro Leu Trp Leu His
145                 150                 155                 160

Asp Pro Ile Ala Ile Arg Arg Gly Asn Leu Ser Ala Pro Ser Gly Trp
                165                 170                 175

Leu Asp Val Arg Thr Val Ile Glu Phe Ala Lys Phe Ser Ala Tyr Val
            180                 185                 190

Ala Trp Lys Leu Asp Asp Leu Val Tyr Met Tyr Ser Thr Met Asn Glu
        195                 200                 205

Pro Asn Val Val Trp Gly Leu Gly Tyr Ala Ala Val Lys Ser Gly Phe
    210                 215                 220

Pro Pro Gly Tyr Leu Cys Leu Glu Cys Ala Gly Arg Ala Met Lys Asn
```

```
                225                 230                 235                 240
Leu Val Gln Ala His Ala Arg Ala Tyr Asp Ala Val Lys Ala Ile Thr
            245                 250                 255

Lys Lys Pro Val Gly Val Ile Tyr Ala Asn Ser Asp Phe Thr Pro Leu
            260                 265                 270

Thr Asp Ala Asp Arg Glu Ala Glu Arg Ala Lys Phe Asp Asn Arg
            275                 280                 285

Trp Ala Phe Phe Asp Ala Val Val Arg Gly Gln Leu Gly Gly Ser Thr
            290                 295                 300

Arg Asp Asp Leu Lys Gly Arg Leu Asp Trp Ile Gly Val Asn Tyr Tyr
305                 310                 315                 320

Thr Arg Gln Val Val Arg Ala Arg Gly Ser Gly Tyr Glu Ile Val Pro
            325                 330                 335

Gly Tyr Gly His Gly Cys Glu Pro Asn Gly Val Ser Pro Ala Gly Arg
            340                 345                 350

Pro Cys Ser Asp Phe Gly Trp Glu Phe Tyr Pro Glu Gly Leu Tyr Asn
            355                 360                 365

Val Leu Lys Glu Tyr Trp Asp Arg Tyr His Leu Pro Leu Leu Val Thr
            370                 375                 380

Glu Asn Gly Ile Ala Asp Glu Gly Asp Tyr Gln Arg Pro Tyr Tyr Leu
385                 390                 395                 400

Val Ser His Val Tyr Gln Val His Arg Ala Leu Gln Asp Gly Val Asn
            405                 410                 415

Val Ile Gly Tyr Leu His Trp Ser Leu Ala Asp Asn Tyr Glu Trp Ala
            420                 425                 430

Ser Gly Phe Ser Lys Arg Phe Gly Leu Leu Met Val Asp Tyr Ser Thr
            435                 440                 445

Lys Arg Leu His Trp Arg Pro Ser Ala Phe Ile Tyr Arg Glu Ile Ala
            450                 455                 460

Lys Ser Arg Ala Ile Thr Asp Glu Ile Glu His Leu Asn Ser Val Pro
465                 470                 475                 480

Pro Leu Arg Gly Leu Ser Pro Gly His Arg
            485                 490

<210> SEQ ID NO 10
<211> LENGTH: 493
<212> TYPE: PRT
<213> ORGANISM: Thermoproteus uzoniensis

<400> SEQUENCE: 10

Met Arg Lys Phe Pro Ser Gly Phe Arg Trp Gly Trp Ser Gly Ala Gly
1               5                   10                  15

Phe Gln Phe Glu Met Gly Leu Pro Gly Ser Glu Asp Pro Asn Thr Asp
            20                  25                  30

Trp Phe Ala Trp Val His Asp Pro Glu Asn Ile Ala Ala Gly Leu Val
        35                  40                  45

Ser Gly Asp Phe Pro Glu Asn Gly Val Ala Tyr Trp His Leu Tyr Lys
    50                  55                  60

Gln Phe His Asp Asp Thr Val Lys Met Gly Leu Asn Thr Ile Arg Phe
65                  70                  75                  80

Asn Thr Glu Trp Ser Arg Ile Phe Pro Lys Pro Thr Phe Asp Val Arg
                85                  90                  95

Val His Tyr Glu Val Arg Glu Gly Arg Val Val Ser Val Asp Ile Thr
            100                 105                 110
```

```
Glu Lys Ala Leu Glu Leu Asp Lys Leu Ala Asn Lys Asp Ala Val
            115                 120                 125
Ala His Tyr Arg Glu Ile Phe Ser Asp Ile Lys Ser Arg Gly Leu Tyr
130                 135                 140
Phe Ile Leu Asn Leu Tyr His Trp Pro Met Pro Leu Trp Val His Asp
145                 150                 155                 160
Pro Ile Lys Val Arg Arg Gly Asp Leu Ser Gly Arg Asn Val Gly Trp
                165                 170                 175
Val Ala Glu Thr Thr Val Val Glu Phe Ala Lys Tyr Ala Ala Tyr Val
            180                 185                 190
Ala Trp Lys Phe Gly Asp Leu Ala Asp Glu Phe Ser Thr Phe Asn Glu
        195                 200                 205
Pro Asn Val Thr Tyr Asn Leu Gly Phe Ile Ala Val Lys Ala Gly Phe
    210                 215                 220
Pro Pro Gly Tyr Leu Ser Phe Gln Met Ala Arg Ala Ala Val Asn
225                 230                 235                 240
Leu Ile Thr Ala His Ala Arg Ala Tyr Asp Ala Ile Arg Leu Thr Ser
                245                 250                 255
Lys Lys Pro Val Gly Val Ile Tyr Ala Ala Ser Pro Val Tyr Pro Leu
            260                 265                 270
Thr Glu Ala Asp Lys Ala Ala Ala Glu Arg Ala Ala Tyr Asp Gly Leu
        275                 280                 285
Trp Phe Phe Leu Asp Ala Val Ala Lys Gly Val Leu Asp Gly Val Ala
    290                 295                 300
Gln Asp Asp Leu Lys Gly Arg Leu Asp Trp Leu Gly Ile Asn Tyr Tyr
305                 310                 315                 320
Ser Arg Ser Val Val Lys Arg Gly Asp Gly Tyr Ala Gly Val Pro
                325                 330                 335
Gly Tyr Gly Phe Ala Cys Glu Pro Asn Ser Val Ser Arg Asp Gly Arg
            340                 345                 350
Pro Thr Ser Asp Phe Gly Trp Glu Ile Tyr Pro Glu Gly Leu Tyr Asp
        355                 360                 365
Ile Leu Thr Trp Ala Trp Arg Arg Tyr Gly Leu Pro Leu Tyr Val Thr
    370                 375                 380
Glu Asn Gly Ile Ala Asp Gln His Asp Arg Trp Arg Pro Tyr Tyr Leu
385                 390                 395                 400
Val Ser His Leu Ala Gln Leu His Arg Ala Ile Gln Asp Gly Val Asn
                405                 410                 415
Val Lys Gly Tyr Leu His Trp Ser Leu Thr Asp Asn Tyr Glu Trp Ala
            420                 425                 430
Ser Gly Phe Ser Lys Lys Phe Gly Leu Ile Tyr Val Asp Leu Ser Thr
        435                 440                 445
Lys Arg His Tyr Trp Arg Pro Ser Ala Tyr Ile Tyr Arg Glu Ile Ala
    450                 455                 460
Ser Ser Asn Gly Ile Pro Asp Glu Leu Glu His Leu Glu Lys Val Pro
465                 470                 475                 480
Val Ala Ser Pro Glu Val Leu Arg Gly Leu Arg Ser Leu
                485                 490

<210> SEQ ID NO 11
<211> LENGTH: 481
<212> TYPE: PRT
<213> ORGANISM: Thermoplasma volcanium

<400> SEQUENCE: 11
```

```
Met Val Glu Asn Asn Phe Pro Glu Asp Phe Lys Phe Gly Trp Ser Gln
1               5                   10                  15

Ser Gly Phe Gln Ser Glu Met Gly Tyr Asp Asn Ala Met Asp Asp Lys
            20                  25                  30

Ser Asp Trp Tyr Val Trp Val His Asp Lys Glu Asn Ile Gln Ser Gly
                35                  40                  45

Leu Val Ser Gly Asp Met Pro Glu Asn Gly Pro Gly Tyr Trp Asn Asn
    50                  55                  60

Tyr Lys Ser Phe His Glu Ala Ala Gln Asn Met Gly Leu Lys Met Ala
65                  70                  75                  80

Arg Ile Gly Val Glu Trp Ser Arg Leu Phe Pro Glu Pro Phe Pro Glu
                85                  90                  95

Lys Ile Met Ala Asp Ala Lys Asn Asn Ser Leu Glu Ile Asn Asn Asn
                100                 105                 110

Ile Leu Ser Glu Leu Asp Lys Tyr Val Asn Lys Asp Ala Leu Asn His
                115                 120                 125

Tyr Ile Glu Ile Phe Asn Asp Ile Lys Asn Arg Asn Ile Asp Leu Ile
    130                 135                 140

Ile Asn Met Tyr His Trp Pro Leu Pro Val Trp Leu Ser Asp Pro Val
145                 150                 155                 160

Ser Val Arg Lys Gly Ile Lys Thr Glu Arg Ser Gly Trp Leu Asn Asp
                165                 170                 175

Arg Ile Val Gln Leu Phe Ala Leu Phe Ser Ser Tyr Ile Val Tyr Lys
                180                 185                 190

Met Glu Asp Leu Ala Val Ala Phe Ser Thr Met Asn Glu Pro Asn Val
                195                 200                 205

Val Tyr Gly Asn Gly Phe Ile Asn Ile Lys Ser Gly Phe Pro Pro Ser
    210                 215                 220

Tyr Leu Ser Ser Glu Phe Ala Ser Lys Val Lys Asn Asn Ile Leu Lys
225                 230                 235                 240

Ala His Ser Leu Ala Tyr Asp Ser Met Lys Lys Ile Thr Asp Lys Pro
                245                 250                 255

Val Gly Ile Ile Tyr Ala Asn Thr Tyr Phe Thr Pro Leu Asp Pro Glu
                260                 265                 270

Lys Asp Asn Asp Ala Ile Ala Lys Ala Asp Ser Asp Ala Lys Trp Ser
                275                 280                 285

Phe Phe Asp Pro Leu Ile Lys Gly Asp Lys Ser Leu Gly Ile Asn Gly
                290                 295                 300

Asn Lys Leu Asp Trp Ile Gly Ile Asn Tyr Tyr Thr Arg Thr Met Leu
305                 310                 315                 320

Arg Lys Asp Gly Asp Gly Tyr Ile Ser Leu Lys Gly Tyr Gly His Ser
                325                 330                 335

Gly Ser Pro Asn Thr Val Thr Asn Asp Lys Arg Pro Thr Ser Asp Ile
                340                 345                 350

Gly Trp Glu Phe Tyr Pro Glu Gly Leu Glu Tyr Val Ile Met Asn Tyr
                355                 360                 365

Trp Asn Arg Tyr Lys Leu Pro Met Tyr Val Thr Glu Asn Gly Ile Ala
            370                 375                 380

Asp Asn Gly Asp Tyr Gln Arg Pro Tyr Tyr Leu Val Ser His Ile Ala
385                 390                 395                 400

Ser Val Leu Arg Ala Ile Asn Lys Gly Ala Asn Val Lys Gly Tyr Leu
                405                 410                 415
```

```
His Trp Ser Leu Val Asp Asn Tyr Glu Trp Ala Leu Gly Phe Ser Pro
            420                 425                 430

Lys Phe Gly Leu Ile Gly Tyr Asp Glu Asn Lys Lys Leu Tyr Trp Arg
            435                 440                 445

Pro Ser Ala Leu Val Tyr Lys Glu Ile Ala Thr Lys Asn Cys Ile Ser
            450                 455                 460

Pro Glu Leu Lys His Leu Asp Ser Ile Pro Pro Ile Asn Gly Leu Arg
465                 470                 475                 480

Lys

<210> SEQ ID NO 12
<211> LENGTH: 486
<212> TYPE: PRT
<213> ORGANISM: Ignisphaera aggregans

<400> SEQUENCE: 12

Met Gly Leu Lys Tyr Pro Lys Glu Phe Ile Phe Gly Phe Ser Glu Ser
1               5                   10                  15

Gly Phe Gln Phe Glu Met Gly Leu Pro Gly Ser Glu Asp Pro Asn Thr
            20                  25                  30

Asp Trp Trp Val Trp Val His Asp Pro Glu Asn Ile Ala Ser Thr Leu
        35                  40                  45

Val Ser Gly Asp Phe Pro Glu Asn Gly Pro Gly Tyr Trp His Leu Tyr
    50                  55                  60

Arg Gln Asp His Asp Ile Ala Glu Arg Leu Gly Met Asp Gly Ala Arg
65                  70                  75                  80

Ile Gly Ile Glu Trp Ser Arg Ile Phe Ser Lys Pro Thr Phe Asp Val
                85                  90                  95

Lys Val Asp Val Ala Arg Asp Gly Arg Gly Asn Ile Val Tyr Ile Asp
            100                 105                 110

Val Ala Glu Lys Ala Leu Glu Glu Leu Asp Arg Ile Ala Asn Lys Asp
        115                 120                 125

Ala Val Asn His Tyr Arg Glu Ile Leu Ser Asp Trp Lys Asn Arg Gly
    130                 135                 140

Lys Lys Leu Ile Ile Asn Leu Tyr His Trp Thr Leu Pro Leu Trp Leu
145                 150                 155                 160

His Asp Pro Ile Lys Val Arg Lys Leu Gly Ile Asp Arg Ala Pro Ala
                165                 170                 175

Gly Trp Val Asp Glu Arg Thr Val Ile Glu Phe Val Lys Tyr Val Ala
            180                 185                 190

Tyr Ile Ala Trp Lys Leu Gly Asp Leu Pro Asp Leu Trp Cys Thr Met
        195                 200                 205

Asn Glu Pro Asn Val Val Tyr Ser Ile Gly Tyr Ile Asn Ile Lys Ile
    210                 215                 220

Gly Tyr Pro Pro Gly Tyr Leu Ser Phe Glu Ala Ala Ser Lys Ala Met
225                 230                 235                 240

Lys His Leu Val Glu Ala His Ala Arg Ala Tyr Glu Val Leu Lys Arg
                245                 250                 255

Phe Thr Asn Lys Pro Val Gly Ile Ile Tyr Val Thr Thr Tyr His Glu
            260                 265                 270

Pro Leu Lys Glu Ser Asp Arg Asp Val Ala Glu Ala Met Tyr Gln
        275                 280                 285

Ala Val Phe Asp Phe Leu Asp Ser Ile Thr Ile Gly Arg Ser Met Ser
    290                 295                 300
```

```
Ile Gly Glu Arg Lys Asp Leu Glu Lys His Leu Asp Trp Leu Gly Ile
305                 310                 315                 320

Asn Tyr Tyr Ser Arg Leu Val Val Glu Arg Tyr Gly Asn Ala Trp Arg
            325                 330                 335

Val Leu Pro Gly Tyr Gly Phe Ala Cys Ile Pro Gly Gly Thr Ser Leu
        340                 345                 350

Ala Gly Arg Pro Cys Asn Asp Ala Gly Trp Glu Thr Tyr Pro Glu Gly
        355                 360                 365

Leu Tyr Ile Met Leu Lys Arg Cys Trp Glu Arg Tyr Arg Leu Pro Ile
        370                 375                 380

Ile Val Thr Glu Asn Gly Thr Ala Asp Ala Ile Asp Arg Leu Arg Pro
385                 390                 395                 400

Arg Tyr Leu Ala Thr His Leu Tyr Gln Val Trp Lys Ala Leu Ser Glu
            405                 410                 415

Gly Val Asp Ile Arg Gly Tyr Leu His Trp Ala Leu Val Asp Asn Tyr
        420                 425                 430

Glu Trp Ser Ser Gly Phe Arg Met Arg Phe Gly Leu Val His Val Asp
        435                 440                 445

Phe Glu Thr Lys Lys Arg Tyr Leu Arg Pro Ser Ala Leu Leu Phe Arg
450                 455                 460

Glu Ile Ala Ser Ser Lys Glu Ile Pro Asp Glu Phe Met His Met Thr
465                 470                 475                 480

Gln Pro Gln Ile Leu Ile
            485
```

```
<210> SEQ ID NO 13
<211> LENGTH: 481
<212> TYPE: PRT
<213> ORGANISM: Thermosphaera aggregans

<400> SEQUENCE: 13

Met Lys Phe Pro Lys Asp Phe Met Ile Gly Tyr Ser Ser Pro Phe
1               5                   10                  15

Gln Phe Glu Ala Gly Ile Pro Gly Ser Glu Asp Pro Asn Ser Asp Trp
            20                  25                  30

Trp Val Trp Val His Asp Pro Glu Asn Thr Ala Ala Gly Leu Val Ser
        35                  40                  45

Gly Asp Leu Pro Glu Asn Gly Pro Gly Tyr Trp Asn Leu Tyr Lys Asn
    50                  55                  60

Asp His Asp Leu Ala Glu Lys Leu Gly Val Asn Thr Ile Arg Val Gly
65              70                  75                  80

Val Glu Trp Ser Arg Ile Phe Pro Lys Pro Thr Phe Asn Val Lys Val
                85                  90                  95

Pro Val Glu Arg Asp Glu Asn Gly Ser Ile Val His Val Asp Val Asp
            100                 105                 110

Asp Lys Ala Val Glu Arg Leu Asp Glu Leu Ala Asn Lys Glu Ala Val
        115                 120                 125

Asn His Tyr Val Glu Met Tyr Lys Asp Trp Val Glu Arg Gly Arg Lys
    130                 135                 140

Leu Ile Leu Asn Leu Tyr His Trp Pro Leu Pro Leu Trp Leu His Asn
145                 150                 155                 160

Pro Ile Met Val Arg Arg Met Gly Pro Asp Arg Ala Pro Ser Gly Trp
                165                 170                 175

Leu Asn Glu Glu Ser Val Val Glu Phe Ala Lys Tyr Ala Ala Tyr Ile
            180                 185                 190
```

Ala Trp Lys Met Gly Glu Leu Pro Val Met Trp Ser Thr Met Asn Glu
        195                 200                 205

Pro Asn Val Val Tyr Glu Gln Gly Tyr Met Phe Val Lys Gly Gly Phe
        210                 215                 220

Pro Pro Gly Tyr Leu Ser Phe Glu Ala Ala Asp Lys Ala Arg Arg Asn
225                 230                 235                 240

Met Ile Gln Ala His Ala Arg Ala Tyr Asp Asn Ile Lys Arg Phe Ser
            245                 250                 255

Lys Lys Pro Val Gly Leu Ile Tyr Ala Phe Gln Trp Phe Glu Leu Leu
        260                 265                 270

Glu Gly Pro Ala Glu Val Phe Asp Lys Phe Lys Ser Ser Lys Leu Tyr
            275                 280                 285

Tyr Phe Thr Asp Ile Val Ser Lys Gly Ser Ser Ile Ile Asn Ala Glu
        290                 295                 300

Tyr Arg Arg Asp Leu Ala Asn Arg Leu Asp Trp Leu Gly Val Asn Tyr
305                 310                 315                 320

Tyr Ser Arg Leu Val Tyr Lys Ile Val Asp Asp Lys Pro Ile Ile Leu
            325                 330                 335

His Gly Tyr Gly Phe Leu Cys Thr Pro Gly Gly Ile Ser Pro Ala Glu
        340                 345                 350

Asn Pro Cys Ser Asp Phe Gly Trp Glu Val Tyr Pro Glu Gly Leu Tyr
        355                 360                 365

Leu Leu Leu Lys Glu Leu Tyr Asn Arg Tyr Gly Val Asp Leu Ile Val
        370                 375                 380

Thr Glu Asn Gly Val Ser Asp Ser Arg Asp Ala Leu Arg Pro Ala Tyr
385                 390                 395                 400

Leu Val Ser His Val Tyr Ser Val Trp Lys Ala Val Asn Glu Gly Ile
            405                 410                 415

Pro Val Lys Gly Tyr Leu His Trp Ser Leu Thr Asp Asn Tyr Glu Trp
        420                 425                 430

Ala Gln Gly Phe Arg Gln Lys Phe Gly Leu Val Met Val Asp Phe Lys
        435                 440                 445

Thr Lys Lys Arg Tyr Leu Arg Pro Ser Ala Leu Val Phe Arg Glu Ile
        450                 455                 460

Ala Thr His Asn Gly Ile Pro Asp Glu Leu Gln His Leu Thr Leu Ile
465                 470                 475                 480

Gln

<210> SEQ ID NO 14
<211> LENGTH: 486
<212> TYPE: PRT
<213> ORGANISM: Caldivirga maquilingensis

<400> SEQUENCE: 14

Met Ile Lys Phe Pro Ser Asp Phe Arg Phe Gly Phe Ser Thr Val Gly
1               5                   10                  15

Thr Gln His Glu Met Gly Thr Pro Gly Ser Glu Phe Val Ser Asp Trp
            20                  25                  30

Tyr Val Trp Leu His Asp Pro Glu Asn Ile Ala Ser Gly Leu Val Ser
        35                  40                  45

Gly Asp Leu Pro Glu His Gly Pro Gly Tyr Trp Asp Leu Tyr Lys Gln
    50                  55                  60

Asp His Ser Ile Ala Arg Asp Leu Gly Leu Asp Ala Ala Trp Ile Thr
65                  70                  75                  80

```
Ile Glu Trp Ala Arg Val Phe Pro Lys Pro Thr Phe Asp Val Lys Val
             85                  90                  95

Lys Val Asp Glu Asp Asp Gly Gly Asn Val Val Asp Val Glu Val Asn
            100                 105                 110

Glu Ser Ala Leu Glu Glu Leu Arg Arg Leu Ala Asp Leu Asn Ala Val
            115                 120                 125

Asn His Tyr Arg Gly Ile Leu Ser Asp Trp Lys Glu Arg Gly Gly Leu
130                 135                 140

Leu Val Ile Asn Leu Tyr His Trp Ala Met Pro Thr Trp Leu His Asp
145                 150                 155                 160

Pro Ile Ala Val Arg Lys Asn Gly Pro Asp Arg Ala Pro Ser Gly Trp
                165                 170                 175

Leu Asp Lys Arg Ser Val Ile Glu Phe Thr Lys Phe Ala Ala Phe Ile
            180                 185                 190

Ala His Glu Leu Gly Asp Leu Ala Asp Met Trp Tyr Thr Met Asn Glu
            195                 200                 205

Pro Gly Val Val Ile Thr Glu Gly Tyr Leu Tyr Val Lys Ser Gly Phe
210                 215                 220

Pro Pro Gly Tyr Leu Asp Leu Asn Ser Leu Ala Thr Ala Gly Lys His
225                 230                 235                 240

Leu Ile Glu Ala His Ala Arg Ala Tyr Asp Ala Ile Lys Ala Tyr Ser
                245                 250                 255

Arg Lys Pro Val Gly Leu Val Tyr Ser Phe Ala Asp Tyr Gln Pro Leu
            260                 265                 270

Arg Gln Gly Asp Glu Glu Ala Val Lys Glu Ala Lys Gly Leu Asp Tyr
            275                 280                 285

Ser Phe Phe Asp Ala Pro Ile Lys Gly Glu Leu Met Gly Val Thr Arg
290                 295                 300

Asp Asp Leu Lys Gly Arg Leu Asp Trp Ile Gly Val Asn Tyr Tyr Thr
305                 310                 315                 320

Arg Ala Val Leu Arg Arg Gln Asp Ala Gly Arg Ala Ser Val Ala
                325                 330                 335

Val Val Asp Gly Phe Gly Tyr Ser Cys Glu Pro Gly Gly Val Ser Asn
            340                 345                 350

Asp Arg Arg Pro Cys Ser Asp Phe Gly Trp Glu Ile Tyr Pro Glu Gly
            355                 360                 365

Val Tyr Asn Val Leu Met Asp Leu Trp Arg Arg Tyr Arg Met Pro Met
370                 375                 380

Tyr Ile Thr Glu Asn Gly Ile Ala Asp Glu His Asp Lys Trp Arg Ser
385                 390                 395                 400

Trp Phe Ile Val Ser His Leu Tyr Gln Ile His Arg Ala Met Glu Glu
                405                 410                 415

Gly Val Asp Val Arg Gly Tyr Phe His Trp Asn Leu Ile Asp Asn Leu
            420                 425                 430

Glu Trp Ala Ala Gly Tyr Arg Met Arg Phe Gly Leu Val Tyr Val Asp
            435                 440                 445

Tyr Ala Thr Lys Arg Arg Tyr Phe Arg Pro Ser Ala Leu Val Met Arg
450                 455                 460

Glu Val Ala Lys Gln Lys Ala Ile Pro Asp Tyr Leu Glu His Tyr Ile
465                 470                 475                 480

Lys Pro Pro Arg Ile Glu
                485
```

<210> SEQ ID NO 15
<211> LENGTH: 420
<212> TYPE: PRT
<213> ORGANISM: Pyrococcus furiosus

<400> SEQUENCE: 15

```
Pro Leu Lys Phe Pro Glu Glu Phe Leu Phe Gly Thr Ala Thr Ala Ala
1               5                   10                  15

His Gln Ile Glu Gly Asp Asn Lys Trp Asn Asp Trp Trp Tyr Tyr Glu
            20                  25                  30

Gln Ile Gly Lys Leu Pro Tyr Lys Ser Gly Lys Ala Cys Asn His Trp
        35                  40                  45

Glu Phe Tyr Lys Glu Asp Ile Gln Leu Met Ala Ser Leu Gly Tyr Asn
    50                  55                  60

Ala Tyr Arg Phe Ser Ile Glu Trp Ser Arg Leu Phe Pro Glu Glu Asn
65                  70                  75                  80

Lys Phe Asn Glu Glu Ala Phe Asn Arg Tyr Gln Glu Ile Ile Asp Leu
                85                  90                  95

Leu Leu Ala Asn Asn Ile Thr Pro Leu Val Thr Leu His His Phe Thr
            100                 105                 110

Ser Pro Leu Trp Phe Met Lys Lys Gly Gly Phe Leu Arg Glu Glu Asn
        115                 120                 125

Leu Lys Phe Trp Glu Lys Tyr Val Glu Lys Val Ala Glu Leu Leu Glu
    130                 135                 140

Lys Val Lys Leu Ile Ala Thr Phe Asn Glu Pro Met Val Tyr Val Met
145                 150                 155                 160

Met Gly Tyr Leu Thr Ala Tyr Trp Pro Pro Phe Ile Lys Ser Pro Phe
                165                 170                 175

Lys Ala Phe Lys Val Ala Ser Asn Leu Leu Lys Ala His Ala Leu Ala
            180                 185                 190

Tyr Glu Ile Leu His Gly Lys Phe Gln Val Gly Ile Val Lys Asn Val
        195                 200                 205

Pro Ile Met Leu Pro Ala Thr Asp Lys Glu Arg Asp Lys Lys Ala Ala
    210                 215                 220

Glu Arg Ala Asp Asn Leu Phe Asn Trp Tyr Phe Leu Asp Ala Ile Trp
225                 230                 235                 240

Ser Gly Val Tyr Arg Gly Ala Phe Lys Ala Tyr Arg Val Pro Gln Ser
                245                 250                 255

Asp Ala Asp Phe Ile Gly Ile Asn Tyr Tyr Thr Ala Ser Glu Val Arg
            260                 265                 270

His Ser Trp Asn Pro Leu Lys Phe Phe Asp Ala Lys Leu Ala Asp
        275                 280                 285

Val Ser Glu Arg Lys Thr Gln Met Gly Trp Ser Val Tyr Pro Arg Gly
    290                 295                 300

Ile Tyr Ile Ala Leu Lys Lys Ala Ser Lys Tyr Gly Lys Pro Leu Tyr
305                 310                 315                 320

Ile Thr Glu Asn Gly Ile Ala Thr Leu Asp Asp Glu Trp Arg Ile Glu
                325                 330                 335

Phe Ile Ile Gln His Leu Gln Tyr Val His Lys Ala Ile Glu Asp Gly
            340                 345                 350

Leu Asp Val Arg Gly Tyr Phe Tyr Trp Ser Phe Met Asp Asn Tyr Glu
        355                 360                 365

Trp Arg Glu Gly Phe Glu Pro Arg Phe Gly Leu Val Glu Val Asp Tyr
370                 375                 380
```

```
Glu Thr Phe Glu Arg Arg Pro Arg Lys Ser Ala Tyr Ile Tyr Gly Gly
385                 390                 395                 400

Ile Ala Lys Ser Lys Glu Ile Lys Asp Glu Ile Leu Glu Lys Tyr Gly
                405                 410                 415

Leu Ser Ser Leu
            420

<210> SEQ ID NO 16
<211> LENGTH: 422
<212> TYPE: PRT
<213> ORGANISM: Pyrococcus horikoshii

<400> SEQUENCE: 16

Pro Leu Lys Phe Pro Glu Met Phe Leu Phe Gly Thr Ala Thr Ser Ser
1               5                   10                  15

His Gln Ile Glu Gly Asn Asn Arg Trp Asn Asp Trp Trp Tyr Tyr Glu
            20                  25                  30

Gln Ile Gly Lys Leu Pro Tyr Arg Ser Gly Lys Ala Cys Asn His Trp
        35                  40                  45

Glu Leu Tyr Arg Asp Asp Ile Gln Leu Met Thr Ser Leu Gly Tyr Asn
50                  55                  60

Ala Tyr Arg Phe Ser Ile Glu Trp Ser Arg Leu Phe Pro Glu Glu Asn
65                  70                  75                  80

Lys Phe Asn Glu Asp Ala Phe Met Lys Tyr Arg Glu Ile Ile Asp Leu
                85                  90                  95

Leu Leu Thr Arg Gly Ile Thr Pro Leu Val Thr Leu His His Phe Thr
            100                 105                 110

Ser Pro Leu Trp Phe Met Lys Lys Gly Gly Phe Leu Arg Glu Glu Asn
        115                 120                 125

Leu Lys His Trp Glu Lys Tyr Ile Glu Lys Val Ala Glu Leu Leu Glu
130                 135                 140

Lys Val Lys Leu Val Ala Thr Phe Asn Glu Pro Met Val Tyr Val Met
145                 150                 155                 160

Met Gly Tyr Leu Thr Ala Tyr Trp Pro Pro Phe Ile Arg Ser Pro Phe
                165                 170                 175

Lys Ala Phe Lys Val Ala Ala Asn Leu Leu Lys Ala His Ala Ile Ala
            180                 185                 190

Tyr Glu Leu Leu His Gly Lys Phe Lys Val Gly Ile Val Lys Asn Ile
        195                 200                 205

Pro Ile Ile Leu Pro Ala Ser Asp Lys Glu Arg Asp Arg Lys Ala Ala
210                 215                 220

Glu Lys Ala Asp Asn Leu Phe Asn Trp His Phe Leu Asp Ala Ile Trp
225                 230                 235                 240

Ser Gly Lys Tyr Arg Gly Val Phe Lys Thr Tyr Arg Ile Pro Gln Ser
                245                 250                 255

Asp Ala Asp Phe Ile Gly Val Asn Tyr Tyr Thr Ala Ser Glu Val Arg
            260                 265                 270

His Thr Trp Asn Pro Leu Lys Phe Phe Glu Val Lys Leu Ala Asp
        275                 280                 285

Ile Ser Glu Arg Lys Thr Gln Met Gly Trp Ser Val Tyr Pro Lys Gly
290                 295                 300

Ile Tyr Met Ala Leu Lys Lys Ala Ser Arg Tyr Gly Arg Pro Leu Tyr
305                 310                 315                 320

Ile Thr Glu Asn Gly Ile Ala Thr Leu Asp Asp Glu Trp Arg Val Glu
```

```
                325                 330                 335
Phe Ile Ile Gln His Leu Gln Tyr Val His Lys Ala Ile Glu Asp Gly
            340                 345                 350

Leu Asp Val Arg Gly Tyr Phe Tyr Trp Ser Phe Met Asp Asn Tyr Glu
        355                 360                 365

Trp Lys Glu Gly Phe Gly Pro Arg Phe Gly Leu Val Glu Val Asp Tyr
    370                 375                 380

Gln Thr Phe Glu Arg Arg Pro Arg Lys Ser Ala Tyr Val Tyr Gly Glu
385                 390                 395                 400

Ile Ala Arg Ser Lys Glu Ile Lys Asp Glu Leu Leu Lys Arg Tyr Gly
                405                 410                 415

Leu Pro Glu Leu Gln Leu
            420

<210> SEQ ID NO 17
<211> LENGTH: 417
<212> TYPE: PRT
<213> ORGANISM: Thermococcus litoralis

<400> SEQUENCE: 17

Phe Pro Glu Lys Phe Leu Phe Gly Thr Ser Thr Ala Ala His Gln Val
1               5                   10                  15

Glu Gly Asp Asn Arg Trp Asn Asp Trp Trp Tyr Tyr Glu Glu Ile Gly
            20                  25                  30

Lys Leu Pro Tyr Lys Ser Gly Lys Ala Cys Asn His Trp Gly Leu Tyr
        35                  40                  45

Arg Glu Asp Ile Glu Leu Met Ala Gln Leu Gly Tyr Asn Ala Tyr Arg
    50                  55                  60

Phe Ser Ile Glu Trp Ser Arg Leu Phe Pro Glu Glu Gly Lys Phe Asn
65                  70                  75                  80

Glu Asp Ala Phe Asn Arg Tyr Arg Glu Ile Ile Glu Leu Leu Leu Glu
                85                  90                  95

Lys Gly Ile Thr Pro Asn Val Thr Leu His His Phe Thr Ser Pro Leu
            100                 105                 110

Trp Phe Met Arg Lys Gly Gly Phe Leu Lys Glu Asn Leu Lys Tyr
        115                 120                 125

Trp Glu Lys Tyr Val Asp Lys Ala Ala Glu Leu Leu Lys Gly Val Lys
    130                 135                 140

Leu Val Ala Thr Phe Asn Glu Pro Met Val Tyr Val Met Met Gly Tyr
145                 150                 155                 160

Leu Thr Ala Tyr Trp Pro Pro Phe Val Lys Ser Pro Phe Lys Ala Phe
                165                 170                 175

Lys Val Ala Ala Asn Leu Leu Lys Ala His Ala Met Ala Tyr Asp Ile
            180                 185                 190

Leu His Gly Asn Phe Asp Val Gly Ile Val Lys Asn Ile Pro Ile Met
        195                 200                 205

Leu Pro Ala Ser Asn Arg Glu Lys Asp Ile Lys Ala Ala Gln Lys Ala
    210                 215                 220

Asp Asn Leu Phe Asn Trp Asn Phe Leu Asp Ala Ile Trp Ser Gly Lys
225                 230                 235                 240

Tyr Lys Gly Ala Phe Gly Thr Tyr Lys Thr Pro Glu Ser Asp Val Asp
                245                 250                 255

Phe Ile Gly Ile Asn Tyr Tyr Thr Ala Ser Glu Val Arg His Ser Trp
            260                 265                 270
```

-continued

```
Asn Pro Leu Lys Phe Phe Asp Ala Lys Leu Ala Asp Leu Ser Glu
            275                 280                 285

Arg Lys Thr Asp Met Gly Trp Ser Val Tyr Pro Lys Gly Ile Tyr Glu
290                 295                 300

Ala Ile Ala Lys Val Ser Arg Tyr Gly Lys Pro Met Tyr Ile Thr Glu
305                 310                 315                 320

Asn Gly Ile Ala Thr Leu Glu Asp Glu Trp Arg Ile Glu Phe Ile Ile
            325                 330                 335

Gln His Leu Gln Tyr Val His Lys Ala Leu Asn Asp Gly Phe Asp Leu
            340                 345                 350

Arg Gly Tyr Phe Tyr Trp Ser Phe Met Asp Asn Tyr Glu Trp Ala Glu
            355                 360                 365

Gly Phe Arg Pro Arg Phe Gly Leu Val Glu Val Asp Tyr Thr Thr Phe
370                 375                 380

Glu Arg Arg Pro Arg Lys Ser Gly Tyr Val Tyr Gly Glu Ile Ala Arg
385                 390                 395                 400

Glu Lys Lys Ile Lys Asp Glu Leu Leu Ala Lys Tyr Gly Leu Pro Glu
            405                 410                 415

Leu

<210> SEQ ID NO 18
<211> LENGTH: 422
<212> TYPE: PRT
<213> ORGANISM: Thermococcus sibiricus

<400> SEQUENCE: 18

Asn Ala Val Ile Val Phe Pro Lys Ser Phe Leu Phe Gly Thr Ala Thr
1               5                   10                  15

Ser Ser His Gln Ile Glu Gly Asn Asn Lys Trp Asn Asp Trp Trp Tyr
            20                  25                  30

Tyr Glu Gln Ile Gly Lys Leu Pro Tyr Lys Ser Gly Lys Ala Cys Asn
        35                  40                  45

His Trp Glu Leu Tyr Lys Glu Asp Ile Ser Leu Met His Ser Leu Gly
    50                  55                  60

Tyr Asp Gly Tyr Arg Phe Ser Ile Glu Trp Ser Arg Ile Phe Pro Lys
65                  70                  75                  80

Glu Asn Glu Ile Asp Glu Asn Ala Leu Asn Arg Tyr Leu Glu Ile Ile
                85                  90                  95

Glu Leu Leu Val Lys Ser Gly Ile Thr Pro Asn Val Thr Leu His His
            100                 105                 110

Phe Thr Ser Pro Ile Trp Phe Met Gln Arg Gly Gly Phe Ala Lys Glu
        115                 120                 125

Glu Asn Leu Lys Tyr Trp Glu Gln Tyr Val Glu Thr Val Ala Gly Ile
    130                 135                 140

Leu Lys Asp Val Lys Leu Val Ala Thr Phe Asn Glu Pro Met Val Tyr
145                 150                 155                 160

Val Met Met Gly Tyr Leu Thr Ala Tyr Trp Pro Pro Phe Val Lys Ser
                165                 170                 175

Pro Phe Lys Ala Phe Lys Val Ala Ala Asn Leu Leu Lys Ala His Ala
            180                 185                 190

Leu Ala Tyr Glu Ile Leu Ser Ser Arg Leu Lys Val Gly Ile Val Lys
        195                 200                 205

Asn Ile Pro Ile Met Leu Ala Ala Ser Tyr Met Glu Arg Asp Lys Lys
    210                 215                 220
```

Ala Ala Glu Lys Ala Asp Asn Leu Phe Asn Trp Asn Phe Leu Asp Ala
225                 230                 235                 240

Ile Trp Ser Gly Lys Leu Lys Gly Val Leu Ser Thr Tyr Thr Val Pro
            245                 250                 255

Glu Ser Asp Val Asp Phe Ile Gly Val Asn Tyr Tyr Thr Ala Ser Glu
                260                 265                 270

Val Lys Tyr Ser Trp Asn Pro Ile Lys Phe Phe Glu Ala Lys Leu
        275                 280                 285

Ala Asp Leu Ser Glu Arg Lys Thr Gln Met Gly Trp Ser Val Tyr Pro
            290                 295                 300

Glu Gly Ile Tyr Lys Ala Ile Thr Ala Val Ser Arg Tyr Glu Lys Pro
305                 310                 315                 320

Met Tyr Ile Thr Glu Asn Gly Ile Ala Thr Leu Asp Asp Glu Trp Arg
                325                 330                 335

Lys Glu Phe Val Val Gln His Leu Gln Tyr Val Gln Lys Ala Ile Asp
                340                 345                 350

Glu Gly Tyr Asp Val Arg Gly Tyr Phe Tyr Trp Ser Phe Met Asp Asn
            355                 360                 365

Tyr Glu Trp Lys Glu Gly Phe Glu Pro Arg Phe Gly Leu Ile Glu Ile
370                 375                 380

Asp Tyr Lys Thr Tyr Glu Arg Lys Pro Arg Glu Ser Ala Tyr Val Tyr
385                 390                 395                 400

Gly Glu Ile Ala Gln Lys Lys Glu Ile Ser Glu Leu Ile Lys Lys
            405                 410                 415

Tyr Gly Leu Lys Gly Leu
            420

<210> SEQ ID NO 19
<211> LENGTH: 412
<212> TYPE: PRT
<213> ORGANISM: Termococcus kodakarensis

<400> SEQUENCE: 19

Met Leu Ser Met Phe Pro Glu Lys Phe Leu Phe Gly Thr Ser Thr Ala
1               5                   10                  15

Ala His Gln Val Glu Gly Asp Asn Lys Trp Asn Asp Trp Trp Tyr Tyr
                20                  25                  30

Glu Glu Met Gly Lys Leu Pro Tyr Lys Ser Gly Lys Ala Cys Asn His
            35                  40                  45

Trp Glu Leu Tyr Arg Glu Asp Ile Glu Leu Met Ala Glu Leu Gly Tyr
50                  55                  60

Asn Ala Tyr Arg Phe Ser Ile Glu Trp Ser Arg Leu Phe Pro Glu Glu
65                  70                  75                  80

Gly Lys Phe Asn Glu Asp Ala Phe Asn Arg Tyr Arg Glu Ile Ile Glu
                85                  90                  95

Leu Leu Leu Glu Lys Gly Ile Thr Pro Asn Val Thr Leu His His Phe
            100                 105                 110

Thr Ser Pro Leu Trp Phe Met Arg Lys Gly Gly Phe Leu Lys Glu Glu
            115                 120                 125

Asn Leu Lys Tyr Trp Glu Gly Tyr Val Asp Lys Ala Ala Glu Leu Leu
130                 135                 140

Lys Gly Val Lys Leu Val Ala Thr Phe Asn Glu Pro Leu Val Tyr Val
145                 150                 155                 160

Thr Met Gly Tyr Leu Thr Ala Tyr Trp Pro Pro Phe Ile Lys Ser Pro
                165                 170                 175

```
Phe Lys Ser Phe Arg Val Ala Ala Asn Leu Lys Ala His Ala Ile
            180                 185                 190

Ala Tyr Glu Leu Leu His Gly Lys Phe Gln Val Gly Ile Val Lys His
        195                 200                 205

Ile Arg Val Met Leu Pro Glu Arg Lys Gly Asp Glu Lys Ala Ala Gln
210                 215                 220

Lys Ala Asp Asn Leu Phe Asn Trp Tyr Phe Leu Asp Ala Ile Trp Ser
225                 230                 235                 240

Gly Lys Tyr Arg Gly Ala Phe Lys Thr Tyr Ser Val Pro Glu Ser Asp
                245                 250                 255

Ala Asp Phe Ile Gly Val Asn Tyr Tyr Thr Ala Ser Thr Val Arg Arg
                260                 265                 270

Ser Leu Asn Pro Leu Lys Met Phe Phe Glu Ala Lys Asp Ala Glu Ile
        275                 280                 285

Gly Glu Arg Arg Thr Gln Met Gly Trp Ser Val Tyr Pro Glu Gly Val
    290                 295                 300

Tyr Leu Ala Leu Arg Arg Ala Ser Glu Tyr Gly Arg Pro Leu Tyr Val
305                 310                 315                 320

Thr Glu Asn Gly Ile Ala Thr Leu Asp Asp Glu Trp Arg Lys Glu Phe
                325                 330                 335

Ile Ile Gln His Leu Arg Gln Val Leu Arg Ala Ile Glu Asp Gly Leu
                340                 345                 350

Asp Val Arg Gly Tyr Phe Tyr Trp Ser Leu Met Asp Asn Tyr Glu Trp
            355                 360                 365

Arg Glu Gly Phe Glu Pro Arg Phe Gly Leu Ile Glu Val Asp Phe Glu
370                 375                 380

Thr Phe Glu Arg Arg Pro Arg Gly Ser Ala Tyr Leu Tyr Gly Glu Ile
385                 390                 395                 400

Ala Arg Thr Lys Lys Leu Pro Gly Glu Glu Asp Pro
                405                 410

<210> SEQ ID NO 20
<211> LENGTH: 417
<212> TYPE: PRT
<213> ORGANISM: Aciduliprofundum boonei

<400> SEQUENCE: 20

Met Leu Lys Phe Pro Pro Asn Phe Ile Phe Gly Thr Ala Thr Ala Gly
1               5                   10                  15

His Gln Ile Glu Gly Asp Asn Val Asn Ser Asp Trp Trp His Tyr Glu
            20                  25                  30

Asn Met Gly Lys Leu Pro Tyr Lys Ser Gly Lys Thr Cys Asn His Trp
        35                  40                  45

Asn Leu Tyr Arg Gln Asp Ile Glu Leu Met Gln Ser Leu Gly Tyr Asn
    50                  55                  60

Ala Tyr Arg Phe Ser Ile Glu Trp Ala Arg Ile Phe Pro Lys Glu Gly
65                  70                  75                  80

Lys Ile Asp Lys Lys Ala Leu Gln Arg Tyr Arg Glu Ile Ile Asn Leu
                85                  90                  95

Leu Asn Lys Lys Gly Ile Ile Pro Met Val Thr Leu His His Phe Thr
            100                 105                 110

Leu Pro Leu Trp Phe Leu Glu Lys Gly Gly Phe Ala Lys Glu Glu Asn
        115                 120                 125

Leu Lys Tyr Trp Glu Asp Tyr Val Lys Ala Leu Lys Asp Ile Leu Asn
```

```
            130                 135                 140
Leu Lys Leu Ile Ala Thr Phe Asn Glu Pro Met Val Tyr Val Val Ala
145                 150                 155                 160

Gly Tyr Leu Ser Gly Glu Trp Pro Pro Phe Lys Lys Ala Pro Arg Ile
                165                 170                 175

Ala Ser Arg Val Ala Ala Asn Ile Leu Lys Ala His Ala Ile Ala Tyr
            180                 185                 190

Glu Ile Leu His Lys Glu His Glu Val Gly Ile Val Lys Asn Ile Pro
            195                 200                 205

Ile Phe Leu Ser Ala Ser Arg Arg Asn Asp Asp Leu Lys Ala Ala Arg
    210                 215                 220

Arg Ala Asp Asn Met Phe Asn Phe Ala Phe Leu Asp Val Ile Trp Asn
225                 230                 235                 240

Gly Glu Tyr Lys Gly Ile Ile Gly Lys Tyr Glu Val Pro Val Ser Asp
                245                 250                 255

Leu Asp Phe Ile Gly Val Asn Tyr Tyr Thr Ala Tyr Lys Val Arg His
            260                 265                 270

Ser Tyr Asn Pro Leu Lys Phe Phe Leu Asp Ala Lys Pro Ala Glu Met
        275                 280                 285

Gly Glu Arg Arg Thr Asp Met Gly Trp Ser Val Tyr Pro Glu Gly Ile
290                 295                 300

Tyr Lys Ala Val Glu Lys Ile Ser Arg Tyr Lys Lys Pro Ile Tyr Ile
305                 310                 315                 320

Thr Glu Asn Gly Ile Ala Thr Arg Asp Asp Glu Trp Arg Ile Ser Phe
                325                 330                 335

Ile Ile Gln His Leu Gln Tyr Leu Tyr Arg Ala Ile Lys Tyr Gly Tyr
            340                 345                 350

Asn Val Lys Gly Tyr Phe Tyr Trp Ser Phe Met Asp Asn Phe Glu Trp
        355                 360                 365

Asp Lys Gly Phe Ala Pro Arg Phe Gly Leu Val Glu Ile Asn Tyr Glu
    370                 375                 380

Asn Phe Gln Arg Lys Pro Arg Arg Ser Ala Tyr Val Tyr Gly Glu Ile
385                 390                 395                 400

Ser Lys Thr Lys Lys Ile Lys Asp Glu Val Leu Glu Lys Tyr Gly Glu
                405                 410                 415

Ser
```

<210> SEQ ID NO 21
<211> LENGTH: 416
<212> TYPE: PRT
<213> ORGANISM: Thermococcus barophilus

<400> SEQUENCE: 21

```
Met Leu Lys Phe Pro Asp His Phe Ile Phe Gly Thr Ala Thr Ser Ser
1               5                   10                  15

Tyr Gln Ile Glu Gly Asp Asn Ile Trp Ser Asp Trp Trp Tyr Trp Ala
                20                  25                  30

Glu Lys Gly Arg Leu Pro Lys Ala Gly Lys Ala Cys Asn His Trp Glu
            35                  40                  45

Leu Tyr Lys Glu Asp Ile Glu Leu Met Ala Ser Leu Asn Tyr Pro Ala
        50                  55                  60

Tyr Arg Leu Ser Val Glu Trp Ala Arg Ile Phe Pro Glu Gly Leu
65                  70                  75                  80

Leu Asn Glu Ser Ala Leu Glu Arg Tyr Gln Asp Ile Ile Asp Leu Leu
```

```
                    85                  90                  95
Asn Lys Lys Gly Ile Thr Pro Met Leu Thr Val His His Phe Thr Leu
            100                 105                 110

Pro Met Trp Phe Ala Leu Lys Gly Gly Phe Glu Lys Asp Glu Asn Leu
            115                 120                 125

Lys Tyr Trp Glu Glu Tyr Val Ser Val Ile Ala Glu Leu Lys Gly Val
            130                 135                 140

Glu Leu Val Ala Thr Phe Asn Glu Pro Met Val Tyr Val Ala Gly
145                 150                 155                 160

Tyr Leu Met Gly Met Trp Pro Pro Phe Lys Lys Asn Pro Pro Lys Ala
                165                 170                 175

Gly Lys Val Ala Ala Asn Leu Ile Asn Ala His Ala Ile Ala Tyr Glu
                180                 185                 190

Ile Leu His Gly Arg Phe Lys Val Gly Ile Val Lys Asn Tyr Gln His
                195                 200                 205

Phe Ile Pro Ala Thr Asn Ser Lys Arg Asp Lys Glu Ala Arg Asp Arg
            210                 215                 220

Val Asp Tyr Leu Phe Asn Trp Ala Phe Ile Asp Gly Ile Phe His Gly
225                 230                 235                 240

Ser Tyr Glu Ser Phe Met Lys Lys Tyr Lys Val Asn Glu Ser Asp Leu
                245                 250                 255

Asp Phe Ile Gly Ile Asn Tyr Tyr Asn Ile Gln Lys Val Lys Lys Ser
                260                 265                 270

Trp Asn Pro Leu Asn Pro Phe Ile Val Glu Asp Ala Ser Val Ser Arg
            275                 280                 285

Lys Thr Asp Met Gly Trp Ser Val Tyr Pro Lys Gly Ile Tyr Glu Gly
290                 295                 300

Ile Lys Ala Phe Ser Arg Tyr Glu Arg Pro Met Tyr Ile Thr Glu Asn
305                 310                 315                 320

Gly Ile Ala Thr Leu Asp Asp Gly Trp Arg Ile Glu Phe Ile Ile Gln
                325                 330                 335

His Leu Gln Tyr Val His Lys Ala Ile Arg Glu Asp Leu Asp Ile Asn
                340                 345                 350

Gly Tyr Phe Tyr Trp Ser Leu Met Asp Asn Tyr Glu Trp Ala Glu Gly
                355                 360                 365

Phe Arg Pro Arg Phe Gly Leu Val Glu Ile Asp Tyr Glu Thr Phe Glu
            370                 375                 380

Arg Lys Pro Arg Lys Ser Ala Tyr Val Tyr Gly Glu Ile Ala Lys Arg
385                 390                 395                 400

Lys Glu Ile Ser Asn Glu Leu Leu Glu Lys Tyr Gly Leu Arg Glu Leu
                405                 410                 415

<210> SEQ ID NO 22
<211> LENGTH: 420
<212> TYPE: PRT
<213> ORGANISM: Thermococcus alcaliphilus

<400> SEQUENCE: 22

Met Ile Val Phe Pro Glu Phe Phe Leu Phe Gly Thr Ala Thr Ser Ser
1               5                   10                  15

His Gln Ile Glu Gly Asp Asn Lys Trp Asn Asp Trp Trp Tyr Tyr Glu
                20                  25                  30

Glu Ile Gly Lys Leu Pro Tyr Lys Ser Gly Lys Ala Cys Asn His Trp
            35                  40                  45
```

-continued

```
Glu Leu Tyr Arg Glu Asp Ile Glu Leu Met Ala Gln Leu Gly Tyr Asn
 50                  55                  60

Ala Tyr Arg Phe Ser Ile Glu Trp Ser Arg Leu Phe Pro Glu Glu Gly
 65                  70                  75                  80

Lys Phe Asn Glu Glu Ala Phe Asn Arg Tyr Arg Glu Ile Ile Glu Ile
                     85                  90                  95

Leu Leu Glu Lys Gly Ile Thr Pro Asn Val Thr Leu His His Phe Thr
                 100                 105                 110

Ser Pro Leu Trp Phe Met Arg Lys Gly Phe Leu Lys Glu Glu Asn
                 115                 120                 125

Leu Lys Tyr Trp Glu Gln Tyr Val Asp Lys Ala Ala Glu Leu Leu Lys
 130                 135                 140

Gly Val Lys Leu Val Ala Thr Phe Asn Glu Pro Met Val Tyr Val Met
 145                 150                 155                 160

Met Gly Tyr Leu Thr Ala Tyr Trp Pro Pro Phe Ile Lys Ser Pro Phe
                 165                 170                 175

Lys Ala Phe Lys Val Ala Ala Asn Leu Leu Lys Ala His Ala Met Ala
                 180                 185                 190

Tyr Asp Ile Leu His Gly Asn Phe Asp Val Gly Ile Val Lys Asn Ile
                 195                 200                 205

Pro Ile Met Leu Pro Ala Ser Asn Arg Glu Lys Asp Val Glu Ala Ala
                 210                 215                 220

Gln Lys Ala Asp Asn Leu Phe Asn Trp Asn Phe Leu Asp Ala Ile Trp
225                 230                 235                 240

Ser Gly Lys Tyr Lys Gly Ala Phe Gly Thr Tyr Lys Thr Pro Glu Ser
                 245                 250                 255

Asp Ala Asp Phe Ile Gly Ile Asn Tyr Tyr Thr Ala Ser Glu Val Arg
                 260                 265                 270

His Ser Trp Asn Pro Leu Lys Phe Phe Phe Asp Ala Lys Leu Ala Asp
                 275                 280                 285

Leu Ser Glu Arg Lys Thr Asp Met Gly Trp Ser Val Tyr Pro Lys Gly
                 290                 295                 300

Ile Tyr Glu Ala Ile Ala Lys Val Ser His Tyr Gly Lys Pro Met Tyr
305                 310                 315                 320

Ile Thr Glu Asn Gly Ile Ala Thr Leu Asp Asp Glu Trp Arg Ile Glu
                 325                 330                 335

Phe Ile Ile Gln His Leu Gln Tyr Val His Lys Ala Leu Asn Asp Gly
                 340                 345                 350

Phe Asp Leu Arg Gly Tyr Phe Tyr Trp Ser Phe Met Asp Asn Phe Glu
                 355                 360                 365

Trp Ala Glu Gly Phe Arg Pro Arg Phe Gly Leu Val Glu Val Asp Tyr
 370                 375                 380

Thr Thr Phe Lys Arg Arg Pro Arg Lys Ser Ala Tyr Ile Tyr Gly Glu
385                 390                 395                 400

Ile Ala Arg Glu Lys Lys Ile Lys Asp Glu Leu Leu Ala Lys Tyr Gly
                 405                 410                 415

Leu Pro Glu Leu
                 420
```